United States Patent
Kuo et al.

(10) Patent No.: US 10,793,542 B2
(45) Date of Patent: Oct. 6, 2020

(54) HETROARYLAMINE COMPOUNDS FOR MODULATING THE HEDGEHOG PATHWAY AND PREPARING METHOD AND USES THEREOF

(71) Applicant: DEVELOPMENT CENTER FOR BIOTECHNOLOGY, New Taipei (TW)

(72) Inventors: Mann-Yan Kuo, Taipei (TW); Ying-Shuan Lee, Taipei (TW); Yann-Yu Lu, Taipei (TW); Chia-Wei Liu, Taipei (TW); Seline Hsieh, Taipei (TW); Ju-Ying Yang, Taipei (TW)

(73) Assignee: DEVELOPMENT CENTER FOR BIOTECHNOLOGY, Taipei (TW)

( * ) Notice: Subject to any disclaimer, the term of this patent is extended or adjusted under 35 U.S.C. 154(b) by 0 days.

(21) Appl. No.: 16/462,589

(22) PCT Filed: Nov. 22, 2017

(86) PCT No.: PCT/US2017/062974
§ 371 (c)(1),
(2) Date: May 21, 2019

(87) PCT Pub. No.: WO2018/098250
PCT Pub. Date: May 31, 2018

(65) Prior Publication Data
US 2020/0079753 A1 Mar. 12, 2020

Related U.S. Application Data

(60) Provisional application No. 62/425,394, filed on Nov. 22, 2016.

(51) Int. Cl.
| | | |
|---|---|---|
| C07D 213/74 | (2006.01) |
| C07D 239/47 | (2006.01) |
| C07D 239/48 | (2006.01) |
| C07D 401/04 | (2006.01) |
| C07D 401/12 | (2006.01) |
| C07D 403/04 | (2006.01) |
| A61P 35/00 | (2006.01) |
| C07D 239/38 | (2006.01) |
| C07D 403/12 | (2006.01) |
| C07D 413/12 | (2006.01) |
| C07D 413/14 | (2006.01) |
| A61K 45/06 | (2006.01) |

(52) U.S. Cl.
CPC ............ *C07D 401/04* (2013.01); *A61P 35/00* (2018.01); *C07D 213/74* (2013.01); *C07D 239/38* (2013.01); *C07D 239/47* (2013.01); *C07D 239/48* (2013.01); *C07D 401/12* (2013.01); *C07D 403/04* (2013.01); *C07D 403/12* (2013.01); *C07D 413/12* (2013.01); *C07D 413/14* (2013.01); *A61K 45/06* (2013.01)

(58) Field of Classification Search
CPC .. C07D 213/74; C07D 239/47; C07D 239/48; C07D 401/04; C07D 401/12; C07D 403/04
See application file for complete search history.

(56) References Cited

U.S. PATENT DOCUMENTS

| | | |
|---|---|---|
| 2009/0105211 A1 | 4/2009 | Bahceci et al. |
| 2009/0318405 A1 | 12/2009 | Li |
| 2010/0009990 A1 | 1/2010 | Venkataramani |
| 2010/0029638 A1 | 2/2010 | Melvin, Jr. et al. |
| 2012/0288492 A1 | 11/2012 | Kuo et al. |

FOREIGN PATENT DOCUMENTS

CN 103864770 A 6/2014

OTHER PUBLICATIONS

International Search Report in International Application No. PCT/US2017/062974, dated Mar. 19, 2018.
Written Opinion of the International Search Authority in International Application No. PCT/US2017/062974, dated Mar. 19, 2018.
Qiang Xiao et al., "Discovery of 5-(methylthio)pyrimidine derivatives as L858R/T790M mutant selective epidermal growth factor receptor (EGFR) inhibitors", Bioorganic & Medicinal Chemistry; vol. 24; No. 12; (Jun. 15, 2016); pp. 2673-2680, URL: https://doi.org/10.1016/j.bme.2016.04.03 2, XP029556529 [A] 1-15. Entire Document. DOI: http://dx.doi.org/10.1016/j.bme.2016.04.032, 2016.

*Primary Examiner* — Laura L Stockton
(74) *Attorney, Agent, or Firm* — Ladas & Parry LLP

(57) ABSTRACT

The present invention provides a compound of formula (1):

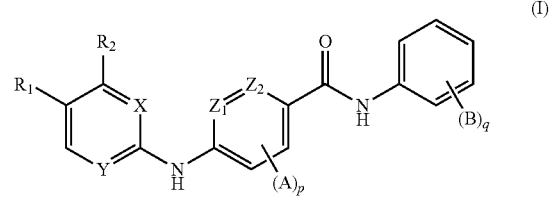

wherein X, Y, $Z_1$, $Z_2$, $R_1$, $R_2$, A, B, p and q are as disclosed in the specification. A pharmaceutical composition and a method for modulating the Hedgehog pathway are also provided. The present invention rurthe r provides a process for preparing the compound.

7 Claims, No Drawings

HETROARYLAMINE COMPOUNDS FOR MODULATING THE HEDGEHOG PATHWAY AND PREPARING METHOD AND USES THEREOF

CROSS REFERENCE TO THE RELATED APPLICATION

This application claims the benefit of U.S. Provisional Patent Application No. 62/425,394, filed on Nov. 22, 2016, the entire content of which is incorporated by reference.

FIELD OF THE INVENTION

The present invention relates to heteroarylamine compounds which are useful for modulating the Hedgehog pathway and pharmaceutical compositions comprising the compounds, as well as preparing methods and uses of the compounds. The compounds of the present invention are particularly effective in patients who show resistance to known smoothened (Smo) antagonists such as vismodegib/GDC-0449 and sonidegib/NVPLDE225. In particular, the compounds of the present invention are active against a Smo wild type and mutant (D473H) cell line identified in medulloblastoma patients who experienced a relapse after an initial response to vismodegib. The compounds of the present invention are also multikinase inhibitors that have activity against Flt-3, CSF1-R and AXL.

BACKGROUND OF THE INVENTION

The Hedgehog (Hh) pathway plays an important role in embryonic development and tissue patterning, and a lesser role in adults for tissue maintenance and repair. Smo, a 7-pass transmembrane receptor with a GPCR-like architecture, is a key component of the Hh signaling pathway, the activity of which is suppressed by the 12-pass transmembrane protein Patched (Ptch). The binding of secreted proteins of the Hh family to Ptch results in relief of the suppression of Smo, initiating downstream signaling and activation of Gli transcription factors which lead to cell proliferation, differentiation and survival. Genetic activation of the Hh pathway, mostly by Ptch loss-of-function or Smo gain-of-function mutations, has been linked to tumorigenesis in cancers such as basal cell carcinoma (BCC) and medulloblastoma. Furthermore, up-regulation of the pathway has been linked to tumor growth in pancreatic, prostate, lung, colorectal, bladder, and ovarian cancers. Recently, Smo-dependent non-canonical signaling through a $Ca^{2+}$-Ampk axis has been implicated in stimulating glucose uptake, resulting in Warburg-like metabolism in muscle and brown fat. Smo antagonists, such as vismodegib/GDC-0449 and sonidegib/NVPLDE225, have demonstrated clinical response in patients with BCC and medulloblastoma. Vismodegib was approved in January 2012 by the U.S.A. Food and Drug Administration (FDA) for the treatment of adults with metastatic or locally advanced BCC. However, micromolar concentrations are required in preclinical models for efficacy, and in at least one patient, loss of efficacy occurred from a single point mutation in Smo that prevented the binding of GDC-0449. Furthermore, adverse events of muscle spasms and weight loss occurred in >50% of the patients, possibly related to activation of non-canonical Hedgehog signaling. Because of resistance and the presence of mutations downstream of Smo, not all patients respond to Smo inhibitors. It has been found that patients who are administered with vismodegib/GDC-0449 and sonidegib/NVPLDE225 show resistance to these Smo antagonists.

Documents relating to Hedgehog signal conduction inhibitors are also seen in, for example, CN103864770 A and WO 2008/112913 A1.

CN103864770 A discloses pyrimidinamine and pyridinamine Hedgehog signal conduction inhibitors having the following formula:

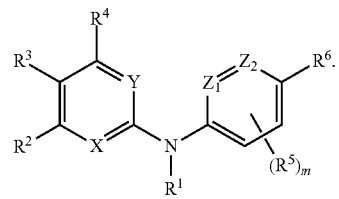

CN103864770 A does not disclose any compounds in which $R^3$ is attached to a pyrimidinyl ring or pyridinyl ring via an oxygen atom or a sulfur atom.

WO 2008/112913 A1 discloses compounds of formula I:

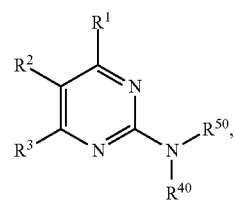

specifically, in the compound of formula I of WO 2008/112913 A1, $R^2$, and $R^3$, together with the pyrimidinyl to which they are attached, form a heterocyclic group.

However, there is a need for new compounds that are potent Hedgehog pathway modulators. The present invention addresses this need.

SUMMARY OF THE INVENTION

One aspect of the invention is to provide a compound of formula (I):

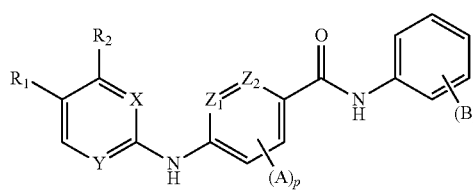

wherein X, Y, $Z_1$, $Z_2$, $R_1$, $R_2$, A, B, p and q are as defined in the specification, or a pharmaceutically acceptable salt, geometric isomer, enantiomer, diastereomer, racemate, prodrug, solvate, or hydrate thereof.

Another aspect of the invention is to provide a pharmaceutical composition comprising a therapeutically effective amount of a compound of formula (I) or a pharmaceutically acceptable salt, geometric isomer, enantiomer, diastereomer, racemate, prodrug, solvate, or hydrate thereof, and one or more pharmaceutically acceptable carriers or excipients therefor. The pharmaceutical composition of the present invention is effective in modulating the Hedgehog pathway.

Another aspect of the invention is to provide the use of a compound of formula (I) or a pharmaceutically acceptable salt, geometric isomer, enantiomer, diastereomer, racemate, prodrug, solvate, or hydrate thereof in the manufacture of a medicament for modulating the Hedgehog pathway.

Another aspect of the invention is to provide a method for treating cancer comprising administering a therapeutically effective amount of a compound of formula (I) or a pharmaceutically acceptable salt, geometric isomer, enantiomer, diastercomer, racemate, prodrug, solvate, or hydrate thereof to a subject in need, so that the growth of the cancer in the subject is inhibited. The compound of formula (I) can be used alone or in combination with another therapeutic agent and/or therapy.

Another aspect of the invention is to provide a method for preparing, a compound of formula (I) or a pharaceutically acceptable salt, geometric isomer, enantiomer, diastercomer, racemate, prodrug, solvate, or hydrate thereof.

DETAILED DESCRIPTION

The present invention can be understood more readily by reference to the following detailed description of various embodiments of the invention, the examples, and the tables with their relevant descriptions. Unless otherwise defined, all terms (including techincal and scientific terms) used hereinn have the same meaning as commonly understood by one of ordinary skill in the art which this invention belongs. It will be further understood that terms such as those defined in commonly used dictionaries should be interpreted consistently with their meaning in the context of the relevant art and will not be interpreted in an idealized or overly formal sense unless expressly so defined herein. It is also to be understood that the terminology used herein is for the purpose of describing particular embodiments only, and is not intended to be limiting.

Definitions

The definitions set forth in this section are intended to clarify terms used throughout this application. The term "herein" means the entire application.

It must be noted that, as used herein, the singular forms "a," "an" and "the" include plural referents unless the context clearly dictates otherwise. Thus, unless otherwise required by context, singular terms shall include the plural, and plural terms shall include the singular.

Often, ranges are expressed herein as from "about " one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein, the term "about" refers to ±20%, preferably ±10%, and even more preferably ±5%.

As used herein, the phrase "optionally substituted" means that substitution is optional. In the event that a substitution is desired, then such substitution means that any number of hydrogens on the designated atom is replaced with a selection from the indicated group, provided that the normal valence of the designated atom is not exceeded, and that the substitution results in a stable compound. For example, when a substituent is keto (i.e., =O), then 2 hydrogens on the atom are replaced. Examples of substituents for a "substituted" group are those found in the exemplary compounds and embodiments disclosed herein and can include, for example, halo, cyano, alkyl, alkoxy, haloalkyl, alkylamino, aminoalkyl, dialkylamino, hydroxylalkyl, alkoxyalkyl, hydroxyalkoxy, alkoxyalkoxy, aminoalkoxy, alkylaminoalkoxy, alkylaminoalkyl, and the like.

As used herein, the term "halo" includes fluoro, chloro, bromo and iodio. "Halo," used as a prefix of a group, means that one or more hydrogens on the group are replaced with one or more halogens.

The term "alkyl" used herein refers to a monovalent, saturated, straight or branched hydrocarbon radical containing 1 to 12 carbon atoms. Preferably, the alkyl is a $C_1$-$C_8$ alkyl group. More preferably, the alkyl is a $C_1$-$C_6$ alkyl group. The alkyl can be unsubstituted or substituted with one or more substituents. Example of a $C_1$-$C_6$ alkyl group include, but are not limited to, methyl, ethyl, n-propyl, isopropyl, n-butyl, isobutyl, see-butyl, t-butyl, pentyl (including all isometric forms), and hexyl (including all isomeric forms), heptyl (including all isomeric forms), octyl (including all isomeric forms) and the like.

The term "alkoxy," used alone or as a suffix or prefix, refers to radicals of the general formula —O—(alkyl), wherein alkyl is defined above. Exemplary alkoxy includes, but is not limited to, methoxy, ethoxy, n-propoxy, iso-propoxy, n-butoxy, iso-butoxy, sec-butoxy, tert-butoxy, and the like.

"Amino," used as a prefix or suffix of a group, means one or more hydrogens on the group are replaced with one or more amino groups.

The term "cycloalkyl" used herein refers to a saturated, monovalent hydrocarbon radical having cyclic configurations, including monocyclic, bicyclic, tricyclic, and higher multicyclic alkyl radicals (and, when multicyclic, including fused and bridged bicyclic and spirocyclic moieties) wherein each cyclic moiety has from 3 to 12 carbon atoms. Preferably, the cycloaklyl has from 3 to 8 carbon atoms. More preferably, the cycloalkyl has from 3 to 6 carbon atoms. When cycloaklyl contains more than one ring, the rings may be fused or unfused and include bicyclo radicals. Fused rings generally refer to at least two rings sharing two atoms therebetween. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like.

The term "aryl" means a monovalent six- to fourteen-membered, mono- or bi-carbocyclic ring, wherein the monocyclic ring is a aromatic and at least one of the rings in the bicyclic ring is aromatic. Representative examples include, but are not limited to, phenyl, biphenyl, naphthyl, indenyl and the like.

"Heteroaryl" means a monocyclic, fused bicyclic, or fused tricyclic, monovalent radical of 5 to 14 ring atoms containing one or more, for example one, two, three, or four ring heteroatoms independently selected from —O—, —S(O)n— (n is 0, 1, or 2), —N—, —N($R^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. $R^x$ is a hydrogen, alkyl, hydroxy, alkoxy, acyl, or alkylsulfonyl. A fused bicyclic radical includes bridged ring systems. Unless stated otherwise, the valency may be located on any atom of any ring of the heteroaryl group, valency rules permitting. In particular, when the point of valency is located on the nitrogen, $R^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isoxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Heterocycloalkyl" means a saturated or partially unsaturated monovalent monocyclic group of 3 to 9 ring atoms or a saturated or partially unsaturated monovalent fused bicyclic group of 5 to 12 ring atoms in which one or more, for example one, two, three, or four ring heteroatoms independently selected from —O—, —S(O)$_n$— (n is 0, 1, or 2), —N=, —N(R$^y$)— (where R$^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. A fused bicyclic radical includes bridged ring systems. Unless otherwise stated, the valency of the group may be located on any atom of any ring within the radical, valency rules permitting. In particular, when the point of valency is located on a nitrogen atom, Ry is absent. More specifically the term "heterocycloalkyl" includes, but is not limited to, piperidinyl, pyrimidinyl, morpholinyl, piperazinyl, azetidinyl, pyrrolidinyl, 2-oxopyrrolidinyl, 2,5-dihydro-1H-pyrrolyl, 4-piperidonyl, 2-oxopiperazinyl, tetrahydropyranyl, 2-oxopiperidinyl, thiomorpholinyl, thiamorpholinyl, perhydroazepinyl, pyrazolinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof and N-oxide or a protected derivative thereof.

As used herein, the term "pharaceutically acceptable salt" refers to a derivative of the disclosed compound wherein the parent compound is modified by making a pharaceutically acceptable acid or base salt thereof. Example of pharaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Suitable non-toxic acids include, but are not limited to, inorganic and organic acids such as acetic, alginic, anthranilic, benzenesulfonic, benzoic, camphorsulfonic, citric, enthenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Nonlimiting examples of salts of compounds of the invention include, but are not limited to, hydrochloride, hydrobromide, hydroiodide, sulfate, bisulfate, 2-hydroxyethanesulfonate, phosphate, hydrogen phosphate, acetate, adipate, alginate, aspartate, benzoate, butyrate, camphorate, comphorsulfonate, citrate, digluconate, glycerolphosphate, hemisulfate, heptanoatc, hexanoate, formate, succinate, malonate, fumarate, malcate, methanesulfonate, mesitylenesulfonate, naphthylenesulfonate, nicotinate, oxalte, pamoate, pectinate, persulfate, 3-phenylpropionate, picrate, pivalate, propionate, trichloroacetate, trifluoroacetate, glutamate, bicarbonate, undeconoate, lactate, citrate, tartrate, gluconate, benzene sulphonate, and p-toluenesulphonate salts.

As used herein, the term "geometric isomers" includes, but is not limited to, cis- and trans-forms; E- and Z-forms; c-, t-, and r-forms; endo- and exo-forms; R-, S-, and meso-forms; boat-, chair-, twist-, envelope-, and halfchair-forms; and combinations thereof.

As used herein, the term "enantiomers" refers to a pair of stereoisomers that are non-superimposable mirror images of each other. A 1:1 mixture of a pair of enantiomers is a racemic mixture. The term "enantiomers" is used to designate a racemic mixture where appropriate. "Diastereoisomers" are stereoisomers that have at least two asymmetric atoms, but which are not mirror-images of each other. The absolute stereochemistry may be specified according to the Cahn-Ingold-Prelog R-S system. When a compound is a pure enantiomer, the stereochemistry at each chiral carbon may be specified by either R or S. Resolved compounds can be designated as (+) or (−) depending on the direction (dextro- or levorotatory) at which they rotate plane polarized light at the wavelength of the sodium D line. Certain of the compounds described herein contain one or more asymmetric centers or axes and may thus give rise to enantiomers, diastereomers, and other stereoisomeric forms that may be defined, interms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be an E or Z configuration. If the compound contains a disubstituted cycloalkyl, the cycloalkyl substituent may have a cis- or trans-configuration.

As used herein, "prodrugs" are intended to include any covalently bonded carriers that release the active parent drug according to formula (I) through in vivo physiological action, such as hydrolysis, metabolism and the like, when such prodrug is administered to a subject. The suitability and techniques involved in making and using prodrugs are well known by a person of ordinary skill in the art. Prodrugs of the compounds of formula (I) (parent compounds) can be prepared by modifying functional groups present in the compounds in such a way that the modifications are cleaved, either at routine manipulation or in vivo, to the parent compounds. "Prodrugs" include the compounds of formula (I) wherein a hydroxy, amino, or sulfhydryl group is bonded to any group that, when the prodrugs are administered to a subject, cleaves to form a free hydroxyl, free amino, or free sulfhydryl group, respectively. Examples of prodrugs include, but are not limited to, derivatives and metabolites of the compounds of formula (I) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of the compounds of formula (I) with carboxyl functional groups are the lower alkyl (e.g., C1-C6) esters of the carboxylic acid. The carboxylate esters are conveniently formed by esterifying any of the carboxylic acid moieties present on the molecule.

As used herein, the term "solvate" means a compound or a pharmaceutically acceptable salt thereof, that further includes a stoichiometric or non-stoichiometric amount of a solvent bound by non-covalent intermolecular forces. If the solvent is water, the solvate may be conveniently referred to as a "hydrate," for example, a hemi-hydrate, a mono-hydrate, a sesqui-hydrate, a di-hydrate, a tri-hydrate, etc.

The term "coupling agent" refers to compounds which enable a coupling reaction. Examples of coupling agents include, but are not limited to, primary and secondary amines, thiols, thiolates, and thioethers, alcohols, alkoxide, azides, semicarbazides, and the like. Preferably, the coupling agent is N-hydroxysuccinimide (HOSu), 1-oxo-2-hydroxy-dihydrobenzotriazine (HODhbt), 1-hydroxybenzotriazole (HOBt), 7-aza-1-hydroxybenzotriazole (HOAt), N-hydroxytetrazole (Hot) ethyl 1-hydroxy-1H-1,2,3-triazole-4-carboxylate (HOCt), (benzotriazol-1-yloxy)tris(dimethylamino)phosphonium hexafluorophosphate (BOP), (benzotriazol-1-yloxy)tris(pyrrolidino) phosphonium hexafluorophosphate (PyBOP), and N-[(dimethylamino)-1H-1,2,3-triazolo[4,5-b]pyridin-1-ylmethylene -N-methyl-methanamimimum hexafluorophosphate N-oxide (N-HATU).

Compounds

The present invention provides a compound of formula (I):

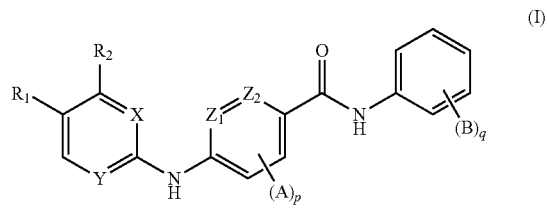

wherein:
X and Y are each independently N or CH, and at least one of X and Y is N;
$Z_1$ and $Z_2$ are each independently N or CH, and at least one of $Z_1$ and $Z_2$ is CH;
$R_1$ is $NH_2$, $OR_3$, $NHR_3$, $SR_3$ or $SOR_3$;
$R_2$ is alkyl, cycloalkyl, aryl, heteroaryl, or heterocycloalkyl, wherein the alkyl, cycloalkyl, aryl, heteroaryl, and heterocycloalkyl are optionally substituted with 1, 2, or 3 $R_4$;
$R_3$ is optionally substituted alkyl or cycloalkyl;
$R_4$ is halo, hydroxy, mercapto, cyano, nitro, amino, alkyl, alkoxy, alkylamino, dialkylamino, cycloalkyl, haloalkyl, haloalkoxy, aryl, heteroaryl, or heterocycloalkyl;
A and B are each independently hydrogen, halo, cyano, amino, alkyl, haloalkyl, alkoxy, haloalkoxy, cycloalkyl, halocycloalkyl, alkylaminoalkyl, alkylaminodialkyl, or alkyl-heterocycloalkyl, wherein the alkyl, alkoxy, cycloalkyl and heterocycloalkyl are optionally substituted;
p is 0, 1, 2, 3, or 4; and
q is 0, 1, 2, 3, or 4;

or a pharaceutically acceptable salt, geometric isomer, enantiomer, diastereomer, prodrug, or solvate thereof.

In an embodiment of the compound of formula (I), at least one of X and Y is N; both $Z_1$ $Z_2$ are CH, or one of $Z_1$ and $Z_2$ is N and the other is CH; $R_1$ is $NH_2$, $OR_3$, $NHR_3$, $SR_3$ or $SOR_3$; $R_3$ is optionally substituted alkyl; $R_2$ is aryl, heteroaryl, or heterocycloalkyl, which are optionally substituted with 1, 2, or 3 $R_4$; $R_4$ is halo, hydroxy, mercapto, cyano, nitro, amino, alkyl, alkoxy, alkylamino, dialkylamino, cycloalkyl, haloalkyl, or haloalkoxy: A is hydrogen, halo, cyano, amino, alkyl, haloalkyl, alkoxy, or haloalkoxy, wherien the alkyl and alkoxy are optionally substituted; B is hydrogen, halo, cyano, amino, alkyl, haloalkyl, alkoxy, haloalkoxy, alkylaminoalkyl, alkylaminodialkyl, or alkyl-heterocycloalkyl, wherein the alkyl and alkoxy are optionally substituted: p is 0, 1, or 2; and q is 0, 1, 2, or 3.

In another embodiment of the compound of formula (I), both X and Y are N, or X is CH and Y is N; both $Z_1$ $Z_2$ are CH, or $Z_1$ is N and $Z_2$ is CH; $R_1$ is $OR_3$, $SR_3$ or $SOR_3$: $R_3$ is optionally substituted alkyl; $R_2$ is aryl or heteroaryl, which is optionally substituted with 1, 2, or 3 $R_4$; is halo, cyano, alkyl, or haloalkoxy; A is hydrogen or halogen; B is cyano, halo, alkyl, haloalkyl, alkoxy, alkyl-heterocycloalkyl, or alkylaminodialkyl; p is 0 or 1; and q is 0, 1, or 2.

In yet another preferred embodiment, the present invention provides a compound selected from:

N-(2,6-Dimethyl-phenyl)-4-[5-methylsulfanyl-4-(4-trifluoromethoxy-phenyl)-pyrimidin-2-ylamino]-benzamide;
4-[4-(4-Cyano-phenyl)-5-methylsulfanyl-pyrimidin-2-ylamino]-N-(2,6-dimethyl-phenyl) -benzamide;
4-[4-(4-Cyano-phenyl)-5-methylsulfanyl-pyrimidin-2-ylamino]-N-phenyl-benzamide;
N-(3-Chloro-4-trifluoromethyl-phenyl)-4-[4-(4-cyano-phenyl)-5-methylsulfanyl-pyrimidin-2-ylamino]-benzamide;
4-[4-(2-Fluoro-pyridin-3-yl)-5-methylsulfanyl-pyrimidin-2-ylamino]-N-phenyl-benzamide;
N-(2,6-Dimethyl-phenyl)-4-[4-(2-fluoro-pyridin-3-yl)-5-methylsulfanyl-pyrimidin-2-ylamino]-benzamide;
N-(4-Chloro-3-trifluoromethyl-phenyl)-4-[4-(6-ethoxy-pyridin-3-yl)-5-methylsulfanyl-pyrimidin -2-ylamino]-benzamide;
N-(2,6-Difluoro-phenyl)-4-[4-(2-fluoro-pyridin-3-yl)-5-methylsulfanyl-pyrimidin-2-ylamino]-benzamide;
N-(2,6-Dimethoxy-phenyl)-4-[4-(2-fluoro-pyridin-3-yl)-5-methylsulfanyl-pyrimidin-2-ylamino]-benzamide;
N-(2,6-Difluoro-phenyl)-4-(5-methylsulfanyl-4-pyridin-3-yl-pyrimidin-2-ylamino)-benzamide;
4-[4-(2-Fluoro-pyridin-3-yl)-5-methylsulfanyl-pyrimidin-2-ylamino]-N-o-tolyl-benzamide;
N-(2,6-Dimethyl-phenyl)-3-fluoro-4-[4-(2-fluoro-pyridin-3-yl)-5-methylsulfanyl-pyrimidin-2-ylamino]-benzamide;
N-(2,6-Dimethoxy-phenyl)-3-fluoro-4-[4-(2-fluoro-pyridin-3-yl)-5-methylsulfanyl-pyrimidin -2-ylamino]-benzamide;
4-[4-(2-Fluoro-pyridin-3-yl)-5-methylsulfanyl-pyrimidin-2-ylamino]-N-(2-methoxy-6-methyl -phenyl)-benzamide;
3-Fluoro-4-[4-(2-fluoro-pyridin-3-yl)-5-methylsulfanyl-pyrimidin-2-ylamino]-N-(2-methoxy -6-methyl-phenyl)-benzamide;
3-Fluoro-4-[4-(2-fluoro-pyridin-3-yl)-5-methylsulfanyl-pyrimidin-2-ylamino]-N-o-tolyl-benzamide;
3-Fluoro-4-[4-(6-fluoro-pyridin-3-yl)-5-methylsulfanyl-pyrimidin-2-ylamino]-N-(2-methoxy -6-methyl-phenyl)-benzamide;
N-(4-Cyano-phenyl)-4-[4-(2-fluoro-pyridin-3-yl)-5-methylsulfanyl-pyrimidin-2-ylamino]-benzamide;
4-(5-Methylsulfanyl-4-phenyl-pyrimidin-2-ylamino)-N-o-tolyl-benzamide;

N-(2-Methyl-5-morpholin-4-ylmethyl-phenyl)-4-(5-methylsulfanyl-4-phenyl-pyrimidin-2-ylamino)-benzamide;
N-(2,6-Dimethoxy-phenyl)-4-(5-methylsulfanyl-4-phenyl-pyrimidin-2-ylamino)-benzamide;
N-(2,6-Dimethoxy-phenyl)-4-[5-methylsulfanyl-4-(4-trifluoromethoxy-phenyl)-pyrimidin-2-ylamino]-benzamide;
4-[5-Methylsulfanyl-4-(4-trifluoromethoxy-phenyl)-pyrimidin-2-ylamino]-N-o-tolyl-benzamide;
N-(2-Methyl-5-morpholin-4-ylmethyl-phenyl)-4-[5-methylsulfanyl-4-(4-trifluoromethoxy-phenyl)-pyrimidin-2-ylamino]-benzamide;
N-(2-Methoxy-6-methyl-phenyl)-4-[5-methylsulfanyl-4-(4-trifluoromethoxy-phenyl)-pyrimidin-2-ylamino]-benzamide;
N-(2-Methyl-5-morpholin-4-ylmethyl-phenyl)-4-(5-methylsulfanyl-4-pyridin-4-yl-pyrimidin-2-ylamino)-benzamide;
N-(2-Methyl-5-morpholin-4-ylmethyl-phenyl)-4-[5-methylsulfanyl-4-(4-trifluoromethyl-phenyl)-pyrimidin-2-ylamino]-benzamide;
N-(2-Methyl-5-piperidin-1-ylmethyl-phenyl)-4-[5-methylsulfanyl-4-(4-trifluoromethyl-phenyl)-pyrimidin-2-ylamino]-benzamide;
N-(2,6-Dimethyl-phenyl)-4-[4-(4-fluoro-phenyl)-5-methylsulfanyl-pyrimidin-2-ylamino]-benzamide;
4-[4-(4-Fluoro-phenyl)-5-methylsulfanyl-pyrimidin-2-ylamino]-N-(2-methyl-5-morpholin-4-ylmethyl-phenyl)-benzamide;
N-(5-Dimethylaminomethyl-2-methyl-phenyl)-4-[4-(4-fluoro-phenyl)-5-methylsulfanyl-pyrimidin-2-ylamino]-benzamide;
N-(5-Dimethylaminomethyl-2-methyl-phenyl)-4-[5-methylsulfanyl-4-(4-trifluoromethyl-phenyl)-pyrimidin-2-ylamino]-benzamide;
4-[4-(4-Cyano-phenyl)-5-methylsulfanyl-pyrimidin-2-ylamino]-N-(2-methyl-5-morpholin-4-ylmethyl-phenyl)-benzamide;
4-[4-(4-Cyano-phenyl)-5-methylsulfanyl-pyrimidin-2-ylamino]-N-(5-dimethylaminomethyl-2-methyl-phenyl)-benzamide;
4-[4-(4-Cyano-phenyl)-5-methylsulfanyl-pyrimidin-2-ylamino]-N-[2-methyl-5-(4-methyl-piperazin-1-ylmethyl)-phenyl]-benzamide;
4-[4-(4-Fluoro-phenyl)-5-methylsulfanyl-pyrimidin-2-ylamino]-N-[2-methyl-5-(4-methyl-piperazin-1-ylmethyl)-phenyl]-benzamide;
N-[2-Methyl-5-(4-methyl-piperazin-1-ylmethyl)-phenyl]-4-[5-methylsulfanyl-4-(4-trifluoromethoxy-phenyl)-pyrimidin-2-ylamino]-benzamide;
4-[5-Methoxy-4-(4-trifluoromethoxy-phenyl)-pyrimidin-2-ylamino]-N-(2-methyl-5-morpholin-4-ylmethyl-phenyl)-benzamide;
N-(2-Methyl-5-morpholin-4-ylmethyl-phenyl)-4-[4-(1-methyl-1H-pyrazol-4-yl)-5-methylsulfanyl-pyrimidin-2-ylamino]-benzamide;
3-Fluoro-N-(2-methyl-5-morpholin-4-ylmethyl-phenyl)-4-[5-methylsulfanyl-4-(4-trifluoromethoxy-phenyl)-pyrimidin-2-ylamino]-benzamide;
3-Fluoro-4-[4-(4-fluoro-phenyl)-5-methylsulfanyl-pyrimidin-2-ylamino]-N-(2-methyl-5-morpholin-4-ylmethyl-phenyl)-benzamide;
3-Fluoro-4-[4-(4-fluoro-phenyl)-5-methylsulfanyl-pyrimidin-2-ylamino]-N-(2-methyl-5-piperidin-1-ylmethyl-phenyl)-benzamide;
4-[4-(4-Fluoro-phenyl)-5-methylsulfanyl-pyrimidin-2-ylamino]-N-(3-morpholin-4-ylmethyl-phenyl)-benzamide;
3-Fluoro-4-[5-methylsulfanyl-4-(4-trifluoromethoxy-phenyl)-pyrimidin-2-ylamino]-N-(3-morpholin-4-ylmethyl-phenyl)-benzamide;
3-Fluoro-N-(2-methyl-5-morpholin-4-ylmethyl-phenyl)-4-[4-(1-methyl-1H-pyrazol-4-yl)-5-methylsulfanyl-pyrimidin-2-ylamino]-benzamide;
3-Fluoro-N-[2-methyl-5-(4-methyl-piperazin-1-ylmethyl)-phenyl]-4-[4-(1-methyl-1H-pyrazol-4-yl)-5-methylsulfanyl-pyrimidin-2-ylamino]-benzamide;
N-(5-Diethylaminomethyl-2-methyl-phenyl)-4-[4-(4-fluoro-phenyl)-5-methylsulfanyl-pyrimidin-2-ylamino]-benzamide;
4-[4-(4-Fluoro-phenyl)-5-methylsulfanyl-pyrimidin-2-ylamino]-N-(2-methyl-5-piperidin-1-ylmethyl-phenyl)-benzamide;
4-[4-(4-Cyano-phenyl)-5-methoxy-pyrimidin-2-ylamino]-N-(2-methyl-5-morpholin-4-ylmethyl-phenyl)-benzamide;
4-[4-(4-Cyano-phenyl)-5-methoxy-pyrimidin-2-ylamino]-N-(5-diethylaminomethyl-2-methyl-phenyl)-benzamide;
4-[4-(4-Cyano-phenyl)-5-methoxy-pyrimidin-2-ylamino]-N-[2-methyl-5-(4-methyl-piperazin-1-ylmethyl)-phenyl]-benzamide;
4-[5-Methoxy-4-(4-trifluoromethoxy-phenyl)-pyrimidin-2-ylamino]-N-[2-methyl-5-(4-methyl-piperazin-1-ylmethyl)-phenyl]-benzamide;
N-(5-Diethylaminomethyl-2-methyl-phenyl)-3-fluoro-4-[4-(4-fluoro-phenyl)-5-methylsulfanyl-pyrimidin-2-ylamine]-benzamide;
N-(5-Dimethylaminomethyl-2-methyl-phenyl)-4-[5-methylsulfanyl-4-(4-trifluoromethoxy-phenyl)-pyrimidin-2-ylamino]-benzamide;
3-Fluoro-N-(2-fluoro-5-morpholin-4-ylmethyl-phenyl)-4-[5-methylsulfanyl-4-(4-trifluoromethoxy-phenyl)-pyrimidin-2-ylamino]-benzamide;
N-(3-Diethylaminomethyl-phenyl)-3-fluoro-4-[5-methylsulfanyl-4-(4-trifluoromethoxy-phenyl)-pyrimidin-2-ylamino]-benzamide;
3-Fluoro-N-(2-fluoro-5-morpholin-4-ylmethyl-phenyl)-4-[4-(4-fluoro-phenyl)-5-methylsulfanyl-pyrimidin-2-ylamino]-benzamide;
3-Fluoro-N-(2-methoxy-5-morpholin-4-ylmethyl-phenyl)-4-[5-methylsulfanyl-4-(4-trifluoromethoxy-phenyl)-pyrimidin-2-ylamino]-benzamide;
4-[4-(4-Fluoro-phenyl)-5-methylsulfanyl-pyrimidin-2-ylamino]-N-(2-methoxy-5-morpholin-4-ylmethyl-phenyl)-benzamide;
3-Fluoro-4-[4-(4-fluoro-phenyl)-5-methoxy-pyrimidin-2-ylamino]-N-(2-methyl-5-morpholin-4-ylmethyl-phenyl)-benzamide;
N-(5-Diethylaminomethyl-2-methyl-phenyl)-3-fluoro-4-[5-methoxy-4-(4-trifluoromethoxy-phenyl)-pyrimidin-2-ylamino]-benzamide;
3-Fluoro-4-[5-methoxy-4-(4-trifluoromethoxy-phenyl)-pyrimidin-2-ylamino]-N-[2-methyl-5-(4-methyl-piperazin-1-ylmethyl)-phenyl]-benzamide;
N-(2-Methyl-5-morpholin-4-ylmethyl-phenyl)-6-[5-methylsulfanyl-4-(4-trifluoromethoxy-phenyl)-pyrimidin-2-ylamino]-nicotinamide;
6-[5-Methylsulfanyl-4-(4-trifluoromethoxy-phenyl)-pyrimidin-2-ylamino]-N-(3-morpholin-4-ylmethyl-phenyl)-nicotinamide;
4-[5-Methylsulfanyl-4-(4-trifluoromethoxy-phenyl)-pyrimidin-2-ylamino]-N-(3-morpholin-4-ylmethyl-phenyl)-benzamide;
N-(5-Diethylaminomethyl-2-methyl-phenyl)-6-[5-methylsulfanyl-4-(4-trifluoromethoxy-phenyl)-pyrimidin-2-ylamino]-nicotinamide;

4-[4-(6-Fluoro-pyridin-3-yl)-5-methylsulfanyl-pyrimidin-2-ylamino]-N-(2-methyl-5-morpholin -4-ylmethyl-phenyl)-benzamide;

N-(2-Methyl-5-morpholin-4-ylmethyl-phenyl)-4-[5-methylsulfanyl-4-(6-trifluoromethyl-pyridin -3-yl)-pyrimidin-2-ylamino]-benzamide;

4-[5-Methylsulfanyl-4-(6-trifluoromethyl-pyridin-3-yl)-pyrimidin-2-ylamino]-N-(3-morpholin -4-ylmethyl-phenyl)-benzamide;

N-(2-Fluoro-5-morpholin-4-ylmethyl-phenyl)-4-[5-methylsulfanyl-4-(4-trifluoromethoxy-phenyl) -pyrimidin-2-ylamino]-benzamide;

N-(2-Fluoro-5-morpholin-4-ylmethyl-phenyl)-4-[4-(4-fluoro-phenyl)-5-methylsulfanyl-pyrimidin -2-ylamino]-benzamide;

4-[5-Ethoxy-4-(4-trifluoromethoxy-phenyl)-pyrimidin-2-ylamino]-N-(2-methyl-5-morpholin -4-ylmethyl-phenyl)-benzamide;

4-[5-Ethoxy-4-(4-trifluoromethoxy-phenyl)-pyrimidin-2-ylamino]-N-[2-methyl-5-(4-methyl-piperazin -1-ylmethyl)-phenyl]-benzamide;

N-(5-Diethylaminomethyl-2-methyl-phenyl)-4-[5-ethoxy-4-(4-trifluoromethoxy-phenyl)-pyrimidin -2-ylamino]-benzamide;

4-[5-Ethoxy-4-(4-fluoro-phenyl)-pyrimidin-2-ylamino]-N-(2-methyl-5-morpholin-4-ylmethyl -phenyl)-benzamide;

4-[5-Ethoxy-4-(4-fluoro-phenyl)-pyrimidin-2-ylamino]-N-[2-methyl-5-(4-methyl-piperazin-1-ylmethyl)-phenyl]-benzamide;

N-(5-Diethylaminomethyl-2-methyl-phenyl)-4-[5-ethoxy-4-(4-fluoro-phenyl)-pyrimidin-2-ylamino]-benzamide;

3-Fluoro-4-[4-(4-fluoro-phenyl)-5-methylsulfanyl-pyrimidin-2-ylamino]-N-(2-methyl-5-piperazin -1-ylmethyl-phenyl)-benzamide;

4-[4-(4-Fluoro-phenyl)-5-methoxy-pyrimidin-2-ylamino]-N-(2-methyl-5-piperazin-1-ylmethyl -phenyl)-benzamide;

3-Fluoro-4-[4-(4-fluoro-phenyl)-5-methoxy-pyrimidin-2-ylamino]-N-(2-methyl-5-piperazin-1-ylmethyl-phenyl)-benzamide;

N-(2-Methyl-5-morpholin-4-ylmethyl-phenyl)-4-[5-methylsulfanyl-4-(4-trifluoromethoxy-phenyl) -pyridin-2-ylamino]-benzamide;

N-[2-Methyl-5-(4-methyl-piperazin-1-ylmethyl)-phenyl]-4-[5-methylsulfanyl-4-(4-trifluoromethoxy -phenyl)-pyridin-2-ylamino]-benzamide;

N-(5-Dimethylaminomethyl-2-methyl-phenyl)-4-[5-methylsulfanyl-4-(4-trifluoromethoxy-phenyl) -pyridin-2-ylamino]-benzamide;

4-((4-(4-fluorophenyl)-5-(methylthio)pyridin-2-yl)amino)-N-(2-methyl-5-(morpholinomethyl) phenyl)benzamide;

N-(2-methyl-5-(morpholinomethyl)phenyl)-4-((5-(methylsulfinyl)-4-(4-(trifluoromethoxy)phenyl) pyrimidin-2-yl)amino)benzamide;

N-(2-methyl-5-(morpholinomethyl)phenyl)-4-((5-(methylthio)-6-(4-(trifluoromethoxy)phenyl) pyridin-2-yl)amino)benzamide;

N-(5-((diethylamino)methyl)-2-methylphenyl)-4-((5-(methylthio)-4-(4-(trifluoromethoxy)phenyl) pyridin-2-yl)amino)benzamide;

4-((5-amino-4-(4-(trifluoromethoxy)phenyl)pyrimidin-2-yl)amino)-N-(2-methyl-5-(morpholinomethyl) phenyl)benzamide;

4-((4-(4-fluorophenyl)-5-(methylthio)pyridin-2-yl)amino)-N-(2-methyl-5-((4-methylpiperazin -1-yl)methyl)phenyl)benzamide;

N-(2-methyl-5-((4-methylpiperazin-1-yl)methyl)phenyl)-4-((5-(methylthio)-4-(4-(trifluoromethyl)phenyl)pyridin -2-yl)amino)benzamide; and N-(2-methyl-5-(morpholinomethyl)phenyl)-4-((5-(methylamino)-4-(4-(trifluoromethoxy)phenyl)pyrimidin -2-yl)amino)benzamide;

or a pharmaceutically acceptable salt, geometric isomer, enantiomer, diastereomer, prodrug, or solvate thereof.

Pharmaceutical Compositions, Use and Methods

The compounds of the present invention can be therapeutically administered as the neat chemical, but it may be useful to administer the compounds as a pharmaceutical composition or formulation. Thus, the present invention provides a pharmaceutical composition comprising a therapeutically effective amount of a compound of formula (I) or a pharmaceutically acceptable salt, geometric isomer, enantiomer, diastereomer, prodrug, or solvate thereof, and one or more pharmaceutically acceptable carriers or excipients.

The pharmaceutical compositions can be administered in a variety of dosage forms including, but not nmited to, a solid dosage form or a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension, or combinations thereof. The compounds can be administered, for example, by oral or parenteral routes, including intravenous, intramuscular, intraperitoneal, subcutaneous, transdermal, airway (aerosol), rectal, vaginal and topical (including buccal and sublingual) administration.

In one embodiment of the invention, the compound of formula (I) is administered orally. For oral administration, the compounds will generally be provided in unit dosage form of a tablet, pill, dragee, lozenge or capsule; as a powder or granules; or as an aqueous solution, suspension, liquid, gel, syrup, slurry, etc. suitable for ingestion by the subject. The dosage form can be a controlled release dosage form formulated as a tablet or a caplet. Tablets for oral use may include the active ingredients mixed with one or more pharmaceutically acceptable excipients.

An "excipient" generally refers to a substance, often an inert substance, added to a pharmacological composition or otherwise used as a vehicle to further facilitate administration of a compound. Examples of excipients include, but are not limited to, inert diluents, disintegrating agents, binding agents, lubricating agents, sweetening agents, flavoring agents, coloring agents, preservatives, effervescent mixtures, and adsorbents. Suitable inert diluents include, but are not limited to, sodium and calcium carbonate, sodium and calcium phosphate, lactose, and the like. Suitable disintegrating agents include, but are not limited to, starches, such as corn starch, cross-linked polyvinyl pyrrolidone, agar, alginic acid, or a salt thereof, such as sodium alginate, and the like. Binding agents may include, but are not limited to, magnesium aluminum silicate, starches such as corn, wheat or rice starch, gelatin, methylcellulose, sodium carboxymethylcellulose, polyvinylpyrrolidone, and the like. A lubricating agent, if present, will generally be magnesium stearate and calcium stearate, stearic acid, talc, or hydrogenated vegetable oils. If desired, the tablet may be coated with a material such as glyceryl monostearate or glyceryl distearate, to delay absorption in the gastrointestinal tract. The compositions can also be formulated as chewable tablets, for example, by using substances such as mannitol in the formulation.

Pharmaceutical compositions for oral use can be obtained through combination of the compound formula (I) with a solid excipient, optionally grinding the resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethyl-cellulose or sodium carboxymethyl-cellulose: and gums including arabic and tragacanth; as we as proteins such as gelatin and collagen.

Capsules for oral use include hard gelatin capsules in which the active ingredient is mixed with a solid diluent, and soft gelatin capsules wherein the active ingredient is mixed with wate or an oil such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The pharmaceutical compositions also may comprise suitable solid or gel phase carriers. Examples of such carriers include, but are not limited to, calcium carbonate, calcium phosphate, various sugars, starches, cellulose derivatives, gelatin, and polymers such as polyethylene glycols.

Compounds and pharmaceutical compositions suitable for use in the present invention include those wherein the active ingredient is administered in an effective amount to achieve its intended purpose. The term "therapeutically effective amount" refers to the situation wherein the amount of the compound of formula (I) or pharmaceutically acceptable salts, geometric isomers, enantiomers, diastercomers, prodrugs, or solvates thereof, alone or in combination with ionizing radiation or an anticancer agent which, upon single or multiple dose administration to the subject, provides the desired effect in the subject under treatment. Toxicity and therapeutic efficacy of such compounds can be determined by standard pharmaceutical procedures in cell cultures or experimental animals, e.g., for determining the $IC_{50}$ values. As used herein, "$IC_{50}$" refers to the concentration of an agent which produces 50% of the maximal inhibitory response possible for that agent.

The amount of the compound of formula (I) actually administered will be determined by a physician under the relevant circumstances, including the condition to be treated, the size and the type of neoplasia, the chosen route of administration, the actual compound of the present invention administered, the timing of the administration of the Hedgehog pathway modulator relative to the other therapies, the type, species, age, weight, sex and medical condition of the subject, the renal and hepatic function of the subject, and the severity of the subject's symptoms. Optimal precision in achieving concentration of drug within the range that yields efficacy requires a regimen based on the kinetics of the drug's availability to target sites. This involves consideration of the distribution, equilibrium, and elimination of a drug. In some instances, dosage levels below the lower limit of the aforesaid range may be more than adequate, while in the other cases still larger doses may be employed.

"In vivo" means within a living subject, as within an animal or human. In this context, agents can be used therapeutically in vivo to retard or elminate the proliferation of aberrantly replicating cells. The agents also can be used in vivo as a prophylactic to prevent aberrant cell proliferation or the manifestation of symptoms associated therewith.

"Ex vivo" means outside a living subject. Examples of ex vivo cell populations include cell cultures and biological samples, such as fluid or tissue samples from humans or animals. Such samples can be obtained by methods well known in the art. Exemplary biological fluid samples include blood, cerebrospinal fluid, urine, and saliva. Exemplary tissue samples include tumors and biopsies thereof. In this context, the present compounds can be employed in numerous applications, both therapeutic and experimental.

The present invention also relates to the use of the compound of formula (I) or a pharmaceutically acceptable salt, geometric isomer, enantiomer, diastereomer, prodrug, or solvate thereof, in the manufacture of a medicament modulating the Hedgehog pathway.

Furthermore, the present invention relates to a method for treating cancer in a subject in need thereof comprising adininistering a therapeutically effective amount of a compound of formula (I) or a pharmaceutically acceptable salt, geometric isomer, enantiomer, diastereomer, prodrug, or solvate thereof to the subject.

"Cancer" refers to cellular-proliferative disease states, including but not limited to: Cardiac cancers, such as sarcoma (e.g., angiosarcoma, fibrosarcoma, rhabdomyosarcoma, and liposarcoma), myxoma, rhabdomyoma, fibroma, lipoma and teratoma; Lung cancers, such as bronchogenic carcinoma (e.g., squamous cell carcinoma, undifferentiated small cell carcinoma, undifferentiated large cell carcinoma, and adenocarcinoma carcinoma), alvcolar carcinoma (e.g., bronchiolar carcinoma), bronchial adenoma, sarcoma, lymphoma, chondromatous hanlartoma, and inesothelioma; Gastronintestinal cancers, such as esophagus carcinoma (e.g., squamous cell carcinoma, adenocarcinoma, leiomyosarcoma, and lymphoma), stomach carcinoma (e.g., carcinoma, lymphoma, and leiomyosarcoma), pancreas carcinoma (e.g., ductal adenocarcinoma, insulinoma, glucagonoma, gastrinoma, carcinoid tumors, and vipoma), small bowel carcinoma (e.g., adenocarcinoma, lymphoma, carcinoid tumors, Karposi's sarcoma, leiomyoma, hemangioma, lipoma, neurofibroma, and fibroma), large bowel carcinoma (e.g., adenocarcinoma, tubular adenoma, villous adenoma, hamartoma, and leiomyoma); Genitourinary tract cancers, such as kidney carcinoma (e.g., adenocarcinoma, Wilm's tumor [nephroblastoma], lymphoma, and leukemia), bladder and urethra carcinoma (e.g., squamous cell carcinoma, transitional cell carcinoma, and adenocarcinoma), prostate carcinoma (e.g., adenocarcinoma, and sarcoma), testis carcinoma (e.g., seminoma, teratoma, embryonal carcinoma, teratocarcinoma, choriocarcinoma, sarcoma, interstitial cell carcinoma, fibroma, fibroadenoma, adenomatoid tumors, and lipoma); Liver cancers, such as hepatoma (e.g., hepatocellular carcinoma), cholangiocarcinoma, hepatoblastoma, angiosarcoma, hepatocellular adenoma, and hemangioma; Bone caners, such as osteogenic sarcoma (e.g., osteosarcoma), fibrosarcoma, malignant fibrous histiocytoma, chondrosarcoma, Ewing's sarcoma, malignant lymphoma (e.g., reticulum cell sarcoma), multiple mycloma, malignant giant cell tumor chordoma, osteochronfroma (e.g., osteocartilaginous exostoses), benign chondroma, chondroblastoma, chondromyxofibroma, osteoid osteoma, and giant cell tumors; Nervous system cancers, such as skull carcinoma (e.g., osteoma, hemangioma, granuloma, xanthoma, and osteitis deformans), meninx carcinoma (e.g., meningioma, meningiosarcoma, and gliomatosis), brain carcinoma (e.g., astrocytoma, medulloblastoma, glioma, ependymoma, germinoma (pineal oma), glioblastoma multiform, oligodendroglioma, schwannoma, retinoblastoma, and congenital tumors), spinal cord neurofibroma, meningioma, glioma, and sarcoma: Gynecological cancers, such as uterus carcinoma (e.g., endometrial carcinoma), cervix carcinoma (e.g., cervical carcinoma, and pre-tumor cervical dysplasia), ovary carcinoma (e.g., ovarian carcinoma [e.g., serous cystadenocarcinoma, mucinous cystadenocarcinoma, and unclassified carcinoma], granulosa-thecal cell tumors, Sertoli-Leydig cell tumors, dysgerminoma, and malignant teratoma), vulva carcinoma (e.g., squamous cell carcinoma, intraepithelial carcinoma, adenocarcinoma, fibrosarcoma, and melanoma), vagina carcinoma (e.g., clear cell carcinoma, squamous cell carcinoma, botryoid sarcoma (e.g., embryonal rhabdomyosarcoma], and fallopian tub carcinoma); Hematologic cancers, such as blood carcinoma (myeloid leukemia [acute and chronic], acute lymphoblastic leukemia, chronic lymphocytic leukemia, myeloproliferative diseases, multiple myeloma, and myelodysplastic syndrome), Hodgkin's disease, non-Hodgkin's lymphoma [malignant lymphoma]; Skin cancers, such as malignant melanoma, basal cell carcinoma, squamous cell carcinoma, Karposi's sarcoma, moles dysplastic nevi, lipoma, angioma, dermatofibroma, keloids, psoriasis; Adrenal Gland caners, such as neuroblastoma; or breast cancer.

The compounds of formula (I) can be administered as the sole active agent, or in combination with other known cancer treatments.

The term "in combination with" means that the compound of formula (I) may be administered shortly before, shortly after, concurrently, or any combination of before, after, or concurrently, with one or more other anti-neoplasm therapies. Thus, the compound of formula (I) and a second anticancer agent may be administered simultaneously either as a single composition or as two separate compositions or sequentially as two separate compositions. Likewise, the compound of formula (I) and a chemotherapy or ionizing radiation therapy may be administered simultaneously, separately or sequentially. One skilled in the art will recognize that the amount of the compound of formula (I) to be administered in combination with anticancer therapies is preferably that amount sufficient to enhance the effect of the anticancer therapies or that amount sufficient to induce apoptosis or cell death along with the anticancer therapies and/or to maintain an antiangiogenic effect.

The term "second anticancer agent" as used herein, unless otherwise indicated, refers to an agent capable of inhibiting or preventing the growth of neoplasms, or checking the maturation and proliferation of malignant (cancer) cells. Second anticancer agents suitable for use in combination with the compounds of formula (I) include, but are not limited to targeted cancer drugs, such as trastuzumab, ramucirumab, bevacizumab, everolimus, tamoxifen, toremifene, fulvestrant, anastrozole, exemestane, lapatinib, letrozole, pertuzumab, ado-trastuzumab emtansine, palbociclib, cetuximab, panitumumab, ziv-aflibercept, regorafenib, lmatinib mesylate, lanreotide acetate, sunitinib, regorafenib, denosumab, alitretinoin, sorafenib, pazopanib, temsirolimus, everolimus, tretinoin, dasatinib, nilotinib, bosutinib, rituximab, alemtuzumab, ofatumumab, obinutuxumab, ibrutinib, idelalisib, blinatumomab, soragenib, crizotinib, erlotinib, gefitinib, afatinib dimaleate, ceritnib, ramucinumab, uivolumab, pembrolizumab, osimertinib, and necitumumab; an alkylating agent, such as busulfan, chlorambucil, cyclophosphamide, iphosphamide, melphalan, nitrogen mustard, streptozocin, thiotepa, uracil nitrogen mustard, triethylenemelamine, temozolomide, and 2-chloroethyl-3-sarcosinamide-1-nitrosourea (SarCNU); an antibiotic or plant alkaloid, such as actinomycin-D, bleomycin, cryptophycins, daunorubicin, doxorubicin, idarubicin, irinotecan, L-asparaginase, mitomycin-C, mitramycin, navelbine, paclitaxel, docetaxel, topotecan, vinblastine, vincristine, teniposide (VM-26), and etoposide (VP-16); a hormone or steroid, such as 5α-reductase inhibitor, aminoglutethimide, anastrozole, bicalutamide, chlorotrianisene, diethylstilbestrol (DES), dromostanolone, estramustine, ethinyl estradiol, flutamide, fluoxymesterone, goserelin, hydroxyprogesterone, letrozole, leuprolide, medroxyprogesterone acetate, megestrol acetate, methyl prednisolone, methyltestosterone, mitotane, nilutamide, prednisolone, arzoxifene (SERM-3), tamoxifen, testolactone, testosterone, triamicnolone, and zoladex; a synthetic, such as all-trans retinoic acid, carmustine (BCNU), carboplatin (CBDCA), lomustine (CCNU), cis-diaminedichloroplatinum (cisplatin), dacarbazine, gliadel, hexamethylmelamine, hydroxyurea, levamisole, mitoxantrone, o,p'-dichlorodiphenyldichloroethane (o,p'-DDD) (also known as lysodren or mitotane), oxaliplatin, porfimer sodium, procarbazine, and imatinib mesylate (Gleevec®); an antimetabolite, such as chlorodeoxyadenosine, cytosine arabinoside, 2'-deoxycoformycin, fludarabine phosphate, 5-fluorouracil (5-FU), 5-fluoro-2'-deoxyuridine (5-FUdR), gemcitabine, camptothecin, 6-mereaptopurine, methotrexate, 4-methylthioamphetaminc (4-MTA), and thioguanine; and a bilogic, such as alpha interferon, BCG (Bacillus Calmette-Guerin), granulocyte colony stimulating factor (G-CSF), granulocyte-macrophage colony-stimulating factor (GM-CSF), interleukin-2, and herceptin.

The term "treating," as used herein, unless otherwise indicated, means reersing, alleviating, inhibiting the process of, or preventing the disorder or condition to which such term applies, or one or more symptoms of such disorder or condition. The term "treatment," as used herein, unless otherwise indicated, refers to the act of treating as "treating" is defined immediately above.

Compound Synthesis

The invention also relates to a method for preparing the compound of formula (I) or pharmaceutically acceptable salts, geometric isomers, enantiomers, distereomers, prodrugs, or solvates thereof. The compounds of the present invention can be made by one skilled in the art using conventional organic synthesis and commercially available materials.

In one embodiment, the method for preparing the compound of formula (I) or a pharmaceutically acceptable salt, geometric isomer, enantiomer, diastereomer, prodrug, or solvate thereof comprises:
a. reacting a compound of formula (1)

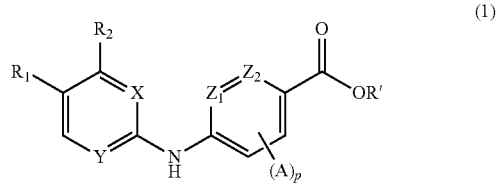

wherein $R_1$, $R_2$, X, Y, $Z_1$, $Z_2$, A, and p are as defined herein; and R' is alkyl, with a base to obtain a compound of formula (2)

(2)

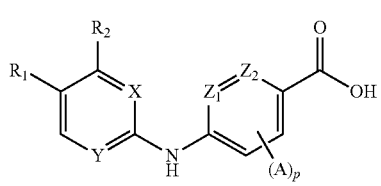

wherein $R_1$, $R_2$, X, Y, $Z_1$, $Z_2$, A, and p are as defined herein; and reacting the compound of formula (2) with a compound of formula (3)

(3)

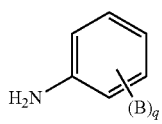

wherein B and q are as defined herein, in the presence of a coupling agent and a solvent to obtain the compound of formula (1).

By way of example and not limitation, the compound of formula (I) or a pharmaceutically acceptable salt, geometric isomer, enantiomer, diastereomer, prodrug, or solvate thereof can be prepared as outlined in Schemes 1 to 3 shown below. A compound of formula (3) can be prepared as outlined in Scheme 4 below or directly obtained from commercial sources. It should be noted that one skilled in the art can modify the procedures set forth in the illustrative schemes and examples to arrive at the desired product.

Scheme 1

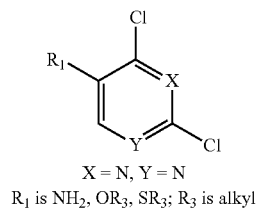

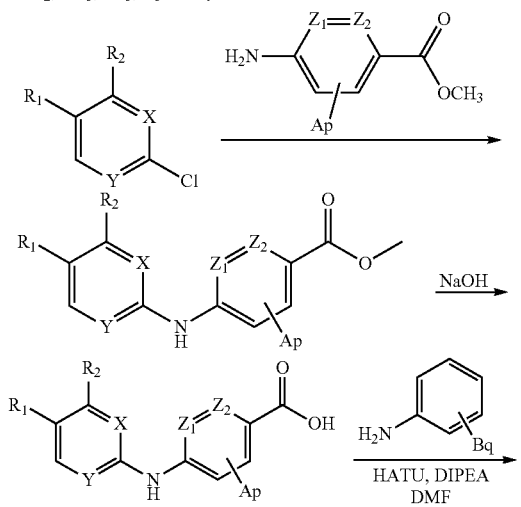

Scheme 2

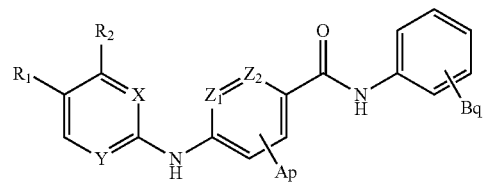

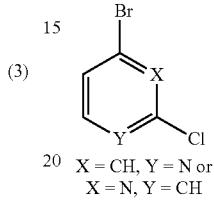

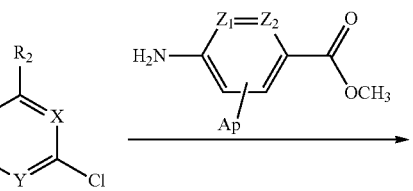

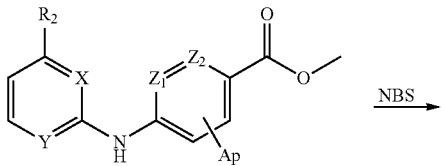

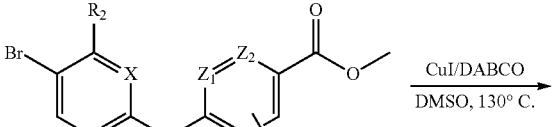

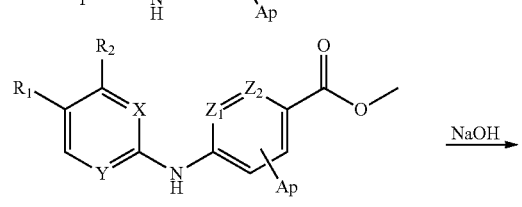

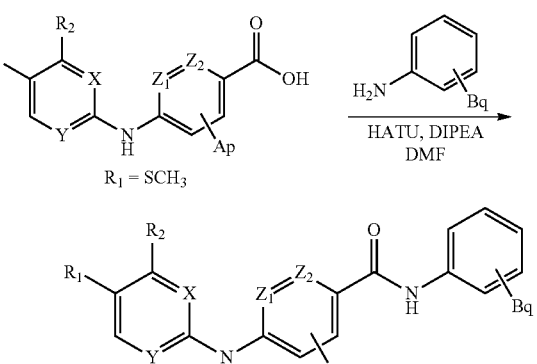

Scheme 3

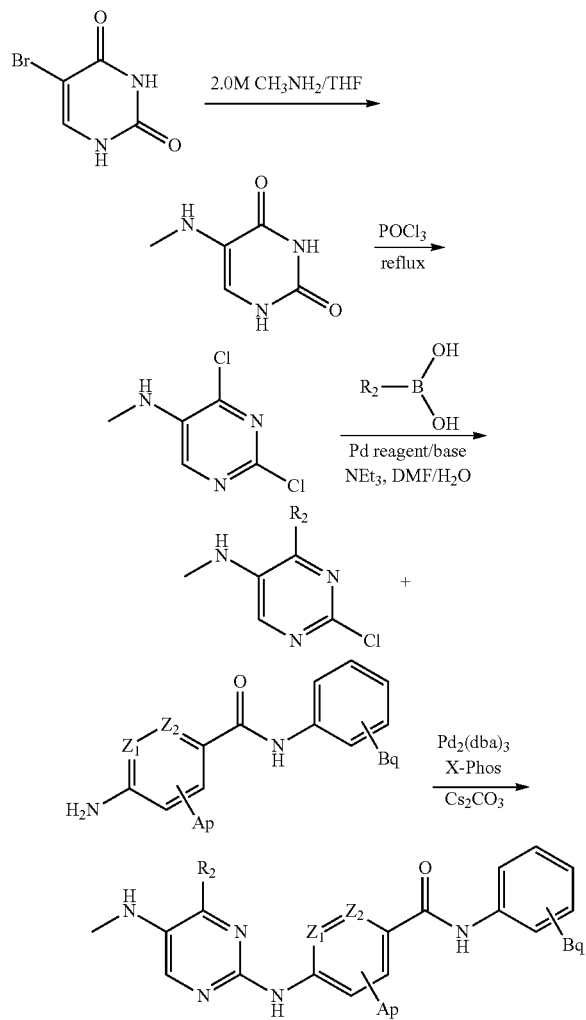

Scheme 4

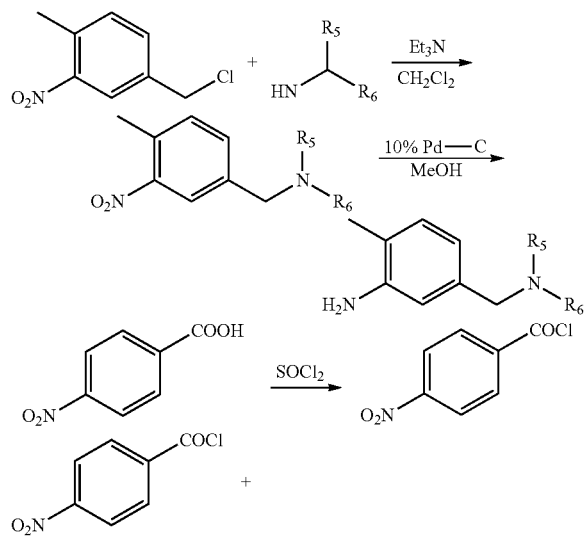

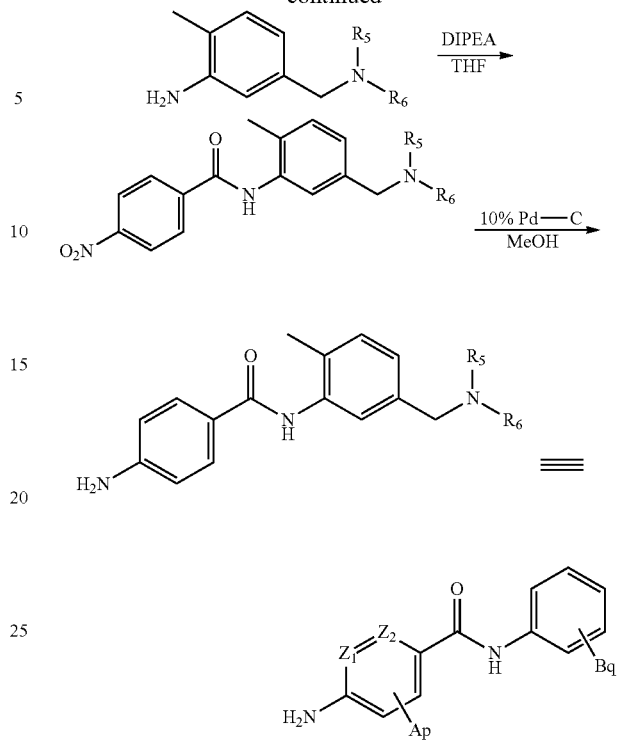

wherein $R_5$ and $R_6$, together with the N atom to which they attach, form (i) a unsubstituted or substituted morpholine ring, (ii) substituted or unsubstituted heteroaryl, (iii) substituted or unsubstituted heterocyclyl, (iv) substituted or unsubstituted aryl, or (v) substituted or unsubstituted $C_1$-$C_6$-alkyl.

Without further elaboration, it is believed that the above description has adequately enabled the present invention. The following examples are, therefore, to be construed as merely illustrative, and not limitative of the remainder of the disclosure in any way whatsoever.

EXAMPLES

Example 1

Preparation of N-(2,6-Dimethyl-phenyl)-4-[5-methylsulfanyl-4-(4-trifluoromethoxy-phenyl) -pyrimidin-2-ylamino]-benzamide (Compound 1)

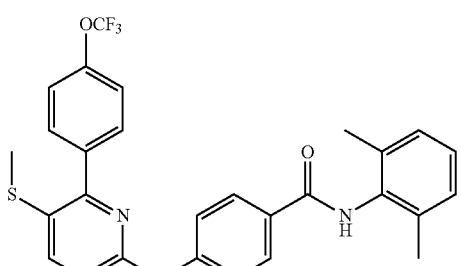

Compound 1 was prepared according to Scheme 1 below:

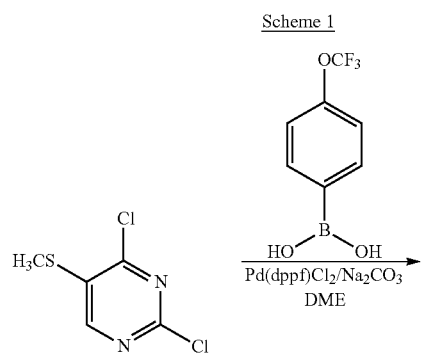

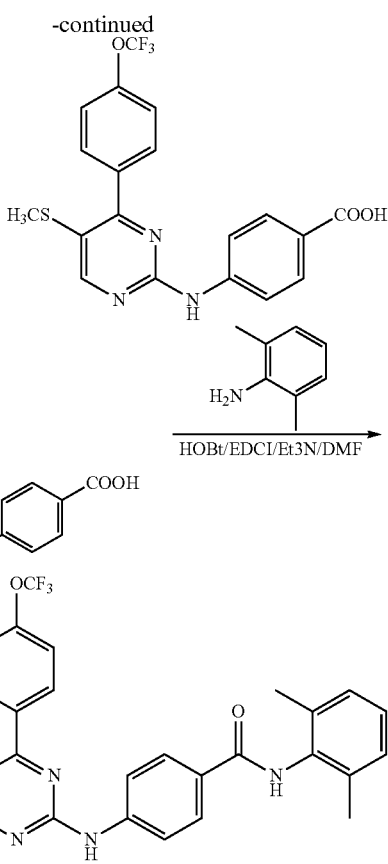

Procedure:
2-Chloro-5-(methylthio)-4-(4-(trifluoromethoxy)phenyl)pyrimidine (1-a).

To a degassed (argon) solution of 2,4-dichloro-5-(methylthio)pyrimidine (1.0 g, 1.0 eq) and 4-trifluoromethoxy phenyl boronic acid (1.1 g, 1.05 eq) in 1,2-dimethoxy ethane (15 mL) were added 2.0 M $Na_2CO_3$ (5.1 mL) and Pd(dppf)$Cl_2$ (0.21 g, 0.05 eq). The reaction mixture was heated to 70° C. for 10 h. After that, the reaction mixture was cooled to room temperature (r.t.) and quenched with water. The reaction mixture was extracted with $CH_2Cl_2$ for several times. Combined organic extracts were washed with brine, dried over $Mg_2SO_4$ and concentrated under reduced pressure to obtain a crude residue. The crude residue was purified by column chromatography (EtOAc/hexane, 1:5) to afford a white solid product of 0.71 g (yield=43%). $^1$H NMR (500 MHz, CDCl$_3$): 8.48 (s, 1H), 7.85 (d, 2H), 7.33 (d, 2H), 2.47 (s, 3H). LC/MS m/z 321.01 ([M$^+$H]$^+$), $C_{12}H_8ClF_3N_2OS$.

4-[5-Methylsulfanyl-4-(4-trifluoromethoxy-phenyl)-pyrimidin-2-ylamino]-benzoic acid ethyl ester (1-b).

A mixture of 2-chloro-5-methylsulfanyl-4-(4-trifluoromethoxy-phenyl)-pyrimidine (1-a) (700 mg, 1.0 eq) and 4-amino-benzoic acid ethyl ester (415 mg, 1.15 eq), PTSA (291 mg, 0.7 eq) in dioxane (6 mL) was heated to 130° C. for 16 h and then cooled to r.t. The mixture was dried under reduced pressure. Water was added to the mixture. The mixture was extracted with ethyl acetate (EA) several times. Combined organic extracts were washed with brine, dried over $Mg_2SO_4$ and concentrated under reduced pressure to obtain a crude residue. The crude residue was purified by column chromatography (EtOAc/hexane, 1:2) to afford a yellow oil product of 806 mg (yield=82%). $^1$H NMR (500 MHz, CDCl$_3$): 8.55 (s, 1H), 8.02 (d, 2H), 7.90 (d, 2H), 7.71

(d, 2H), 7.54 (s, 1H), 7.33 (d, 2H), 4.6 (dd, 2H), 2.29 (s, 3H), 1.39 (t, 3H). LC/MS m/z 450.33 ([M⁺H]⁺), $C_{21}H_{18}F_3N_3O_3S$.

4-[5-Methylsulfanyl-4-(4-trifluoromethoxy-phenyl)-pyrimidin-2-ylamino]-benzoic acid (1-c).

In a 50 mL reaction bottle, NaOH (214 mg, 3.0 eq) and H₂O (10 mL) were added to a solution of 4-[5-methylsulfanyl-4-(4-trifluoromethoxy-phenyl)-pyrimidin-2-ylamino]-benzoic acid ethyl ester (1-b) (800 mg, 1 eq) in MeOH (10 mL). The mixture was stirred at reflux for 2 h. The reaction mixture was cooled to room temperature, poured into ice water (20 mL), and stirred vigorously. After acidification with 2M HCl, the precipitated solid was collected by filtration. The solid was washed with ice water and dried in vacuum to give a pale yellow solid (72 mg, yield=88%). ¹H NMR (500 MHz, d-DMSO): 10.23 (s, 1H), 8.69 (s, 1H), 7.90-7.87 (m, 6H), 7.53 (s, 2H), 2.38 (s, 3H). LC/MS m/z 422.28 ([M⁺H]⁺), $C_{19}H_{14}F_3N_3O_3S$.

N-(2,6-Dimethyl-phenyl)-4-[5-methylsulfanyl-4-(4-trifluoromethoxy-phenyl)-pyrimidin-2-ylamino]-benzamide (Compound 1).

In a 25 mL reaction vial, HOBT (50 mg, 1.3 eq), EDCl (71 mg, 1.3 eq), and TEA (58 mg, 2.0 eq) were added to a solution of 4-[5-methylsulfanyl-4-(4-trifluoromethoxy-phenyl)-pyrimidin-2-ylamino]-benzoic acid (1-c) (120 mg, 1.0 eq) and 2,6-dimethylaniline (41 mg, 1.2 eq) in DMF (5 mL). The mixture was stirred at r.t. for 16 h in an N₂ atmosphere. The resulting mixture was poured into water followed by extraction with EtOAc several times. Combined organic extracts were dried over andydrous MgSO₄, and concentrated in vacuum to obtain a crude residue. The crude residue was purified by chromatography (EtOAc/hexane, 1:1) to give the product (Compound 1) (40 mg, 49%) as a white solid. ¹H NMR (500 MHz, d-DMSO): 9.71 (s, 1H), 9.35 (s, 1H), 8.69 (s, 1H), 8.35 (s, 1H), 8.00 (d, 2H), 7.75 (t, 2H), 7.40 (d, 2H), 7.11 (dd, 4H), 2.39 (s, 3H), 2.17 (s, 6H). MS: (ESI+) MH+=525.29.

Examples 2 to 84

The following compounds listed in Table 1 were synthesized by using the procedures similar to those given in Example 1:

TABLE 1

| Cmpd No. | Structure | Name |
| --- | --- | --- |
| 2 | 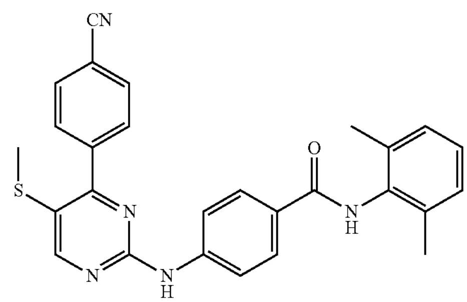 [SMILES: CSc1cnc(Nc2ccc(C(=O)Nc3c(C)cccc3C)cc2)nc1-c1ccc(C#N)cc1] | 4-[4-(4-Cyano-phenyl)-5-methylsulfanyl-pyrimidin-2-ylamino]-N-(2,6-dimethyl-phenyl)-benzamide |
| 3 | 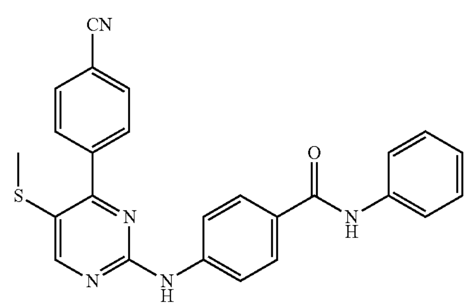 [SMILES: CSc1cnc(Nc2ccc(C(=O)Nc3ccccc3)cc2)nc1-c1ccc(C#N)cc1] | 4-[4-(4-Cyano-phenyl)-5-methylsulfanyl-pyrimidin-2-ylamino]-N-phenyl-benzamide |
| 4 | 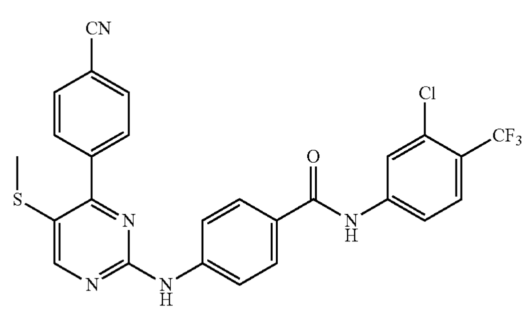 [SMILES: CSc1cnc(Nc2ccc(C(=O)Nc3ccc(C(F)(F)F)c(Cl)c3)cc2)nc1-c1ccc(C#N)cc1] | N-(3-Chloro-4-trifluoromethyl-phenyl)-4-[4-(4-cyano-phenyl)-5-methylsulfanyl-pyrimidin-2-ylamino]-benzamide |

TABLE 1-continued

| Cmpd No. | Structure | Name |
|---|---|---|
| 5 | 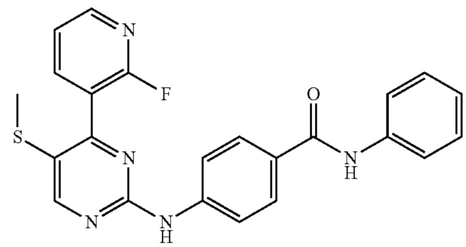 [SMILES: CSc1cnc(Nc2ccc(C(=O)Nc3ccccc3)cc2)nc1-c1cccnc1F] | 4-[4-(2-Fluoro-pyridin-3-yl)-5-methylsulfanyl-pyrimidin-2-ylamino]-N-phenyl-benzamide |
| 6 | 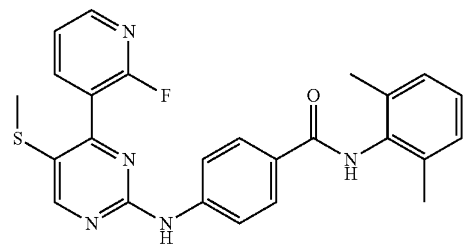 [SMILES: CSc1cnc(Nc2ccc(C(=O)Nc3c(C)cccc3C)cc2)nc1-c1cccnc1F] | N-(2,6-Dimethyl-phenyl)-4-[4-(2-fluoro-pyridin-3-yl)-5-methylsulfanyl-pyrimidin-2-ylamino]-benzamide |
| 7 | 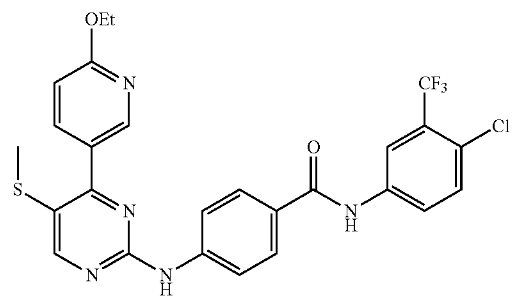 [SMILES: CCOc1ccc(-c2nc(Nc3ccc(C(=O)Nc4ccc(Cl)c(C(F)(F)F)c4)cc3)ncc2SC)cn1] | N-(4-Chloro-3-trifluoromethyl-phenyl)-4-[4-(6-ethoxy-pyridin-3-yl)-5-methylsulfanyl-pyrimidin-2-ylamino]-benzamide |
| 8 | 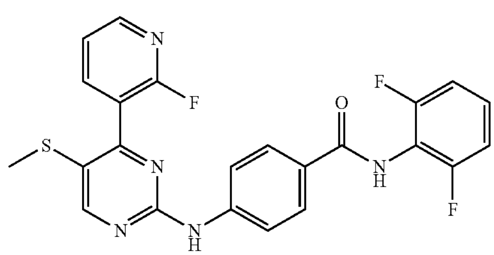 [SMILES: CSc1cnc(Nc2ccc(C(=O)Nc3c(F)cccc3F)cc2)nc1-c1cccnc1F] | N-(2,6-Difluoro-phenyl)-4-[4-(2-fluoro-pyridin-3-yl)-5-methylsulfanyl-pyrimidin-2-ylamino]-benzamide |
| 9 | 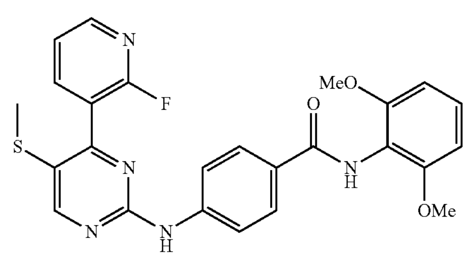 [SMILES: COc1cccc(OC)c1NC(=O)c1ccc(Nc2ncc(SC)c(-c3cccnc3F)n2)cc1] | N-(2,6-Dimethoxy-phenyl)-4-[4-(2-fluoro-pyridin-3-yl)-5-methylsulfanyl-pyrimidin-2-ylamino]-benzamide |
| 10 | 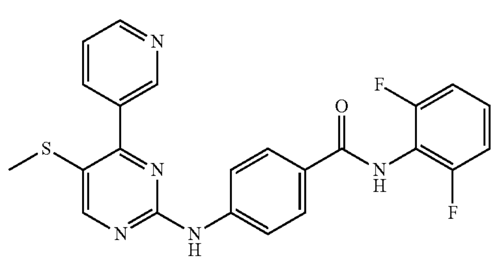 [SMILES: CSc1cnc(Nc2ccc(C(=O)Nc3c(F)cccc3F)cc2)nc1-c1cccnc1] | N-(2,6-Difluoro-phenyl)-4-(5-methylsulfanyl-4-pyridin-3-yl-pyrimidin-2-ylamino)-benzamide |

TABLE 1-continued

| Cmpd No. | Structure | Name |
|---|---|---|
| 11 | 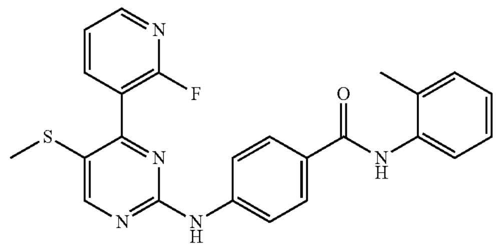 [SMILES: CSc1cnc(Nc2ccc(C(=O)Nc3ccccc3C)cc2)nc1-c1cccnc1F] | 4-[4-(2-Fluoro-pyridin-3-yl)-5-methylsulfanyl-pyrimidin-2-ylamino]-N-o-tolyl-benzamide |
| 12 | 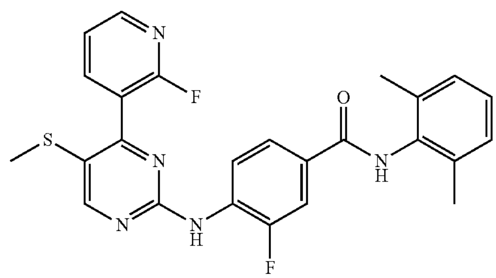 [SMILES: CSc1cnc(Nc2ccc(C(=O)Nc3c(C)cccc3C)cc2F)nc1-c1cccnc1F] | N-(2,6-Dimethyl-phenyl)-3-fluoro-4-[4-(2-fluoro-pyridin-3-yl)-5-methylsulfanyl-pyrimidin-2-ylamino]-benzamide |
| 13 | 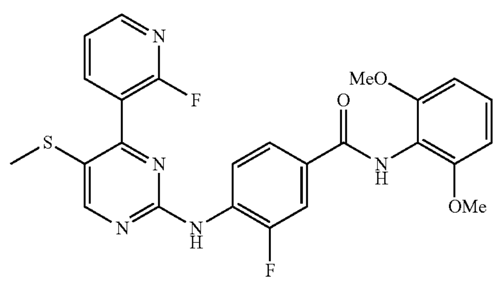 [SMILES: COc1cccc(OC)c1NC(=O)c1ccc(Nc2ncc(SC)c(-c3cccnc3F)n2)c(F)c1] | N-(2,6-Dimethoxy-phenyl)-3-fluoro-4-[4-(2-fluoro-pyridin-3-yl)-5-methylsulfanyl-pyrimidin-2-ylamino]-benzamide |
| 14 | 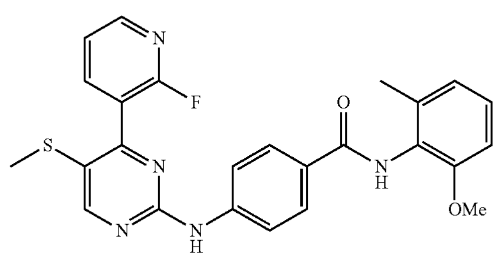 [SMILES: COc1cccc(C)c1NC(=O)c1ccc(Nc2ncc(SC)c(-c3cccnc3F)n2)cc1] | 4-[4-(2-Fluoro-pyridin-3-yl)-5-methylsulfanyl-pyrimidin-2-ylamino]-N-(2-methoxy-6-methyl-phenyl)-benzamide |
| 15 | 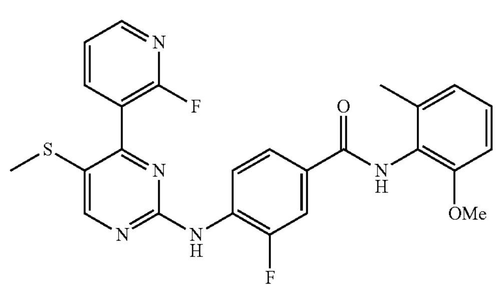 [SMILES: COc1cccc(C)c1NC(=O)c1ccc(Nc2ncc(SC)c(-c3cccnc3F)n2)c(F)c1] | 3-Fluoro-4-[4-(2-fluoro-pyridin-3-yl)-5-methylsulfanyl-pyrimidin-2-ylamino]-N-(2-methoxy-6-methyl-phenyl)-benzamide |

TABLE 1-continued

| Cmpd No. | Structure | Name |
|---|---|---|
| 16 | 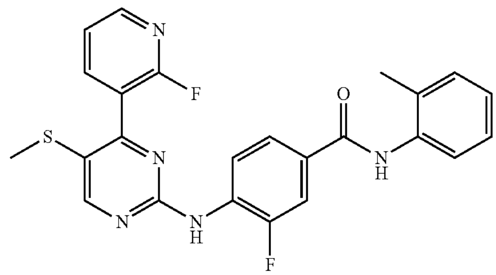 [SMILES: CSc1cnc(Nc2ccc(C(=O)Nc3ccccc3C)cc2F)nc1-c1cccnc1F] | 3-Fluoro-4-[4-(2-fluoro-pyridin-3-yl)-5-methylsulfanyl-pyrimidin-2-ylamino]-N-o-tolyl-benzamide |
| 17 | 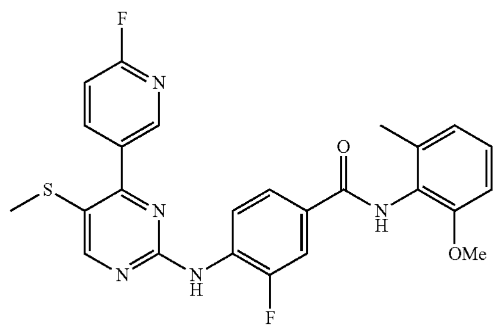 [SMILES: COc1cccc(C)c1NC(=O)c1ccc(Nc2ncc(SC)c(-c3ccc(F)nc3)n2)c(F)c1] | 3-Fluoro-4-[4-(6-fluoro-pyridin-3-yl)-5-methylsulfanyl-pyrimidin-2-ylamino]-N-(2-methoxy-6-methyl-phenyl)-benzamide |
| 18 | 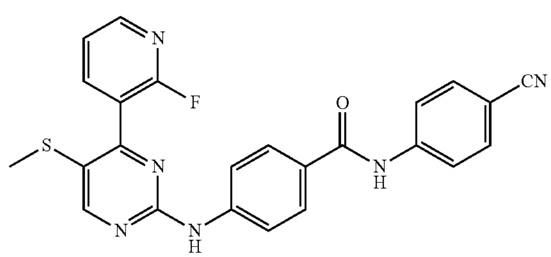 [SMILES: CSc1cnc(Nc2ccc(C(=O)Nc3ccc(C#N)cc3)cc2)nc1-c1cccnc1F] | N-(4-Cyano-phenyl)-4-[4-(2-fluoro-pyridin-3-yl)-5-methylsulfanyl-pyrimidin-2-ylamino]-benzamide |
| 19 | 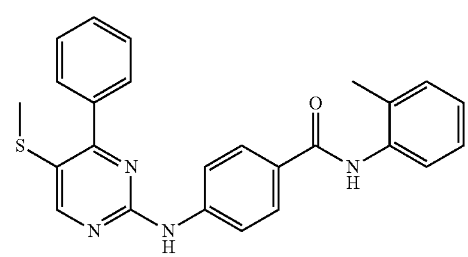 [SMILES: CSc1cnc(Nc2ccc(C(=O)Nc3ccccc3C)cc2)nc1-c1ccccc1] | 4-(5-Methylsulfanyl-4-phenyl-pyrimidin-2-ylamino)-N-o-tolyl-benzamide |
| 20 | 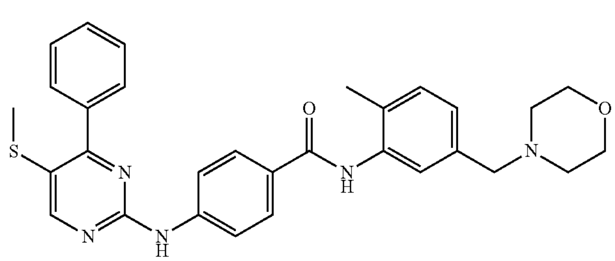 [SMILES: CSc1cnc(Nc2ccc(C(=O)Nc3cc(CN4CCOCC4)ccc3C)cc2)nc1-c1ccccc1] | N-(2-Methyl-5-morpholin-4-ylmethyl-phenyl)-4-(5-methylsulfanyl-4-phenyl-pyrimidin-2-ylamino)-benzamide |

TABLE 1-continued

| Cmpd No. | Structure | Name |
|---|---|---|
| 21 | 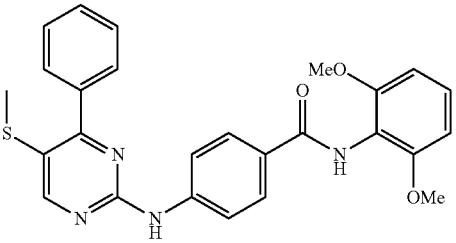 [SMILES: COc1cccc(OC)c1NC(=O)c1ccc(Nc2ncc(SC)c(-c3ccccc3)n2)cc1] | N-(2,6-Dimethoxy-phenyl)-4-(5-methylsulfanyl-4-phenyl-pyrimidin-2-ylamino)-benzamide |
| 22 | 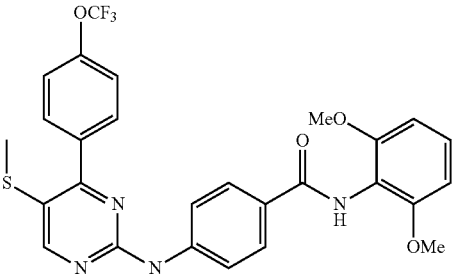 | N-(2,6-Dimethoxy-phenyl)-4-[5-methylsulfanyl-4-(4-trifluoromethoxy-phenyl)-pyrimidin-2-ylamino]-benzamide |
| 23 | 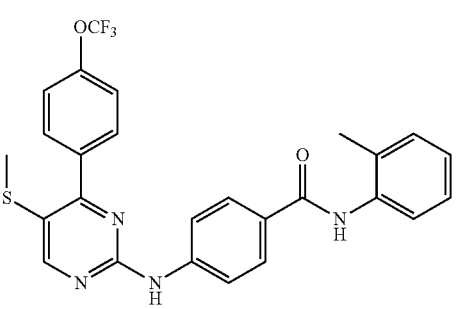 [SMILES: CSc1cnc(Nc2ccc(C(=O)Nc3ccccc3C)cc2)nc1-c1ccc(OC(F)(F)F)cc1] | 4-[5-Methylsulfanyl-4-(4-trifluoromethoxy-phenyl)-pyrimidin-2-ylamino]-N-o-tolyl-benzamide |
| 24 | 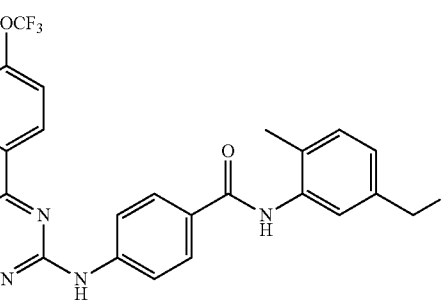 | N-(2-Methyl-5-morpholin-4-ylmethyl-phenyl)-4-[5-methylsulfanyl-4-(4-trifluoromethoxy-phenyl)-pyrimidin-2-ylamino]-benzamide |
| 25 | 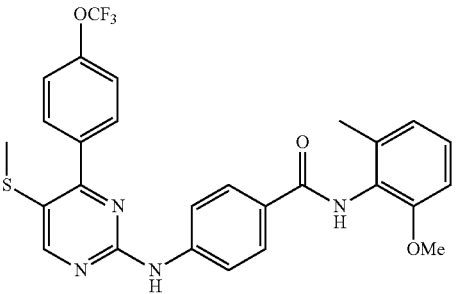 [SMILES: COc1cccc(C)c1NC(=O)c1ccc(Nc2ncc(SC)c(-c3ccc(OC(F)(F)F)cc3)n2)cc1] | N-(2-Methoxy-6-methyl-phenyl)-4-[5-methylsulfanyl-4-(4-trifluoromethoxy-phenyl)-pyrimidin-2-ylamino]-benzamide |

TABLE 1-continued

| Cmpd No. | Structure | Name |
|---|---|---|
| 26 | 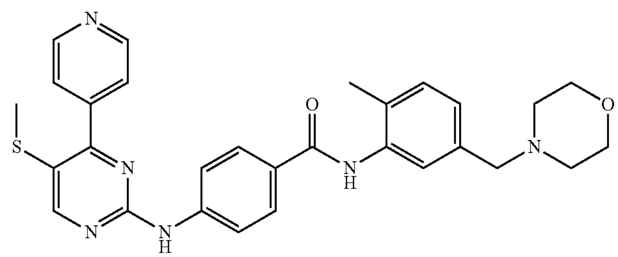 [SMILES: CSc1cnc(Nc2ccc(C(=O)Nc3cc(CN4CCOCC4)ccc3C)cc2)nc1-c1ccncc1] | N-(2-Methyl-5-morpholin-4-ylmethyl-phenyl)-4-(5-methylsulfanyl-4-pyridin-4-yl-pyrimidin-2-ylamino)-benzamide |
| 27 | 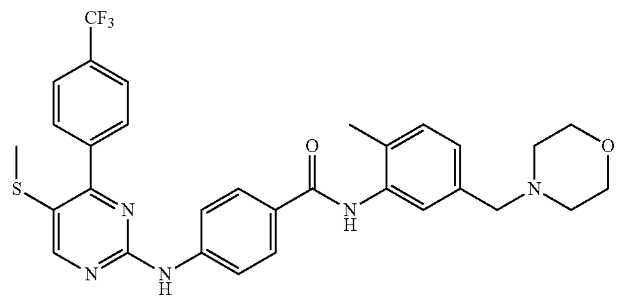 [SMILES: CSc1cnc(Nc2ccc(C(=O)Nc3cc(CN4CCOCC4)ccc3C)cc2)nc1-c1ccc(C(F)(F)F)cc1] | N-(2-Methyl-5-morpholin-4-ylmethyl-phenyl)-4-[5-methylsulfanyl-4-(4-tiifluoromethyl-phenyl)-pyrimidin-2-ylamino]-benzamide |
| 28 | 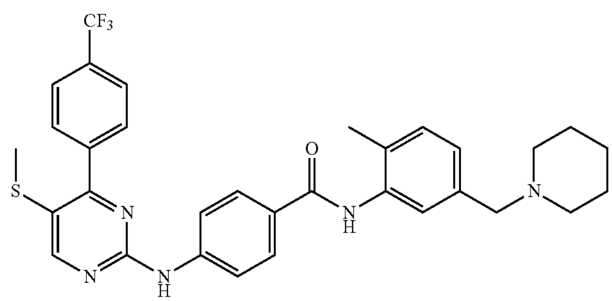 [SMILES: CSc1cnc(Nc2ccc(C(=O)Nc3cc(CN4CCCCC4)ccc3C)cc2)nc1-c1ccc(C(F)(F)F)cc1] | N-(2-Methyl-5-piperidin-1-ylmethyl-phenyl)-4-[5-methylsulfanyl-4-(4-trifluoromethyl-phenyl)-pyrimidin-2-ylamino]-benzamide |
| 29 | 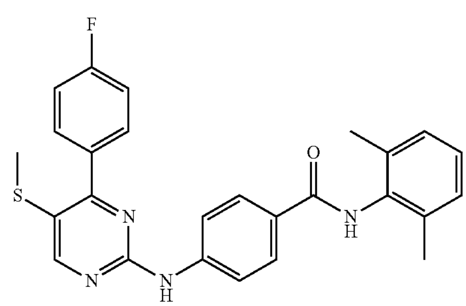 [SMILES: CSc1cnc(Nc2ccc(C(=O)Nc3c(C)cccc3C)cc2)nc1-c1ccc(F)cc1] | N-(2,6-Dimethyl-phenyl)-4-[4-(4-fluoro-phenyl)-5-methylsulfanyl-pyrimidin-2-ylamino]-benzamide |
| 30 | 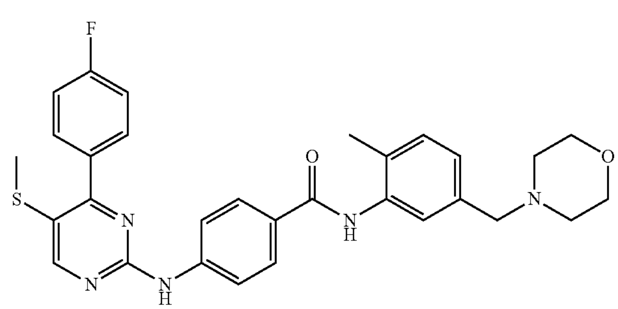 | 4-[4-(4-Fluoro-phenyl)-5-methylsulfanyl-pyrimidin-2-ylamino]-N-(2-methyl-5-morpholin-4-ylmethyl-phenyl)-benzamide |

TABLE 1-continued

| Cmpd No. | Structure | Name |
|---|---|---|
| 31 | 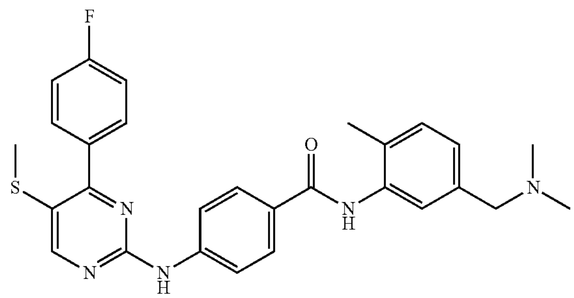 [SMILES: CSc1cnc(Nc2ccc(C(=O)Nc3cc(CN(C)C)ccc3C)cc2)nc1-c1ccc(F)cc1] | N-(5-Dimethylaminomethyl-2-methyl-phenyl)-4-[4-(4-fluoro-phenyl)-5-methylsulfanyl-pyrimidin-2-ylamino]-benzamide |
| 32 | 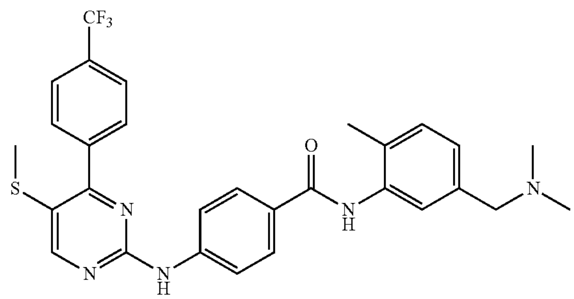 | N-(5-Dimethylaminomethyl-2-methyl-phenyl)-4-[5-methylsulfanyl-4-(4-trifluoromethyl-phenyl)-pyrimidin-2-ylamino]-benzamide |
| 33 | 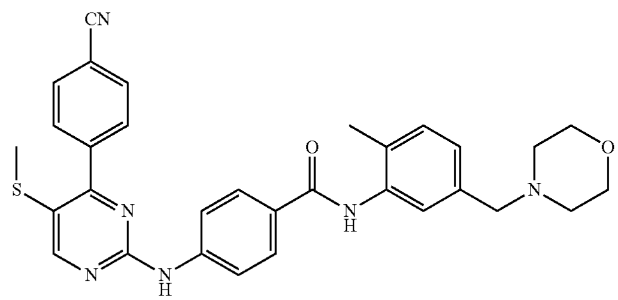 [SMILES: CSc1cnc(Nc2ccc(C(=O)Nc3cc(CN4CCOCC4)ccc3C)cc2)nc1-c1ccc(C#N)cc1] | 4-[4-(4-Cyano-phenyl)-5-methylsulfanyl-pyrimidin-2-ylamino]-N-(2-methyl-5-morpholin-4-ylmethyl-phenyl)-benzamide |
| 34 | 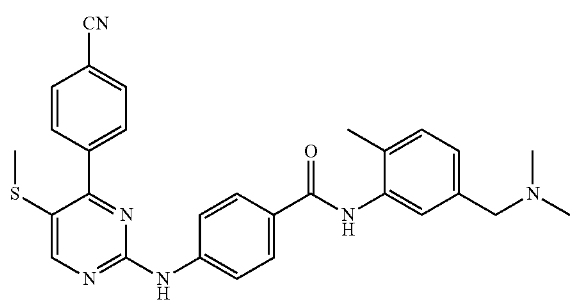 [SMILES: CSc1cnc(Nc2ccc(C(=O)Nc3cc(CN(C)C)ccc3C)cc2)nc1-c1ccc(C#N)cc1] | 4-[4-(4-Cyano-phenyl)-5-methylsulfanyl-pyrimidin-2-ylamino]-N-(5-dimethylaminomethyl-2-methyl-phenyl)-benzamide |
| 35 | 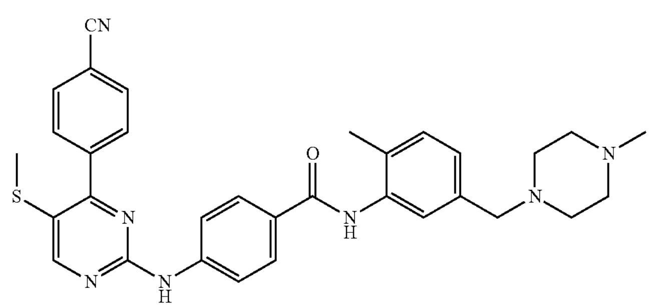 [SMILES: CSc1cnc(Nc2ccc(C(=O)Nc3cc(CN4CCN(C)CC4)ccc3C)cc2)nc1-c1ccc(C#N)cc1] | 4-[4-(4-Cyano-phenyl)-5-methylsulfanyl-pyrimidin-2-ylamino]-N-[2-methyl-5-(4-methyl-piperazin-1-ylmethyl)-phenyl]-benzamide |

TABLE 1-continued

| Cmpd No. | Structure | Name |
|---|---|---|
| 36 | 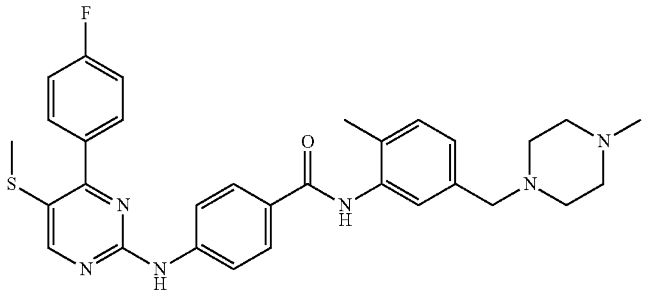 [SMILES: CSc1cnc(Nc2ccc(C(=O)Nc3cc(CN4CCN(C)CC4)ccc3C)cc2)nc1-c1ccc(F)cc1] | 4-[4-(4-Fluoro-phenyl)-5-methylsulfanyl-pyrimidin-2-ylamino]-N-[2-methyl-5-(4-methyl-piperazin-1-ylmethyl)-phenyl]-benzamide |
| 37 | 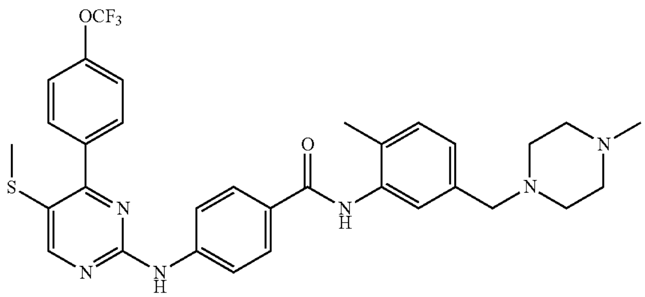 [SMILES: CSc1cnc(Nc2ccc(C(=O)Nc3cc(CN4CCN(C)CC4)ccc3C)cc2)nc1-c1ccc(OC(F)(F)F)cc1] | N-[2-Methyl-5-(4-methyl-piperazin-1-ylmethyl)-phenyl]-4-[5-methylsulfanyl-4-(4-trifluoromethoxy-phenyl)-pyrimidin-2-ylamino]-benzamide |
| 38 | 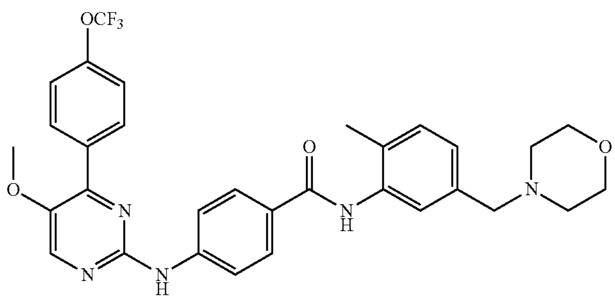 [SMILES: COc1cnc(Nc2ccc(C(=O)Nc3cc(CN4CCOCC4)ccc3C)cc2)nc1-c1ccc(OC(F)(F)F)cc1] | 4-[5-Methoxy-4-(4-trifluoromethoxy-phenyl)-pyrimidin-2-ylamino]-N-(2-methyl-5-morpholin-4-ylmethyl-phenyl)-benzamide |
| 39 | 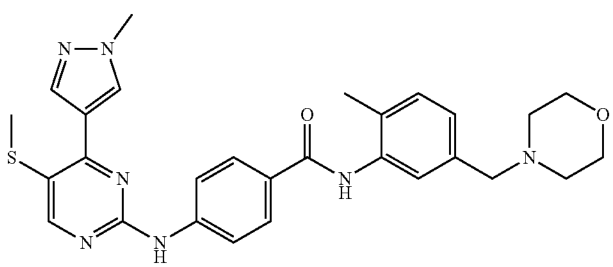 [SMILES: CSc1cnc(Nc2ccc(C(=O)Nc3cc(CN4CCOCC4)ccc3C)cc2)nc1-c1cnn(C)c1] | N-(2-Methyl-5-morpholin-4-yl methyl-phenyl)-4-[4-(1-methyl-1H-pyrazol-4-yl)-5-methylsulfanyl-pyrimidin-2-ylamino]-benzamide |
| 40 | 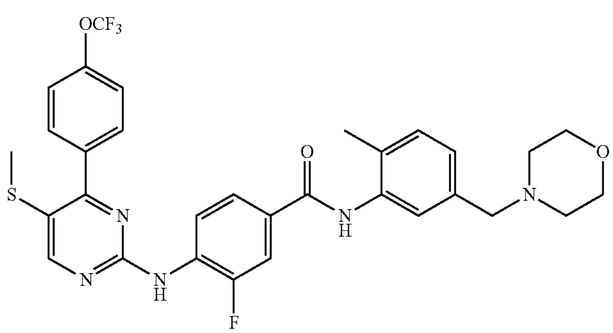 | 3-Fluoro-N-(2-methyl-5-morpholin-4-ylmethyl-phenyl)-4-[5-methylsulfanyl-4-(4-trifluoromethoxy-phenyl)-pyrimidin-2-ylamino]-benzamide |

TABLE 1-continued

| Cmpd No. | Structure | Name |
|---|---|---|
| 41 | 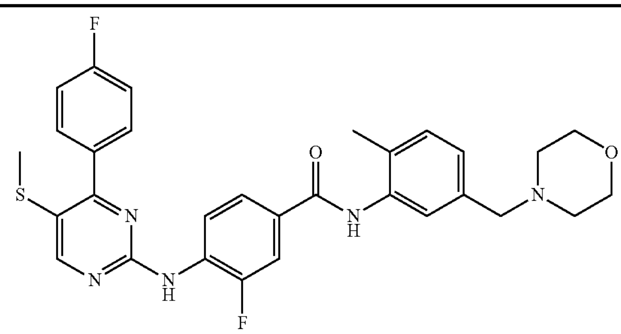 | 3-Fluoro-4-[4-(4-fluoro-phenyl)-5-methylsulfanyl-pyrimidin-2-ylamino]-N-(2-methyl-5-morpholin-4-ylmethyl-phenyl)-benzamide |
| 42 | 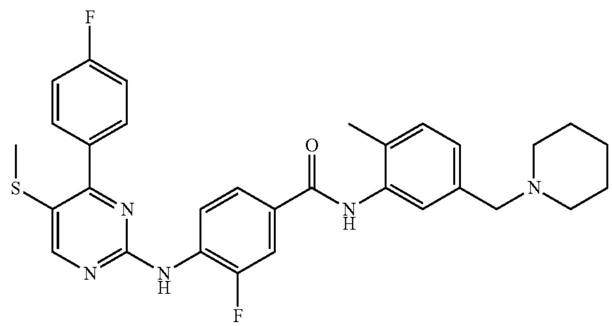 [SMILES: CSc1cnc(Nc2ccc(C(=O)Nc3cc(CN4CCCCC4)ccc3C)cc2F)nc1-c1ccc(F)cc1] | 3-Fluoro-4-[4-(4-fluoro-phenyl)-5-methylsulfanyl-pyrimidin-2-ylamino]-N-(2-methyl-5-piperidin-1-ylmethyl-phenyl)-benzamide |
| 43 | 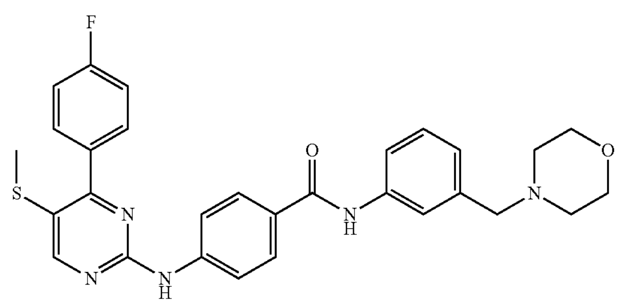 [SMILES: CSc1cnc(Nc2ccc(C(=O)Nc3cccc(CN4CCOCC4)c3)cc2)nc1-c1ccc(F)cc1] | 4-[4-(4-Fluoro-phenyl)-5-methylsulfanyl-pyrimidin-2-ylamino]-N-(3-morpholin-4-ylmethyl-phenyl)-benzamide |
| 44 | 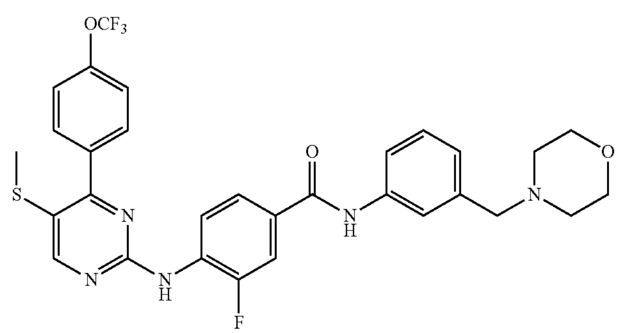 [SMILES: CSc1cnc(Nc2ccc(C(=O)Nc3cccc(CN4CCOCC4)c3)cc2F)nc1-c1ccc(OC(F)(F)F)cc1] | 3-Fluoro-4-[5-methylsulfanyl-4-(4-trifluoromethoxy-phenyl)-pyrimidin-2-ylamino]-N-(3-morpholin-4-ylmethyl-phenyl)-benzamide |
| 45 | 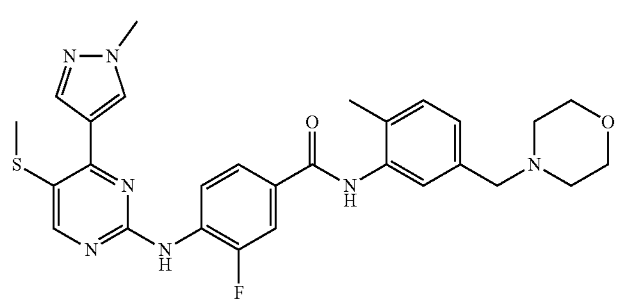 [SMILES: CSc1cnc(Nc2ccc(C(=O)Nc3cc(CN4CCOCC4)ccc3C)cc2F)nc1-c1cnn(C)c1] | 3-Fluoro-N-(2-methyl-5-morpholin-4-ylmethyl-phenyl)-4-[4-(1-methyl-1H-pyrazol-4-yl)-5-methylsulfanyl-pyrimidin-2-ylamino]-benzamide |

TABLE 1-continued

| Cmpd No. | Structure | Name |
|---|---|---|
| 46 | 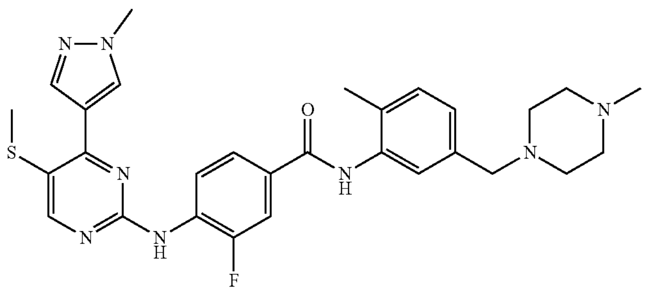 [SMILES: CSc1cnc(Nc2ccc(C(=O)Nc3cc(CN4CCN(C)CC4)ccc3C)cc2F)nc1-c1cnn(C)c1] | 3-Fluoro-N-[2-methyl-5-(4-methyl-piperazin-1-ylmethyl)-phenyl]-4-[4-(1-methyl-1H-pyrazol-4-yl)-5-methylsulfanyl-pyrimidin-2-ylamino]-benzamide |
| 47 | 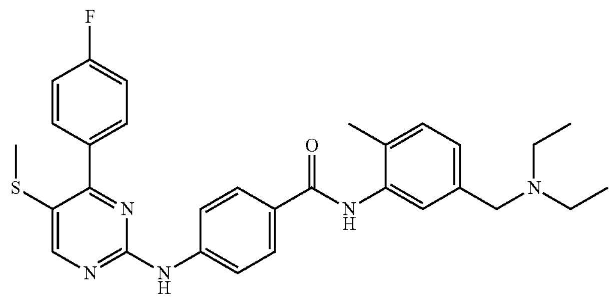 [SMILES: CCN(CC)Cc1ccc(C)c(NC(=O)c2ccc(Nc3ncc(SC)c(-c4ccc(F)cc4)n3)cc2)c1] | N-(5-Diethylaminomethyl-2-methyl-phenyl)-4-[4-(4-fluoro-phenyl)-5-methylsulfanyl-pyrimidin-2-ylamino]-benzamide |
| 48 | 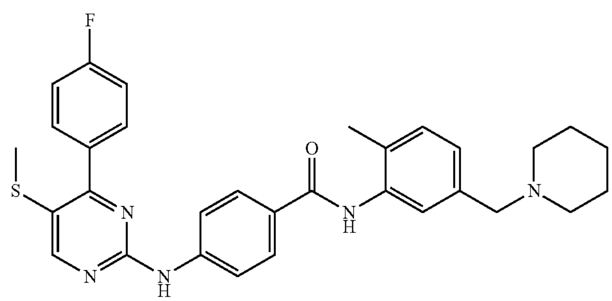 [SMILES: CSc1cnc(Nc2ccc(C(=O)Nc3cc(CN4CCCCC4)ccc3C)cc2)nc1-c1ccc(F)cc1] | 4-[4-(4-Fluoro-phenyl)-5-methylsulfanyl-pyrimidin-2-ylamino]-N-(2-methyl-5-piperidin-1-ylmethyl-phenyl)-benzamide |
| 49 | 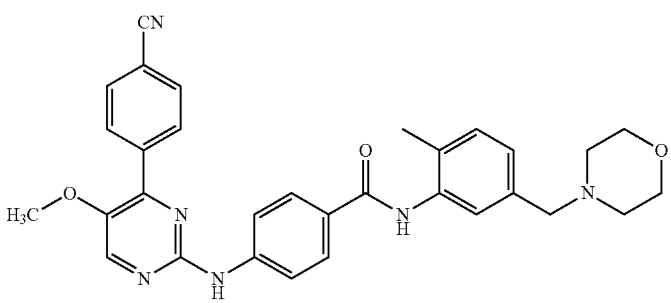 [SMILES: COc1cnc(Nc2ccc(C(=O)Nc3cc(CN4CCOCC4)ccc3C)cc2)nc1-c1ccc(C#N)cc1] | 4-[4-(4-Cyano-phenyl)-5-methoxy-pyrimidin-2-ylamino]-N-(2-methyl-5-morpholin-4-ylmethyl-phenyl)-benzamide |
| 50 | 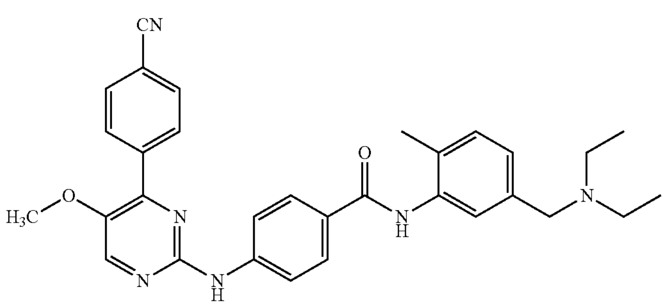 [SMILES: CCN(CC)Cc1ccc(C)c(NC(=O)c2ccc(Nc3ncc(OC)c(-c4ccc(C#N)cc4)n3)cc2)c1] | 4-[4-(4-Cyano-phenyl)-5-methoxy-pyrimidin-2-ylamino]-N-(5-diethylaminomethyl-2-methyl-phenyl)-benzamide |

TABLE 1-continued

| Cmpd No. | Structure | Name |
|---|---|---|
| 51 | 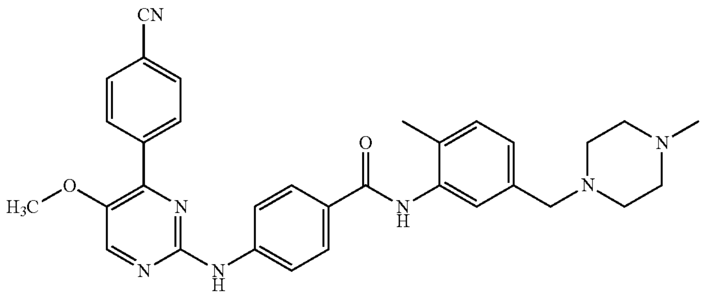 | 4-[4-(4-Cyano-phenyl)-5-methoxy-pyrimidin-2-ylamino]-N-[2-methyl-5-(4-methyl-piperazin-1-ylmethyl)-phenyl]-benzamide |
| 52 | 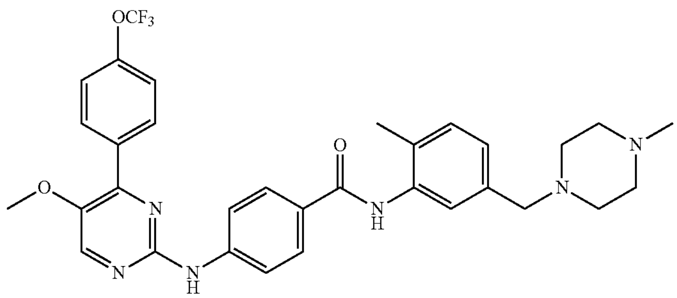 | 4-[5-Methoxy-4-(4-trifluoromethoxy-phenyl)-pyrimidin-2-ylamino]-N-[2-methyl-5-(4-methyl-piperazin-1-ylmethyl)-phenyl]-benzamide |
| 53 | 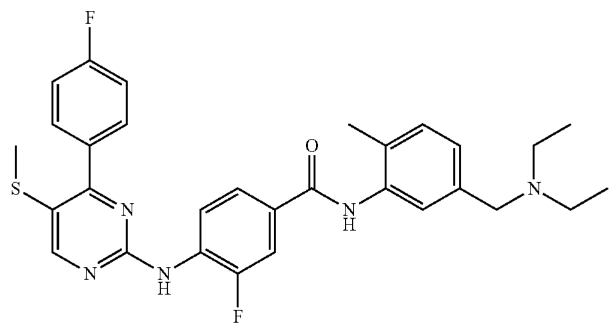 [SMILES: CCN(CC)Cc1ccc(C)c(NC(=O)c2ccc(Nc3ncc(SC)c(-c4ccc(F)cc4)n3)c(F)c2)c1] | N-(5-Diethylaminomethyl-2-methyl-phenyl)-3-fluoro-4-[4-(4-fluoro-phenyl)-5-methylsulfanyl-pyrimidin-2-ylamino]-benzamide |
| 54 | 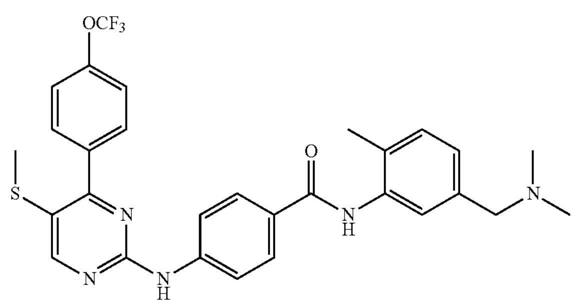 [SMILES: CSc1cnc(Nc2ccc(C(=O)Nc3cc(CN(C)C)ccc3C)cc2)nc1-c1ccc(OC(F)(F)F)cc1] | N-(5-Dimethylaminomethyl-2-methyl-phenyl)-4-[5-methylsulfanyl-4-(4-trifluoromethoxy-phenyl)-pyrimidin-2-ylamino]-benzamide |
| 55 | 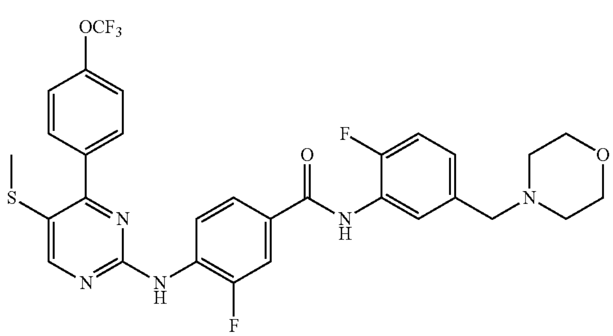 [SMILES: CSc1cnc(Nc2ccc(C(=O)Nc3cc(CN4CCOCC4)ccc3F)cc2F)nc1-c1ccc(OC(F)(F)F)cc1] | 3-Fluoro-N-(2-fluoro-5-morpholin-4-ylmethyl-phenyl)-4-[5-methylsulfanyl-4-(4-trifluoromethoxy-phenyl)-pyrimidin-2-ylamino]-benzamide |

TABLE 1-continued

| Cmpd No. | Structure | Name |
|---|---|---|
| 56 | 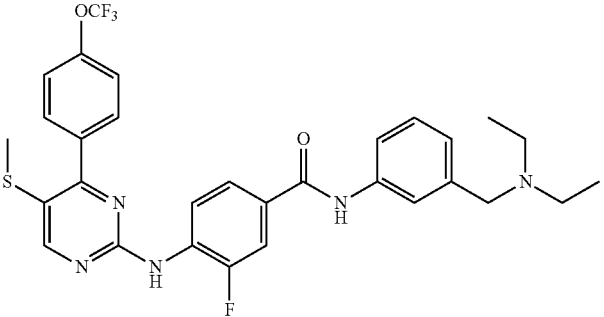 [SMILES: CCN(CC)Cc1cccc(NC(=O)c2ccc(Nc3ncc(SC)c(-c4ccc(OC(F)(F)F)cc4)n3)c(F)c2)c1] | N-(3-Diethylaminomethyl-phenyl)-3-fluoro-4-[5-methylsulfanyl-4-(4-trifluoromethoxy-phenyl)-pyrimidin-2-ylamino]-benzamide |
| 57 | 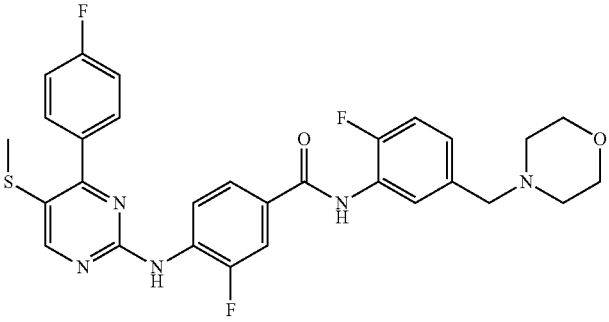 [SMILES: CSc1cnc(Nc2ccc(C(=O)Nc3cc(CN4CCOCC4)ccc3F)cc2F)nc1-c1ccc(F)cc1] | 3-Fluoro-N-(2-fluoro-5-morpholin-4-ylmethyl-phenyl)-4-[4-(4-fluoro-phenyl)-5-methylsulfanyl-pyrimidin-2-ylamino]-benzamide |
| 58 | 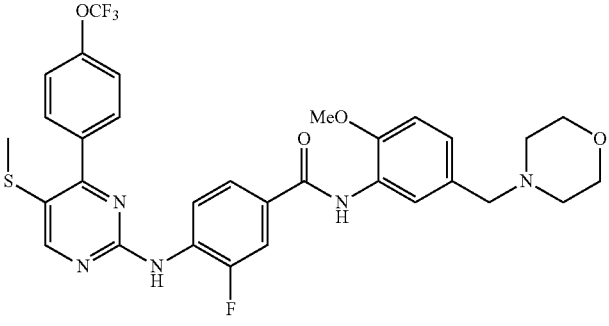 [SMILES: COc1ccc(CN2CCOCC2)cc1NC(=O)c1ccc(Nc2ncc(SC)c(-c3ccc(OC(F)(F)F)cc3)n2)c(F)c1] | 3-Fluoro-N-(2-methoxy-5-morpholin-4-ylmethyl-phenyl)-4-[5-methylsulfanyl-4-(4-trifluoromethoxy-phenyl)-pyrimidin-2-ylamino]-benzamide |
| 59 | 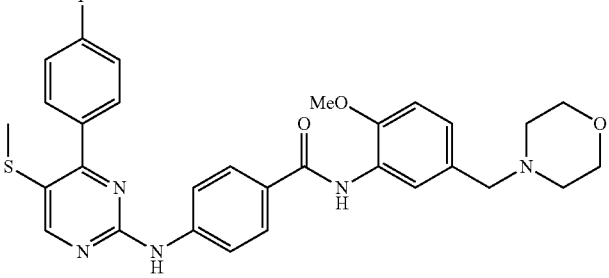 | 4-[4-(4-Fluoro-phenyl)-5-methylsulfanyl-pyrimidin-2-ylamino]-N-(2-methoxy-5-morpholin-4-ylmethyl-phenyl)-benzamide |
| 60 | 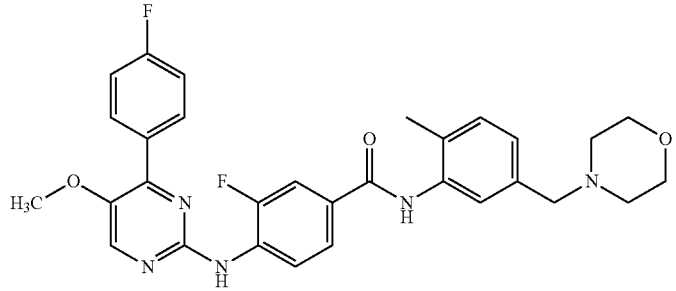 [SMILES: COc1cnc(Nc2ccc(C(=O)Nc3cc(CN4CCOCC4)ccc3C)cc2F)nc1-c1ccc(F)cc1] | 3-Fluoro-4-[4-(4-fluoro-phenyl)-5-methoxy-pyrimidin-2-ylamino]-N-(2-methyl-5-morpholin-4-ylmethyl-phenyl)-benzamide |

TABLE 1-continued

| Cmpd No. | Structure | Name |
|---|---|---|
| 61 | 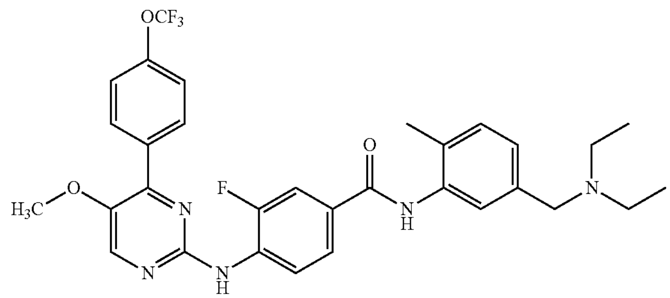 [SMILES: CCN(CC)Cc1ccc(C)c(NC(=O)c2ccc(Nc3ncc(OC)c(-c4ccc(OC(F)(F)F)cc4)n3)c(F)c2)c1] | N-(5-Diethylaminomethyl-2-methyl-phenyl)-3-fluoro-4-[5-methoxy-4-(4-trifluoromethoxy-phenyl)-pyrimidin-2-ylamino]-benzamide |
| 62 | 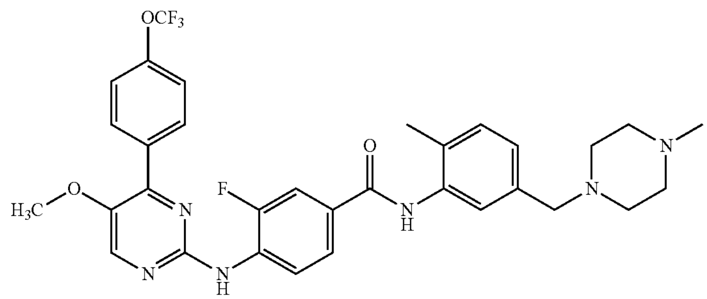 | 3-Fluoro-4-[5-methoxy-4-(4-trifluoromethoxy-phenyl)-pyrimidin-2-ylamino]-N-[2-methyl-5-(4-methyl-piperazin-1-ylmethyl)-phenyl]-benzamide |
| 63 | 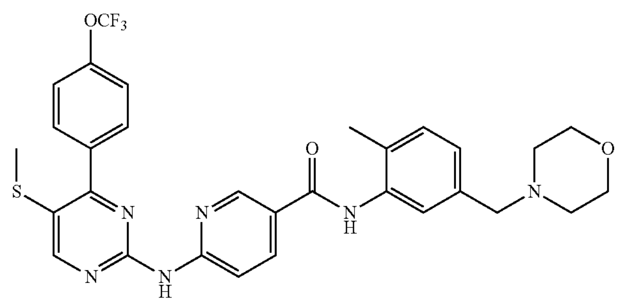 [SMILES: CSc1cnc(Nc2ccc(C(=O)Nc3cc(CN4CCOCC4)ccc3C)cn2)nc1-c1ccc(OC(F)(F)F)cc1] | N-(2-Methyl-5-morpholin-4-ylmethyl-phenyl)-6-[5-methylsulfanyl-4-(4-trifluoromethoxy-phenyl)-pyrimidin-2-ylamino]-nicotinamide |
| 64 | 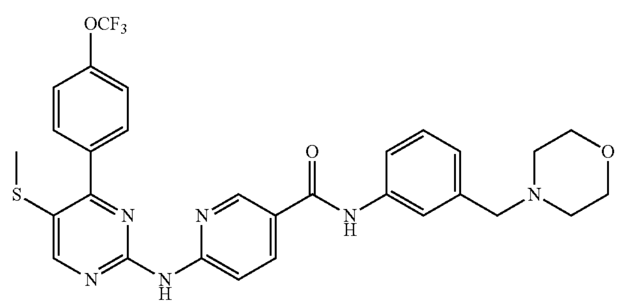 [SMILES: CSc1cnc(Nc2ccc(C(=O)Nc3cccc(CN4CCOCC4)c3)cn2)nc1-c1ccc(OC(F)(F)F)cc1] | 6-[5-Methylsulfanyl-4-(4-trifluoromethoxy-phenyl)-pyrimidin-2-ylamino]-N-(3-morpholin-4-ylmethyl-phenyl)-nicotinamide |
| 65 | 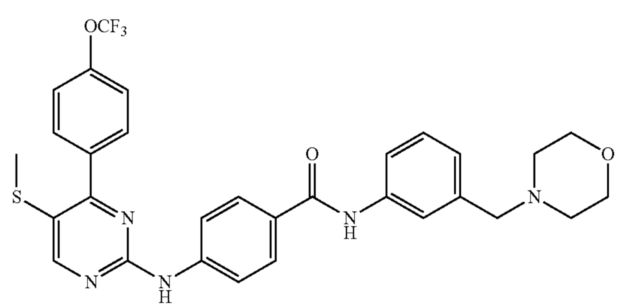 [SMILES: CSc1cnc(Nc2ccc(C(=O)Nc3cccc(CN4CCOCC4)c3)cc2)nc1-c1ccc(OC(F)(F)F)cc1] | 4-[5-Methylsulfanyl-4-(4-trifluoromethoxy-phenyl)-pyrimidin-2-ylamino]-N-(3-morpholin-4-ylmethyl-phenyl)-benzamide |

TABLE 1-continued

| Cmpd No. | Structure | Name |
|---|---|---|
| 66 | 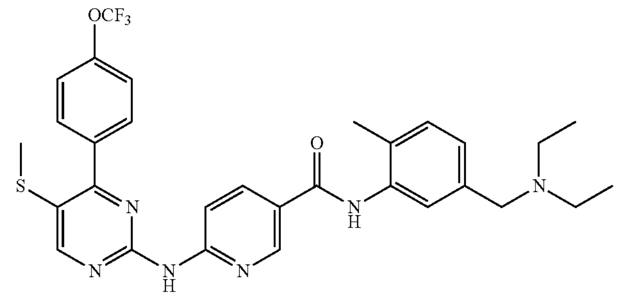 [SMILES: CCN(CC)Cc1ccc(C)c(NC(=O)c2ccc(Nc3ncc(SC)c(-c4ccc(OC(F)(F)F)cc4)n3)nc2)c1] | N-(5-Diethylaminomethyl-2-methyl-phenyl)-6-[5-methylsulfanyl-4-(4-trifluoromethoxy-phenyl)-pyrimidin-2-ylamino]-nicotinamide |
| 67 | 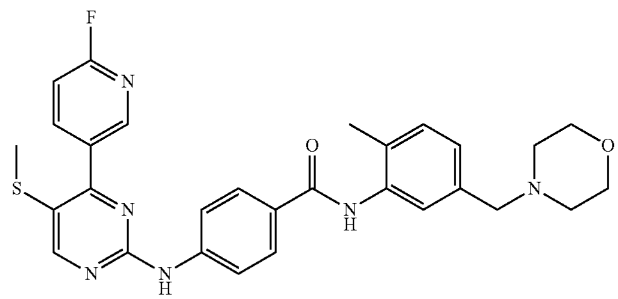 [SMILES: CSc1cnc(Nc2ccc(C(=O)Nc3cc(CN4CCOCC4)ccc3C)cc2)nc1-c1ccc(F)nc1] | 4-[4-(6-Fluoro-pyridin-3-yl)-5-methylsulfanyl-pyrimidin-2-ylamino]-N-(2-methyl-5-morpholin-4-ylmethyl-phenyl)-benzamide |
| 68 | 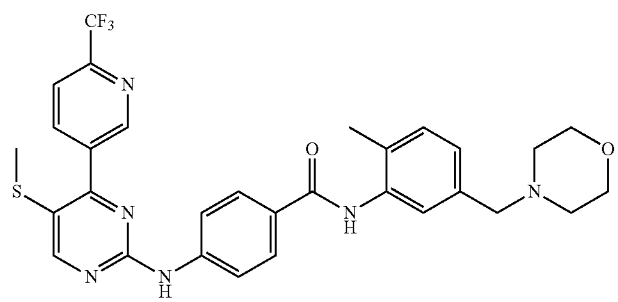 [SMILES: CSc1cnc(Nc2ccc(C(=O)Nc3cc(CN4CCOCC4)ccc3C)cc2)nc1-c1ccc(C(F)(F)F)nc1] | N-(2-Methyl-5-morpholin-4-ylmethyl-phenyl)-4-[5-methylsulfanyl-4-(6-trifluoromethyl-pyridin-3-yl)-pyrimidin-2-ylamino]-benzamide |
| 69 | 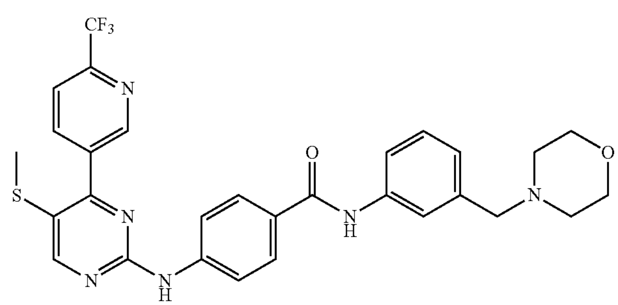 [SMILES: CSc1cnc(Nc2ccc(C(=O)Nc3cccc(CN4CCOCC4)c3)cc2)nc1-c1ccc(C(F)(F)F)nc1] | 4-[5-Methylsulfanyl-4-(6-trifluoromethyl-pyridin-3-yl)-pyrimidin-2-ylamino]-N-(3-morpholin-4-ylmethyl-phenyl)-benzamide |
| 70 | 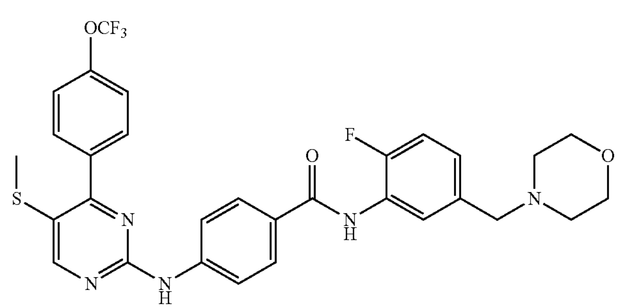 | N-(2-Fluoro-5-morpholin-4-ylmethyl-phenyl)-4-[5-methylsulfanyl-4-(4-trifluoromethoxy-phenyl)-pyrimidin-2-ylamino]-benzamide |

TABLE 1-continued

| Cmpd No. | Structure | Name |
|---|---|---|
| 71 | 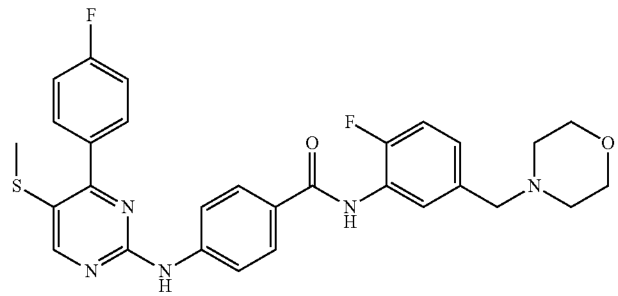 | N-(2-Fluoro-5-morpholin-4-ylmethyl-phenyl)-4-[4-(4-fluoro-phenyl)-5-methylsulfanyl-pyrimidin-2-ylamino]-benzamide |
| 72 | 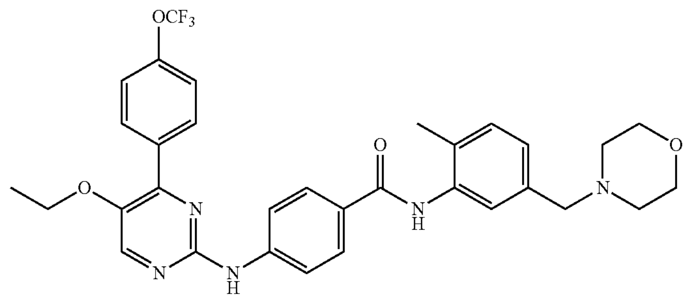 [SMILES: CCOc1cnc(Nc2ccc(C(=O)Nc3cc(CN4CCOCC4)ccc3C)cc2)nc1-c1ccc(OC(F)(F)F)cc1] | 4-[5-Ethoxy-4-(4-trifluoromethoxy-phenyl)-pyrimidin-2-ylamino]-N-(2-methyl-5-morpholin-4-ylmethyl-phenyl)-benzamide |
| 73 | 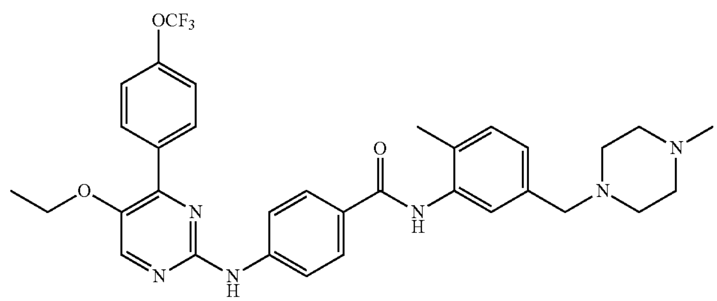 [SMILES: CCOc1cnc(Nc2ccc(C(=O)Nc3cc(CN4CCN(C)CC4)ccc3C)cc2)nc1-c1ccc(OC(F)(F)F)cc1] | 4-[5-Ethoxy-4-(4-trifluoromethoxy-phenyl)-pyrimidin-2-ylamino]-N-[2-methyl-5-(4-methyl-piperazin-1-ylmethyl)-phenyl]-benzamide |
| 74 | 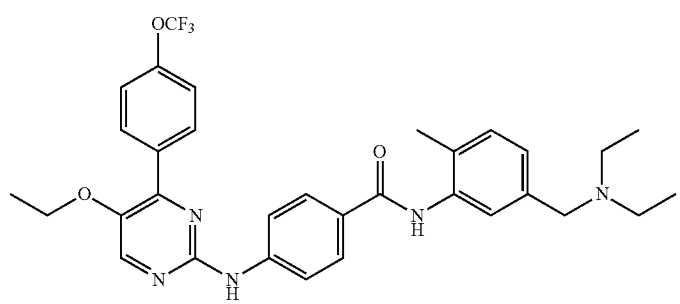 [SMILES: CCOc1cnc(Nc2ccc(C(=O)Nc3cc(CN(CC)CC)ccc3C)cc2)nc1-c1ccc(OC(F)(F)F)cc1] | N-(5-Diethylaminomethyl-2-methyl-phenyl)-4-[5-ethoxy-4-(4-trifluoromethoxy-phenyl)-pyrimidin-2-ylamino]-benzamide |
| 75 | 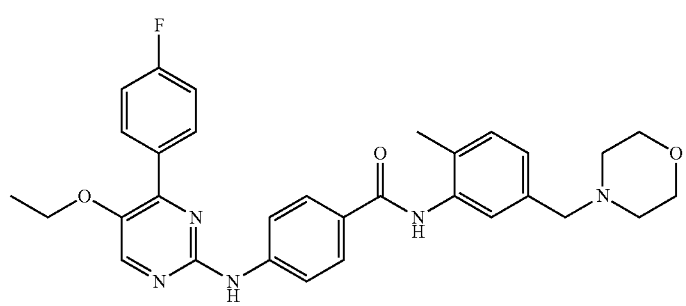 [SMILES: CCOc1cnc(Nc2ccc(C(=O)Nc3cc(CN4CCOCC4)ccc3C)cc2)nc1-c1ccc(F)cc1] | 4-[5-Ethoxy-4-(4-fluoro-phenyl)-pyrimidin-2-ylamino]-N-(2-methyl-5-morpholin-4-ylmethyl-phenyl)-benzamide |

TABLE 1-continued

| Cmpd No. | Structure | Name |
|---|---|---|
| 76 | 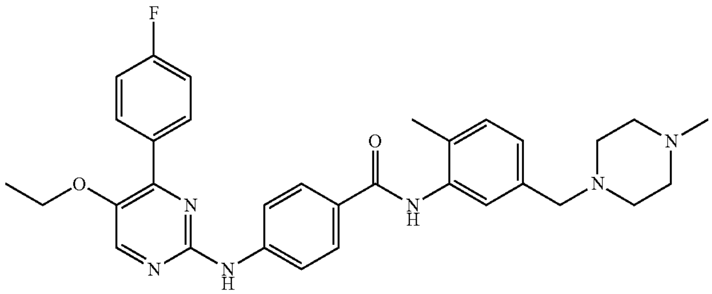 [SMILES: CCOc1cnc(Nc2ccc(C(=O)Nc3cc(CN4CCN(C)CC4)ccc3C)cc2)nc1-c1ccc(F)cc1] | 4-[5-Ethoxy-4-(4-fluoro-phenyl)-pyrimidin-2-ylamino]-N-[2-methyl-5-(4-methyl-piperazin-1-ylmethyl)-phenyl]-benzamide |
| 77 | 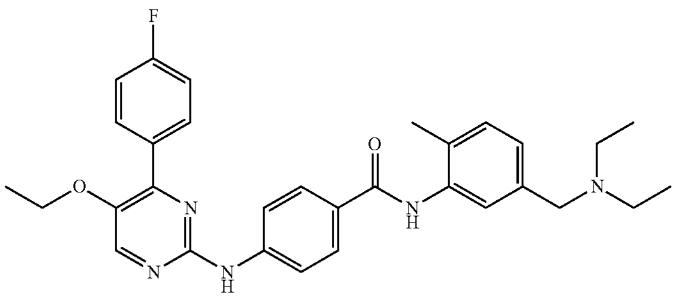 [SMILES: CCOc1cnc(Nc2ccc(C(=O)Nc3cc(CN(CC)CC)ccc3C)cc2)nc1-c1ccc(F)cc1] | N-(5-Diethylaminomethyl-2-methyl-phenyl)-4-[5-ethoxy-4-(4-fluoro-phenyl)-pyrimidin-2-ylamino]-benzamide |
| 78 | 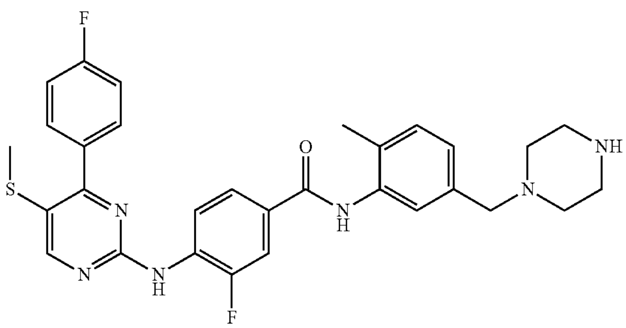 [SMILES: CSc1cnc(Nc2ccc(C(=O)Nc3cc(CN4CCNCC4)ccc3C)cc2F)nc1-c1ccc(F)cc1] | 3-Fluoro-4-[4-(4-fluoro-phenyl)-5-methylsulfanyl-pyrimidin-2-ylamino]-N-(2-methyl-5-piperazin-1-ylmethyl-phenyl)-benzamide |
| 79 | 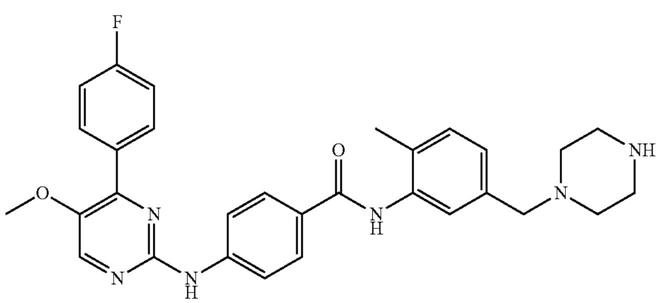 [SMILES: COc1cnc(Nc2ccc(C(=O)Nc3cc(CN4CCNCC4)ccc3C)cc2)nc1-c1ccc(F)cc1] | 4-[4-(4-Fluoro-phenyl)-5-methoxy-pyrimidin-2-ylamino]-N-(2-methyl-5-piperazin-1-ylmethyl-phenyl)-benzamide |
| 80 | 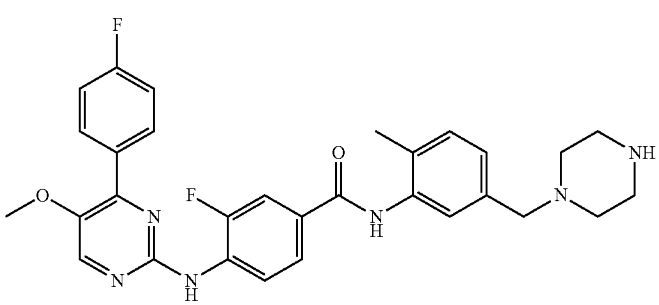 [SMILES: COc1cnc(Nc2ccc(C(=O)Nc3cc(CN4CCNCC4)ccc3C)cc2F)nc1-c1ccc(F)cc1] | 3-Fluoro-4-[4-(4-fluoro-phenyl)-5-methoxy-pyrimidin-2-ylamino]-N-(2-methyl-5-piperazin-1-ylmethyl-phenyl)-benzamide |

TABLE 1-continued

| Cmpd No. | Structure | Name |
|---|---|---|
| 81 | 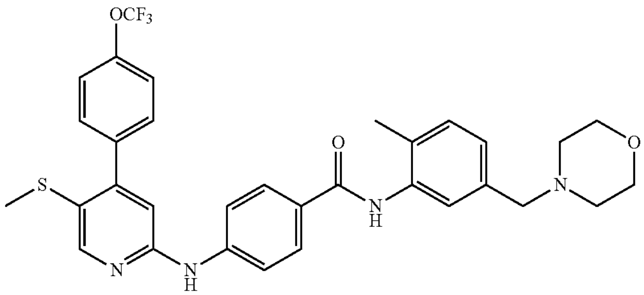 [SMILES: CSc1cnc(Nc2ccc(C(=O)Nc3cc(CN4CCOCC4)ccc3C)cc2)cc1-c1ccc(OC(F)(F)F)cc1] | N-(2-Methyl-5-morpholin-4-ylmethyl-phenyl)-4-[5-methylsulfanyl-4-(4-trifluoromethoxy-phenyl)-pyridin-2-ylamino)-benzamide |
| 82 | 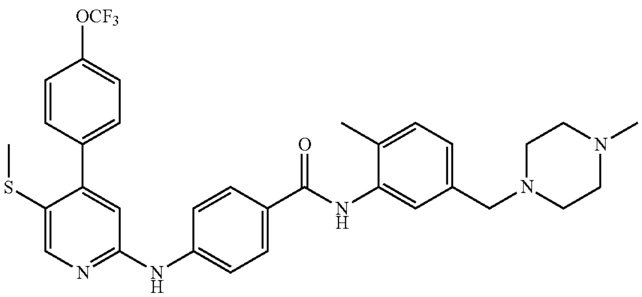 [SMILES: CSc1cnc(Nc2ccc(C(=O)Nc3cc(CN4CCN(C)CC4)ccc3C)cc2)cc1-c1ccc(OC(F)(F)F)cc1] | N-[2-Methyl-5-(4-methyl-piperazin-1-ylmethyl)-phenyl]-4-[5-methylsulfanyl-4-(4-trifluoromethoxy-phenyl)-pyridin-2-ylamino]-benzamide |
| 83 | 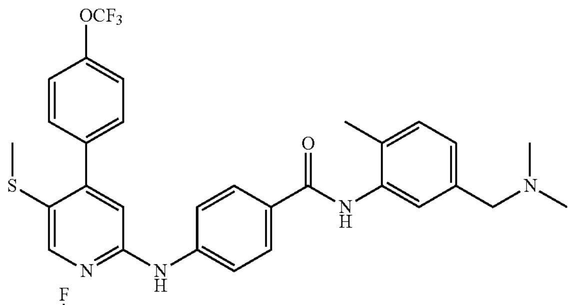 | N-(5-Dimethylaminomethyl-2-methyl-phenyl)-4-[5-methylsulfanyl-4-(4-trifluoromethoxy-phenyl)-pyridin-2-ylamino]-benzamide |
| 84 | 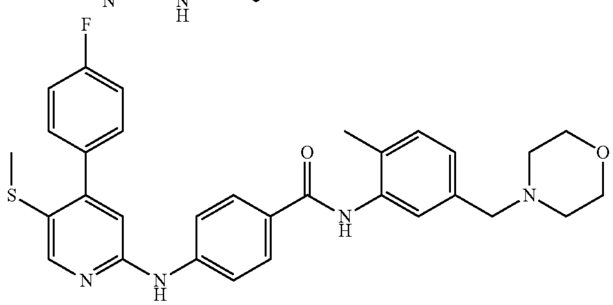 | 4-((4-(4-fluorophenyl)-5-(methylthio)pyridin-2-yl)amino)-N-(2-methyl-5-(morpholinomethyl)phenyl)benzamide |

The data of the compounds of Examples 2 to 84 are given below:

Cmpd 2
4-[4-(4-Cyano-phenyl)-5-methylsulfanyl-pyrimidin-2-ylamino]-N-(2,6-dimethyl-phenyl)-benzamide
$^1$H NMR (500 MHz, d-DMSO): 10.25 (s, 1H), 9.57 (s, 1H), 8.74 (s, 1H), 8.02 (d, 2H), 7.95 (d, 2H), 7.90 (dd, 4H), 7.11 (s, 3H), 2.37 (s, 3H), 2.17 (s, 6H).
MS: (ESI+) MH+=466.14.

Cmpd 3
4-[4-(4-Cyano-phenyl)-5-methylsulfanyl-pyrimidin-2-ylamino]-N-phenyl-benzamide
$^1$H NMR (500 MHz, d-DMSO): 10.26 (s, 1H), 10.04 (s, 1H), 8.74 (s, 1H), 8.02 (d, 2H), 8.00 (d, 2H), 7.91 (t, 6H), 7.77 (d, 2H), 7.33 (t, 2H), 7.07 (d, 1H), 2.38 (s, 3H).
MS: (ESI+) MH+=438.14.

Cmpd 4
N-(3-Chloro-4-trifluoromethyl-phenyl)-4-[4-(4-cyano-phenyl)-5-methylsulfanyl-pyrimidin-2-ylamino]-benzamide
$^1$H NMR (500 MHz, d-DMSO): 10.45 (s, 1H), 10.31 (s, 1H), 8.74 (s, 1H), 8.37 (s, 1H), 8.10 (d, 1H), 8.01 (d, 2H), 7.91 (t, 6H), 7.69 (s, 1H), 2.38 (s, 3H).
MS: (ESI+) MH+=540.1.

Cmpd 5
4-[4-(2-Fluoro-pyridin-3-yl)-5-methylsulfanyl-pyrimidin-2-ylamino]-N-phenyl-benzamide
$^1$H NMR (500 MHz, d-DMSO): 10.32 (s, 1H), 10.03 (s, 1H), 8.78 (s, 1H), 8.42 (s, 1H), 8.19 (t, 1H), 7.90 (d, 2H), 7.88 (d, 2H), 7.76 (d, 2H), 7.56 (s, 1H), 7.33 (d, 2H), 7.07 (t, 1H), 2.35 (s, 3H).
MS: (ESI+) MH+=432.10.

Cmpd 6
N-(2,6-Dimethyl-phenyl)-4-[4-(2-fluoro-pyridin-3-yl)-5-methylsulfanyl-pyrimidin-2-ylamino]-benzamide
$^1$NMR (500 MHz, d-DMSO): 10.30 (s, 1H), 9.56 (s, 1H), 8.78 (s, 1H), 8.41 (s, 1H), 8.19 (s, 1H), 7.94 (d, 2H), 7.87 (d, 2H), 7.56 (d, 1H), 7.11 (s, 3H), 2.35 (s, 3H), 2.16 (s, 6H).
MS: (ESI+) MH+=460.03.

Cmpd 7
N-(4-Chloro-3-trifluoromethyl-phenyl)-4-[4-(6-ethoxy-pyridin-3-yl)-5-methylsulfanyl-pyrimidin -2-ylamino]-benzamide
$^1$NMR (500 MHz, d-DMSO): 10.46 (s, 1H), 10.24 (s, 1H), 8.68 (s, 1H), 8.61 (s, 1H), 8.37 (d, 1H), 8.13-8.09 (m, 2H), 8.09 (s, 4H), 7.71 (d, 1H), 6.94 (d, 1H), 4.40 (dd, 2H), 2.36 (s, 3H), 1.35 (t, 3H).
MS: (ESI+) MH+=560.38.

Cmpd 8
N-(2,6-Difluoro-phenyl)-4-[4-(2-fluoro-pyridin-3-yl)-5-methylsulfanyl-pyrimidin-2-ylamino]-benzamide
$^1$NMR (500 MHz, CDCl$_3$): 8.64 (d, 1H), 8.37 (s, 1H), 7.95 (d, 1H), 7.92 (d, 2H), 7.77 (d, 2H), 7.48 (s, 1H), 7.36 (d, 2H), 7.26-7.22 (m, 1H), 7.01-6.97 (m, 2H), 2.32 (s, 3H).
MS: (ESI+) MH+=468.29.

Cmpd 9
N-(2,6-Dimethoxy-phenyl)-4-[4-(2-fluoro-pyridin-3-yl)-5-methylsulfanyl-pyrimidin-2-ylamino]-benzamide
$^1$NMR (500 MHz, CDCl$_3$): 8.63 (s, 1H), 8.37 (d, 1H), 7.95-7.91 (m, 3H), 7.73-7.71 (d, 2H), 7.43 (d, 1H), 7.35 (d, 1H), 7.25 (d, 1H), 7.18 (d, 1H), 6.62 (s, 2H), 3.83 (s, 6H), 2.31 (s, 3H).
MS: (ESI+) MH+=492.28.

Cmpd 10
N-(2,6-Difluoro-phenyl)-4-(5-methylsulfanyl-4-pyridin-3-yl-pyrimidin-2-ylamino)-benzamide
$^1$NMR (500 MHz, CDCl$_3$): 9.10 (d, 1H), 8.73 (d, 1H), 8.60 (s, 1H), 8.20 (d, 1H), 7.93 (d, 2H), 7.80 (d, 2H), 7.52 (s, 1H), 7.45 (d, 2H), 7.26-7.22 (m, 1H), 7.01-6.97 (m, 2H), 2.30 (s, 3H).
MS: (ESI+) MH+=450.47.

Cmpd 11
4-[4-(2-Fluoro-pyridin-3-yl)-5-methylsulfanyl-pyrimidin-2-ylamino]-N-o-tolyl-benzamide
$^1$NMR (500 MHz, CDCl$_3$): 8.65 (s, 1H), 8.38 (d, 1H), 7.97-7.87 (m, 4H), 7.77 (d, 2H), 7.69 (s, 1H), 7.64 (s, 1H), 7.36-7.12 (m, 3H), 7.12 (d, 1H), 2.34 (s, 3H), 2.33 (s, 3H).
MS: (ESI+) MH+=446.21.

Cmpd 12
N-(2,6-Dimethyl-phenyl)-3-fluoro-4-[4-(2-fluoro-pyridin-3-yl)-5-methylsulfanyl-pyrimidin-2-ylamino]-benzamide
$^1$NMR (500 MHz, d-DMSO): 9.82 (s, 1H), 9.74 (s, 1H), 8.72 (s, 1H), 8.39 (s, 1H), 8.14 (d, 1H), 7.98 (d, 1H), 7.83 (d, 2H), 7.54 (d, 1H), 7.12 (s, 3H), 2.34 (s, 3H), 2.17 (s, 6H).
MS: (ESI+) MH+=478.34.

Cmpd 13
N-(2,6-Dimethoxy-phenyl)-3-fluoro-4-[4-(2-fluoro-pyridin-3-yl)-5-methylsulfanyl-pyrimidin -2-ylamino]-benzamide
$^1$NMR (500 MHz, d-DMSO): 9.78 (s, 1H), 9.32 (s, 1H), 8.72 (s, 1H), 8.39 (s, 1H), 8.14 (d, 1H), 7.96 (d, 1H), 7.81 (d, 2H), 7.54 (d, 1H), 7.26 (d, 1H), 6.71 (d, 2H), 3.72 (s, 6H), 2.34 (s, 3H).
MS: (ESI+) MH+=510.19.

Cmpd 14
4-[4-(2-Fluoro-pyridin-3-yl)-5-methylsulfanyl-pyrimidin-2-ylamino]-N-(2-methoxy-6-methyl -phenyl)-benzamide
$^1$NMR (500 MHz, d-DMSO): 10.30 (s, 1H), 9.37 (s, 1H), 8.78 (s, 1H), 8.41 (d, 1H), 8.18 (d, 1H), 7.94 (d, 2H), 7.86 (d, 2H), 7.57 (d, 1H), 7.18 (d, 1H), 6.90 (d, 1H), 6.86 (d, 1H), 3.72 (s, 3H), 2.35 (s, 3H), 1.98 (s, 3H).
MS: (ESI+) MH+=476.58.

Cmpd 15
3-Fluoro-4-[4-(2-fluoro-pyridin-3-yl)-5-methylsulfanyl-pyrimidin-2-ylamino]-N-(2-methoxy -6-methyl-phenyl)-benzamide
$^1$NMR (500 MHz, d-DMSO): 10.31 (s, 1H), 9.81 (s, 1H), 9.57 (s, 1H), 8.72 (s, 1H), 8.40 (d, 1H), 8.14 (d, 1H), 7.97 (d, 2H), 7.84 (d, 1H), 7.55 (d, 1H), 7.18 (d, 1H), 6.90 (dd, 2H), 3.73 (s, 3H), 2.35 (s, 3H), 1.98 (s, 3H).
MS: (ESI+) MH+=494.18.

Cmpd 16
3-Fluoro-4-[4-(2-fluoro-pyridin-3-yl)-5-methylsulfanyl-pyrimidin-2-ylamino]-N-o-tolyl-benzamide
$^1$NMR (500 MHz, CDCl$_3$): 8.66 (d, 2H), 8.38 (s, 1H), 7.97-7.91 (m, 2H), 7.73-7.61 (m, 4H), 7.37 (s, 1H), 7.23 (dd, 2H), 7.13 (d, 1H), 2.33 (s, 6H).
MS: (ESI+) MH+=464.22.

Cmpd 17
3-Fluoro-4-[4-(6-fluoro-pyridin-3-yl)-5-methylsulfanyl-pyrimidin-2-ylamino]-N-(2-methoxy -6-methyl-phenyl)-benzamide
$^1$NMR (500 MHz, CDCl$_3$): 8.78 (s, 1H), 8.65 (s, 1H), 8.62 (s, 1H) 8.34 (d, 1H), 7.72 (dd, 2H), 7.62 (d, 1H), 7.53 (s, 1H), 7.16 (d, 1H), 7.07 (d, 1H), 6.89 (d, 1H), 6.78 (d, 1H), 3.80 (s, 3H), 2.33 (s, 3H), 2.32 (s, 3H).
MS: (ESI+) MH+=494.17.

Cmpd 18
N-(4-Cyano-phenyl)-4-[4-(2-fluoro-pyridin-3-yl)-5-methylsulfanyl-pyrimidin-2-ylamino]-benzamide
$^1$NMR (500 MHz, d-DMSO): 10.45 (s, 1H), 10.38 (s, 1H), 8.78 (s, 1H), 8.42 (d, 1H), 8.19 (d, 1H), 7.97 (d, 2H), 7.93-7.88 (dd, 4H), 7.80 (d, 2H), 7.56 (s, 1H), 2.35 (s, 3H).
MS: (ESI+) MH+=457.05.

Cmpd 19
4-(5-Methylsulfanyl-4-phenyl-pyrimidin-2-ylamino)-N-o-tolyl-benzamide
$^1$NMR (500 MHz, CDCl$_3$): 8.54 (s, 1H), 7.97 (d, 1H), 7.88-7.79 (m, 6H), 7.64 (s, 1H), 7.52-7.51 (d, 3H), 7.47 (s, 1H), 7.26-7.22 (dd, 2H), 7.10 (s, 1H), 2.34 (s, 3H), 2.29 (s, 3H).
MS: (ESI+) MH+=427.40.

Cmpd 20
N-(2-Methyl-5-morpholin-4-ylmethyl-phenyl)-4-(5-methylsulfanyl-4-phenyl-pyrimidin-2-ylamino)-benzamide
$^1$NMR (500 MHz, CDCl$_3$): 8.54 (s, 1H), 7.93 (s, 1H), 7.88-7.79 (m, 6H), 7.62 (s, 1H), 7.50 (s, 3H), 7.46 (s, 1H), 7.18 (s, 1H), 7.07 (s, 1H), 3.70 (d, 4H), 3.49 (s, 2H), 2.46 (s, 4H), 2.32 (s, 3H), 2.29 (s, 3H).
MS: (ESI+) MH+=526.35.

Cmpd 21
N-(2,6-Dimethoxy-phenyl)-4-(5-methylsulfanyl-4-phenyl-pyrimidin-2-ylamino)-benzamide
$^1$NMR (500 MHz, CDCl$_3$): 8.54 (d, 1H), 7.2 (d, 2H), 7.83-7.77 (dd, 4H), 7.60 (s, 1H), 7.51 (s, 3H), 7.27 (s, 1H), 7.18 (s, 1H), 6.62 (d, 2H), 3.83 (s, 6H), 2.28 (s, 3H).
MS: (ESI+) MH+=473.24.

Cmpd 22
N-(2,6-Dimethoxy-phenyl)-4-[5-methylsulfanyl-4-(4-trifluoromethoxy-phenyl)-pyrimidin-2-ylamino]-benzamide
$^1$NMR (500 MHz, CDCl$_3$): 8.56 (d, 1H), 7.97-7.90 (dd, 4H), 7.75 (d, 2H), 7.39-7.18 (m, 5H), 6.62 (d, 2H), 3.83 (s, 6H), 2.29 (s, 3H).
MS: (ESI+) MH+=557.60.

Cmpd 23
4-[5-Methylsulfanyl-4-(4-trifluoromethoxy-phenyl)-pyrimidin-2-ylamino]-N-o-tolyl-benzamide
$^1$NMR (500 MHz, CDCl$_3$): 8.56 (s, 1H), 7.97 (d, 1H), 7.92-7.90 (dd, 4H), 7.79 (d, 2H), 7.63 (s, 1H), 7.43 (s, 1H), 7.35 (d, 2H), 7.28-7.22 (m, 3H), 7.10 (d, 1H), 2.35 (s, 3H), 2.30 (s, 3H).
MS: (ESI+) MH+=511.20.

Cmpd 24
N-(2-Methyl-5-morpholin-4-ylmethyl-phenyl)-4-[5-methylsulfanyl-4-(4-trifluoromethoxy-phenyl) -pyrimidin-2-ylamino]-benzamide
$^1$NMR (500 MHz, CDCl$_3$): 8.56 (s, 1H), 7.92-7.87 (m, 5H), 7.80 (d, 2H), 7.62 (s, 1H), 7.42 (d, 1H), 7.36 (d, 2H), 7.18 (d, 1H), 7.08 (d, 1H), 3.70 (t, 4H), 3.49 (s, 2H), 2.46 (s, 4H), 2.32 (s, 3H), 2.30 (s, 3H).
MS: (ESI+) MH+=610.42.

Cmpd 25
N-(2-Methoxy-6-methyl-phenyl)-4-[5-methylsulfanyl-4-(4-trifluoromethoxy-phenyl)-pyrimidin -2-ylamino]-benzamide
$^1$NMR (500 MHz, CDCl$_3$): 8.56 (d, 1H), 7.94-7.90 (dd, 4H), 7.77 (d, 2H), 7.53 (s, 1H), 7.41 (s, 1H), 7.33 (d, 2H), 7.15 (d, 1H), 6.90 (d, 1H), 6.77 (d, 1H), 3.80 (s, 6H), 2.30 (s, 3H), 2.29 (s, 3H).
MS: (ESI+) MH+=541.15.

Cmpd 26
N-(2-Methyl-5-morpholin-4-ylmethyl-phenyl)-4-(5-methylsulfanyl-4-pyridin-4-yl-pyrimidin -2-ylamino)-benzamide
$^1$NMR (500 MHz, CDCl$_3$): 8.79 (d, 2H), 8.60 (s, 1H), 7.91-7.78 (m, 3H), 7.79-7.73 (dd, 4H), 7.65 (s, 1H), 7.53 (s, 1H), 7.18 (d, 1H), 7.08 (d, 1H), 3.70 (d, 4H), 3.49 (s, 2H), 2.46 (s, 4H), 2.32 (s, 3H), 2.30 (s, 3H).
MS: (ESI+) MH+=527.59.

Cmpd 27
N-(2-Methyl-5-morpholin-4-ylmethyl-phenyl)-4-[5-methylsulfanyl-4-(4-trifluoromethyl-phenyl) -pyrimidin-2-ylamino]-benzamide
$^1$NMR (500 MHz, CDCl$_3$): 8.59 (s, 1H), 7.95-7.89 (m, 3H), 7.87 (d, 2H), 7.78 (dd, 4H), 7.62 (s, 1H), 7.47 (s, 1H), 7.26 (s, 1H), 7.18 (d, 1H), 7.08 (d, 1H), 3.71 (d, 4H), 3.499 (s, 2H), 2.46 (s, 4H), 2.32 (s, 3H), 2.29 (s, 3H).
MS: (ESI+) MH+=594.20.

Cmpd 28
N-(2-Methyl-5-piperidin-1-ylmethyl-phenyl)-4-[5-methylsulfanyl-4-(4-trifluoromethyl-phenyl) -pyrimidin-2-ylamino]-benzamide
$^1$NMR (500 MHz, d-DMSO): 10.25 (s, 1H), 9.70 (s, 1H), 8.79 (s, 1H), 7.96-7.89 (m, 4H), 7.58 (d, 1H), 7.43 (d, 1H), 7.06 (d, 1H), 7.04 (d, 1H), 7.02 (d, 3H), 3.43 (s, 2H), 2.40 (b, 4H), 2.30 (b, 7H), 1.25 (b, 2H).
MS: (ESI+) MH+=592.24.

Cmpd 29
N-(2,6-Dimethyl-phenyl)-4-[4-(4-fluoro-phenyl)-5-methylsulfanyl-pyrimidin-2-ylamino]-benzamide
$^1$NMR (500 MHz, CDCl$_3$): 8.55 (s, 1H), 7.92 (d, 2H), 7.88 (d, 2H), 7.79 (d, 2H), 7.40 (s, 1H), 7.30 (s, 1H), 7.33 (d, 1H), 7.20 (d, 1H), 7.13 (t, 3H), 2.29 (s, 9H).
MS: (ESI+) MH+=459.10.

Cmpd 30
4-[4-(4-Fluoro-phenyl)-5-methylsulfanyl-pyrimidin-2-ylamino]-N-(2-methyl-5-morpholin-4-ylmethyl -phenyl)-benzamide
$^1$NMR (500 MHz, CDCl$_3$): 8.54 (s, 1H), 7.93 (s, 1H), 7.86 (dd, 4H), 7.79 (d, 2H), 7.62 (s, 1H), 7.42 (s, 1H), 7.18 (d, 3H), 7.08 (d, 1H), 3.70 (d, 4H), 3.49 (s, 2H), 2.46 (s, 4H), 2.32 (s, 3H), 2.29 (s, 3H).
MS: (ESI+) MH+=544.45.

Cmpd 31
N-(5-Dimethylaminomethyl-2-methyl-phenyl)-4-[4-(4-fluoro-phenyl)-5-methylsulfanyl-pyrimidin -2-ylamino]-benzamide
$^1$NMR (500 MHz, d-DMSO): 10.18 (s, 1H), 9.69 (s, 1H), 8.67 (s, 1H), 7.84 (d, 3H), 7.78 (s, 1H), 7.56 (d, 1H), 7.43 (d, 2H), 7.26 (d, 1H), 7.04 (d, 1H), 7.00 (d, 2H), 3.34 (s, 2H), 2.35 (s, 6H), 2.20 (s, 3H), 2.13 (s, 3H).
MS: (ESI+) MH+=502.53.

Cmpd 32
N-(5-Dimethylaminomethyl-2-methyl-phenyl)-4-[5-methylsulfanyl-4-(4-trifluoromethyl-phenyl) -pyrimidin-2-ylamino]-benzamide
$^1$NMR (500 MHz, CDCl$_3$): 8.59 (s, 1H), 7.95 (d, 2H), 7.88 (d, 3H), 7.78 (dd, 4H), 7.62 (s, 1H), 7.46 (s, 1H), 7.19 (d, 1H), 7.09 (d, 1H), 3.45 (s, 2H), 2.32 (s, 3H), 2.29 (s, 6H), 2.26 (s, 3H).
MS: (ESI+) MH+=552.23.

Cmpd 33
4-[4-(4-Cyano-phenyl)-5-methylsulfanyl-pyrimidin-2-ylamino]-N-(2-methyl-5-morpholin-4-ylmethyl -phenyl)-benzamide
$^1$NMR (500 MHz, CDCl$_3$): 8.60 (S, 1H), 7.96-7.96 (m, 2H), 7.87 (d, 2H), 7.80 (dd, 4H), 7.62 (s, 1H), 7.45 (s, 1H), 7.19 (d, 1H), 7.09 (d, 1H), 7.08 (d, 1H), 3.70 (d, 4H), 3.50 (s, 2H), 2.46 (s, 4H), 2.32 (s, 3H), 2.30 (s, 3H).
MS: (ESI+) MH+=551.35.

Cmpd 34
4-[4-(4-Cyano-phenyl)-5-methylsulfanyl-pyrimidin-2-ylamino]-N-(5-dimethylaminomethyl-2-methyl-phenyl)-benzamide
$^1$NMR (500 MHz, CDCl$_3$): 8.57 (s, 1H), 7.93 (d, 2H), 7.86 (d, 3H), 7.84 (d, 2H), 7.77 (d, 2H), 7.61 (s, 1H), 7.46 (s, 1H), 7.17 (d, 1H), 7.07 (d, 1H), 3.42 (s, 2H), 2.29 (s, 3H), 2.27 (s, 6H), 2.42 (s, 3H).
MS: (ESI+) MH+=508.87.

Cmpd 35
4-[4-(4-Cyano-phenyl)-5-methylsulfanyl-pyrimidin-2-ylamino]-N-[2-methyl-5-(4-methyl-piperazin -1-ylmethyl)-phenyl]-benzamide
$^1$NMR (500 MHz, CDCl$_3$): 8.59 (s, 1H), 7.93 (d, 2H), 7.87 (d, 3H), 7.82 (d, 2H), 7.78 (d, 2H), 7.62 (s, 1H), 7.45 (s, 1H), 7.16 (d, 1H), 7.05 (d, 1H), 3.51 (d, 2H), 2.58 (b, 4H), 2.43 (s, 4H), 2.30 (s, 6H), 2.27 (s, 3H).
MS: (ESI+) MH+=564.25.

Cmpd 36
4-[4-(4-Fluoro-phenyl)-5-methylsulfanyl-pyrimidin-2-ylamino]-N-[2-methyl-5-(4-methyl-piperazin -1-ylmethyl)-phenyl]-benzamide
$^1$NMR (500 MHz, CDCl$_3$): 8.54 (s, 1H), 7.88 (dd, 4H), 7.80 (d, 2H), 7.62 (s, 1H), 7.44 (s, 2H), 7.21 (m, 3H), 7.07 (d, 1H), 3.50 (s, 2H), 2.49 (b, 4H), 2.31 (s, 3H), 2.29 (s, 6H), 1.94 (b, 4H).
MS: (ESI+) MH+=557.56.

Cmpd 37
N-[2-Methyl-5-(4-methyl-piperazin-1-ylmethyl)-phenyl]-4-[5-methylsulfanyl-4-(4-trifluoromethoxy -phenyl)-pyrimidin-2-ylamino]-benzamide
$^1$NMR (500 MHz, CDCl$_3$): 8.56 (s, 1H), 7.90 (d, 2H), 7.88 (d, 2H), 7.78 (d, 2H), 7.64 (s, 1H), 7.53 (s, 1H), 7.34 (d, 2H), 7.16 (d, 1H), 7.08 (d, 1H), 3.49 (s, 2H), 2.48 (b, 4H), 2.40 (s, 3H), 2.29 (s, 3H), 2.27 (s, 3H), 2.04 (b, 4H).
MS: (ESI+) MH+=623.41.

Cmpd 38
4-[5-Methoxy-4-(4-trifluoromethoxy-phenyl)-pyrimidin-2-ylamino]-N-(2-methyl-5-morpholin-4-ylmethyl-phenyl)-benzamide
$^1$NMR (500 MHz, CDCl$_3$): 8.32 (s, 1H), 8.21-8.25 (m, 5H), 8.09 (d, 1H), 7.89 (d, 2H), 7.53 (t, 1H), 7.48 (d, 1H), 7.42 (t, 1H), 7.34 (d, 2H), 3.97 (s, 3H).
MS: (ESI+) MH+=594.61.

Cmpd 39
N-(2-Methyl-5-morpholin-4-ylmethyl-phenyl)-4-[4-(1-methyl-1H-pyrazol-4-yl)-5-methylsulfanyl -pyrimidin-2-ylamino]-benzamide
$^1$NMR (500 MHz, CDCl$_3$): 8.50 (s, 1H), 8.46 (d, 2H), 7.93 (s, 1H), 7.90 (d, 2H), 7.66 (s, 2H), 7.41 (s, 1H), 7.25 (s, 1H), 7.19 (d, 1H), 7.09 (d, 1H), 4.00 (s, 3H), 3.70 (s, 4H), 3.50 (s, 2H), 2.46 (s, 4H), 2.38 (s, 3H), 2.33 (s, 3H).
MS: (ESI+) MH+=530.55.

Cmpd 40
3-Fluoro-N-(2-methyl-5-morpholin-4-ylmethyl-phenyl)-4-[5-methylsulfanyl-4-(4-trifluoromethoxy -phenyl)-pyrimidin-2-ylamino]-benzamide
$^1$NMR (500 MHz, CDCl$_3$): 8.72 (d, 1H), 8.71 (s, 1H), 7.90 (t, 3H), 7.73 (d, 1H), 7.66-7.60 (m, 3H), 7.37 (d, 2H), 7.19 (d, 1H), 7.10 (d, 1H), 3.70 (t, 4H), 3.49 (s, 2H), 2.60 (s, 4H), 2.30 (s, 6H).
MS: (ESI+) MH+=628.33.

Cmpd 41
3-Fluoro-4-[4-(4-fluoro-phenyl)-5-methylsulfanyl-pyrimidin-2-ylamino]-N-(2-methyl-5-morpholin-4-ylmethyl-phenyl)-benzamide
$^1$NMR (500 MHz, CDCl$_3$): 8.75 (d, 1H), 8.56 (s, 1H), 7.88 (d, 3H), 7.72 (s, 1H), 7.65-7.60 (m, 3H), 7.22-7.17 (m, 3H), 7.10 (d, 1H), 3.70 (t, 4H), 3.49 (s, 2H), 2.45 (s, 4H), 2.32 (s, 6H).
MS: (ESI+) MH+=562.32.

Cmpd 42
3-Fluoro-4-[4-(4-fluoro-phenyl)-5-methylsulfanyl-pyrimidin-2-ylamino]-N-(2-methyl-5-piperidin -1-ylmethyl-phenyl)-benzamide
$^1$NMR (500 MHz, CDCl$_3$): 8.71 (d, 1H), 8.54 (s, 1H), 7.88 (d, 2H), 7.78 (s, 1H), 7.71-7.76 (m, 4H), 7.21-7.15 (m, 3H), 7.09 (s, 1H), 3.47 (s, 2H), 2.40 (b, 4H), 2.30 (s, 3H), 1.58 (b, 4H), 1.42 (b, 2H), 1.25 (s, 3H).
MS: (ESI+) MH+=560.54.

Cmpd 43
4-[4-(4-Fluoro-phenyl)-5-methylsulfanyl-pyrimidin-2-ylamino]-N-(3-morpholin-4-ylmethyl-phenyl) -benzamide
$^1$NMR (500 MHz, CDCl$_3$): 8.54 (d, 1H), 7.88-7.85 (dd, 4H), 7.80-77 (m, 3H), 7.59 (d, 2H), 7.45 (s, 1H), 7.33 (s, 1H), 7.21 (d, 2H), 7.10 (d, 1H), 3.71 (t, 4H), 3.50 (s, 2H), 2.46 (s, 4H), 2.29 (s, 3H).
MS: (ESI+) MH+=530.59.

Cmpd 44
3-Fluoro-4-[5-methylsulfanyl-4-(4-trifluoromethoxy-phenyl)-pyrimidin-2-ylamino]-N-(3-morpholin -4-ylmethyl-phenyl)-benzamide
$^1$NMR (500 MHz, CDCl$_3$): 8.71 (d, 1H), 8.57 (s, 1H), 7.90 (d, 2H), 7.81 (s, 1H), 7.71 (d, 1H), 7.69 (d, 2H), 7.65 (d, 2H), 7.36-7.25 (m, 3H), 7.11 (d, 1H), 3.71 (t, 4H), 3.50 (s, 2H), 2.46 (s, 4H), 2.32 (s, 3H).
MS: (ESI+) MH+=614.27.

Cmpd 45
3-Fluoro-N-(2-methyl-5-morpholin-4-ylmethyl-phenyl)-4-[4-(1-methyl-1H-pyrazol-4-yl)-5-methylsulfanyl -pyrimidin-2-ylamino]-benzamide
$^1$NMR (500 MHz, CDCl$_3$): 8.73 (d, 1H), 8.51 (s, 1H), 8.47 (s, 1H), 8.44 (s, 1H), 7.89 (s, 1H), 7.72-7.65 (m, 3H), 7.53 (d, 1H), 7.18 (d, 1H), 7.09 (d, 1H), 4.00 (s, 3H), 3.70 (s, 4H), 3.50 (s, 2H), 2.46 (s, 4H), 2.39 (s, 3H), 2.33 (s, 3H).
MS: (ESI+) MH+=548.23.

Cmpd 46
3-Fluoro-N-[2-methyl-5-(4-methyl-piperazin-1-ylmethyl)-phenyl]-4-[4-(1-methyl-1H-pyrazol -4-yl)-5-methylsulfanyl-pyrimidin-2-ylamino]-benzamide
$^1$NMR (500 MHz, CDCl$_3$): 8.76 (d, 1H), 8.51 (s, 1H), 8.47 (s, 1H), 8.44 (s, 1H), 7.90 (s, 1H), 7.73-7.68 (m, 3H), 7.53 (d, 1H), 7.18 (d, 1H), 7.09 (d, 1H), 4.01 (s, 3H), 3.57 (s, 2H), 2.74 (b, 4H), 2.46 (s, 4H), 2.37 (s, 3H), 2.40 (s, 3H), 2.33 (s, 3H).
MS: (ESI+) MH+=561.38.

Cmpd 47
N-(5-Diethylaminomethyl-2-methyl-phenyl)-4-[4-(4-fluoro-phenyl)-5-methylsulfanyl-pyrimidin -2-ylamino]-benzamide
$^1$NMR (500 MHz, CDCl$_3$): 8.54 (s, 1H), 7.91-7.86 (m, 5H), 7.80 (d, 2H), 7.66 (s, 1H), 7.41 (s, 1H), 7.21-7.14 (m, 4H), 3.65 (s, 2H), 2.62 (b, 4H), 2.32 (s, 3H), 2.26 (s, 3H), 1.10 (d, 6H).
MS: (ESI+) MH+=530.65.

Cmpd 48
4-[4-(4-Fluoro-phenyl)-5-methylsulfanyl-pyrimidin-2-ylamino]-N-(2-methyl-5-piperidin-1-ylmethyl -phenyl)-benzamide
$^1$NMR (500 MHz, CDCl$_3$): 8.54 (s, 1H), 7.88-7.86 (m, 5H), 7.78 (d, 2H), 7.63 (s, 1H), 7.47 (s, 1H), 7.21-7.16 (m, 3H), 7.10 (d, 1H), 3.49 (s, 2H), 2.41 (b, 4H), 2.31 (s, 3H), 2.29 (s, 3H), 1.58 (b, 4H), 1.42 (b, 2H).
MS: (ESI+) MH+=542.34.

Cmpd 49
4-((4-(4-cyanophenyl)-5-methoxypyrimidin-2-ylamino)-N-(2-methyl-5-(morpholinomethyl)phenyl)benzamide
$^1$NMR (500 MHz, CD$_3$OD): 8.44 (s, 1H), 8.24 (d, 2H), 7.97 (d, 2H), 7.789 (t, 4H), 7.32 (s, 1H), 7.24 (d, 1H), 7.16 (d, 1H), 3.94 (s, 3H), 3.67 (t, 4H), 3.51 (s, 2H), 2.45 (s, 4H), 2.29 (s, 3H)
MS: (ESI+) MH+=535.62.

Cmpd 50
4-((4-(4-cyanophenyl)-5-methoxypyrimidin-2-yl)amino)-N-(5-((diethylamino)methyl)-2-methylphenyl)benzamide
$^1$NMR (500 MHz, CD$_3$OD): 8.44 (s, 1H), 8.24 (d, 2H), 7.97 (d, 2H), 7.789 (t, 4H), 7.32 (s, 1H), 7.24 (d, 1H), 7.16 (d, 1H), 3.94 (s, 3H), 3.67 (t, 2H), 3.51 (s, 2H), 2.45 (s, 2H), 2.29 (s, 3H), 1.23 (s, 6H)
MS: (ESI+) MH+=521.64.

Cmpd 51
4-((4-(4-cyanophenyl)-5-methoxypyrimidin-2-yl)amino)-N-(2-methyl-5-((4-methylpiperazin -1-yl)methyl)phenyl)benzamide
$^1$NMR (500 MHz, CD$_3$OD): 8.45 (s, 1H), 8.30 (d, 1H), 7.86-792 (m, 4H), 7.82 (d, 1H), 7.65-7.68 (q, 3H), 7.31 (s, 1H), 7.24-7.26 (m, 1H), 7.16 (s, 1H), 3.93 (d, 3H), 3.52 (s, 2H), 3.41 (s, 3H), 3.30-3.34 (m, 4H), 2.50 (s, 3H), 2.28-2.30 (t, 4H)
MS: (ESI+) MH+=548.66.

Cmpd 52
4-[5-Methoxy-4-(4-trifluoromethoxy-phenyl)-pyrimidin-2-ylamino]-N-[2-methyl-5-(4-methyl -piperazin-1-ylmethyl)-phenyl]-benzamide
$^1$NMR (500 MHz, CD$_3$OD): 8.62-8.63 (t, 1H), 8.40 (m, 1H), 8.20-8.23 (m, 2H), 7.75-7.81 (m, 2H), 7.30 (s, 1H), 7.16-7.26 (m, 4H), 3.92 (s, 3H), 3.5 (s, 2H), 3.30-3.34 (m, 8H), 2.29 (s, 3H), 2.28 (s, 3H)
MS: (ESI+) MH+=607.65.

Cmpd 53
N-(5-Diethylaminomethyl-2-methyl-phenyl)-3-fluoro-4-[4-(4-fluoro-phenyl)-5-methylsulfanyl -pyrimidin-2-ylamine]-benzamide
¹NMR (500 MHz, CDCl₃): 8.72 (t, 1H), 8.55 (s, 1H), 7.88-7.83 (m, 3H), 7.72 (d, 1H), 7.65 (d, 3H), 7.25-7.17 (m, 3H), 7.13 (d, 1H), 3.58 (s, 2H), 2.56 (d, 4H), 2.30 (s, 6H), 1.06 (d, 6H).
MS: (ESI+) MH+=548.25.

Cmpd 54
N-(5-Dimethylaminomethyl-2-methyl-phenyl)-4-[5-methylsulfanyl-4-(4-trifluoromethoxy-phenyl) -pyrimidin-2-ylamino]-benzamide
¹NMR (500 MHz, CDCl₃): 8.56 (s, 1H), 8.03 (s, 1H), 7.91-7.88 (m, 5H), 7.80 (d, 2H), 7.49 (s, 1H), 7.36-7.25 (m, 4H), 3.89 (s, 2H), 2.58 (d, 6H), 2.37 (s, 3H), 2.16 (s, 3H).
MS: (ESI+) MH+=568.09.

Cmpd 55
3-Fluoro-N-(2-fluoro-5-morpholin-4-ylmethyl-phenyl)-4-[5-methylsulfanyl-4-(4-trifluoromethoxy -phenyl)-pyrimidin-2-ylamino]-benzamide
¹NMR (500 MHz, CDCl₃): 8.73 (d, 1H), 8.58 (s, 1H), 8.40 (d, 1H), 7.99 (s, 1H), 7.91 (d, 2H), 7.74 (d, 1H), 7.65 (d, 2H), 7.36 (d, 2H), 7.08 (d, 2H), 3.71 (t, 4H), 3.49 (s, 2H), 2.46 (s, 4H), 2.32 (s, 3H).
MS: (ESI+) MH+=632.26.

Cmpd 56
N-(3-Diethylaminomethyl-phenyl)-3-fluoro-4-[5-methylsulfanyl-4-(4-trifluoromethoxy-phenyl) -pyrimidin-2-ylamino]-benzamide
¹NMR (500 MHz, CDCl₃): 8.72 (s, 1H), 8.58 (s, 1H), 7.91 (d, 2H), 7.82 (s, 1H), 7.72-7.63 (m, 3H), 7.50 (s, 1H), 7.37-7.26 (m, 3H), 7.10 (d, 1H), 3.58 (s, 2H), 2.56 (d, 2H), 2.53 (d, 2H), 2.32 (s, 3H), 1.05 (d, 6H).
MS: (ESI+) MH+=600.35.

Cmpd 57
3-Fluoro-N-(2-fluoro-5-morpholin-4-ylmethyl-phenyl)-4-[4-(4-fluoro-phenyl)-5-methylsulfanyl -pyrimidin-2-ylamino]-benzamide
¹NMR (500 MHz, CDCl₃): 8.76 (s, 1H), 8.56 (s, 1H), 8.40 (s, 1H), 7.99 (d, 1H), 7.87 (dd, 2H), 7.72 (d, 1H), 7.63 (d, 2H), 7.26-7.19 (m, 2H), 7.08 (d, 2H), 3.71 (t, 4H), 3.50 (s, 2H), 2.46 (s, 4H), 2.32 (s, 3H).
MS: (ESI+) MH+=566.14.

Cmpd 58
3-Fluoro-N-(2-methoxy-5-morpholin-4-ylmethyl-phenyl)-4-[5-methylsulfanyl-4-(4-trifluoromethoxy -phenyl)-pyrimidin-2-ylamino]-benzamide
¹NMR (500 MHz, CDCl₃): 8.73 (d, 1H), 8.57 (s, 1H), 8.47 (d, 2H), 7.91 (d, 2H), 7.73-7.61 (m, 3H), 7.36 (d, 2H), 7.05 (d, 1H), 6.87 (d, 1H), 3.93 (s, 3H), 3.71 (t, 4H), 3.48 (s, 2H), 2.46 (s, 4H), 2.32 (s, 3H).
MS: (ESI+) MH+=644.23.

Cmpd 59
4-[4-(4-Fluoro-phenyl)-5-methylsulfanyl-pyrimidin-2-ylamino]-N-(2-methoxy-5-morpholin-4-ylmethyl-phenyl)-benzamide
¹NMR (500 MHz, CDCl₃): 8.54 (s, 1H), 8.49 (d, 2H), 7.90-7.86 (m, 4H), 7.79 (d, 2H), 7.41 (s, 1H), 7.20 (s, 2H), 7.04 (d, 1H), 6.86 (d, 1H), 3.93 (s, 3H), 3.71 (t, 4H), 3.48 (s, 2H), 2.46 (s, 4H), 2.29 (s, 3H).

Cmpd 60
4-((4-(4-fluorophenyl)-5-(methoxypyrimidin-2-yl)amino)-N-(2-methyl-5-(morpholinomethyl)phenyl)benzamide
¹NMR (500 MHz, CD₃OD): 8.62 (t, 1H), 8.32 (d, 1H), 8.16-8.19 (m, 2H), 7.73-7.78 (m, 2H), 7.30 (s, 1H), 7.23 (d, 1H), 7.15 (t, 3H), 3.89 (d, 3H), 3.66 (m, 4H), 3.48 (s, 2H), 2.45 (s, 4H), 2.27 (s, 3H)
MS: (ESI+) MH+=546.59.

Cmpd 61
N-(5-Diethylaminomethyl-2-methyl-phenyl)-4-[5-methoxy-4-(4-trifluoromethoxy-phenyl)-pyrimidin -2-ylamino]-benzamide
¹NMR (500 MHz, CD₃OD): 8.40 (s, 1H), 8.26 (d, 2H), 7.94 (d, 2H), 7.89 (d, 2H), 7.50 (s, 1H), 7.36 (d, 3H), 7.29-7.31 (m, 1H), 4.41 (s, 2H), 3.93 (s, 3H), 3.04-3.08 (m, 3H), 2.34 (s, 3H), 1.22-1.30 (m, 6H)
MS: (ESI+) MH+=598.61.

Cmpd 62
4-[5Methoxy-4-(4-trifluoromethoxy-phenyl)-pyrimidin-2-ylamino]-N-[2-methyl-5-(4-methyl-piperazin -1-ylmethyl)-phenyl]-benzamide
¹NMR (500 MHz, CD₃OD): 8.62-8.63 (t, 1H), 8.40 (m, 1H), 8.20-8.23 (m, 2H), 7.75-7.81 (m, 2H), 7.30 (s, 1H), 7.16-7.26 (m, 4H), 3.92 (s, 3H), 3.5 (s, 2H), 3.30-3.34 (m, 8H), 2.29 (s, 3H), 2.28 (s, 3H)
MS: (ESI+) MH+=625.64.

Cmpd 63
N-(2-Methyl-5-morpholin-4-ylmethyl-phenyl)-6-[5-methylsulfanyl-4-(4-trifluoromethoxy-phenyl) -pyrimidin-2-ylamino]-nicotinamide
¹NMR (500 MHz, CDCl₃): 8.95 (s, 1H), 8.91 (s, 1H), 8.65 (s, 1H), 8.56 (d, 1H), 8.20 (d, 1H), 7.91 (d, 2H), 7.87 (s, 1H), 7.60 (s, 1H), 7.34 (d, 2H), 7.18 (d, 1H), 7.10 (d, 1H), 3.71 (t, 4H), 3.49 (s, 2H), 2.46 (s, 4H), 2.32 (s, 6H).
MS: (ESI+) MH+=611.83.

Cmpd 64
6-[5-Methylsulfanyl-4-(4-trifluoromethoxy-phenyl)-pyrimidin-2-ylamino]-N-(3-morpholin-4-ylmethyl-phenyl)-nicotinamide
¹NMR (500 MHz, CDCl₃): 8.86 (d, 1H), 8.66 (s, 1H), 8.63 (s, 1H), 8.55 (d, 1H), 8.20 (dd, 1H), 7.91 (d, 2H), 7.77 (s, 1H), 7.58 (d, 2H), 7.36-7.26 (m, 3H), 7.13 (s, 1H), 3.71 (t, 4H), 3.51 (s, 2H), 2.46 (s, 4H), 2.31 (s, 3H).
MS: (ESI+) MH+=597.62.

Cmpd 65
4-[5-Methylsulfanyl-4-(4-trifluoromethoxy-phenyl)-pyrimidin-2-ylamino]-N-(3-morpholin-4-ylmethyl-phenyl)-benzamide
¹NMR (500 MHz, CDCl₃): 8.56 (d, 1H), 7.91-7.86 (m, 4H), 7.79 (d, 2H), 7.77 (s, 1H), 7.59 (s, 2H), 7.44 (s, 1H), 7.35-7.25 (m, 3H), 7.11 (d, 2H), 3.71 (t, 4H), 3.50 (s, 2H), 2.46 (s, 4H), 2.30 (s, 3H).
MS: (ESI+) MH+=596.30.

Cmpd 66
N-(5-Diethylaminomethyl-2-methyl-phenyl)-6-[5-methylsulfanyl-4-(4-trifluoromethoxy-phenyl) -pyrimidin-2-ylamino]-nicotinamide
¹NMR (500 MHz, CDCl₃): 8.96 (s, 1H), 8.92 (s, 1H), 8.65 (s, 1H), 8.56 (d, 1H), 8.21 (d, 1H), 7.92 (d, 2H), 7.83 (s, 1H), 7.66 (s, 1H), 7.36 (d, 2H), 7.18 (dd, 2H), 3.63 (s, 2H), 2.58 (dd, 4H), 2.32 (s, 3H), 2.31 (s, 3H), 1.08 (t, 6H).
MS: (ESI+) MH+=597.26.

Cmpd 67
4-[4-(6-Fluoro-pyridin-3-yl)-5-methylsulfanyl-pyrimidin-2-ylamino]-N-(2-methyl-5-morpholin-4-ylmethyl-phenyl)benzamide
¹NMR (500 MHz, CDCl₃): 8.78 (d, 1H), 8.60 (s, 1H), 8.34 (d, 1H), 7.93 (s, 1H), 7.87 (d, 2H), 7.78 (d, 2H), 7.64 (s, 1H), 7.51 (s, 1H), 7.18 (d, 1H), 7.07 (dd, 2H), 3.70 (t, 4H), 3.49 (s, 2H), 2.46 (s, 4H), 2.32 (s, 3H), 2.30 (s, 3H).
MS: (ESI+) MH+=545.49.

Cmpd 68
N-(2-Methyl-5-morpholin-4-ylmethyl-phenyl)-4-[5-methylsulfanyl-4-(6-trifluoromethyl-pyridin-3-yl)-pyrimidin-2-ylamino]-benzamide
¹NMR (500 MHz, CDCl₃): 9.19 (s, 1H), 8.63 (s, 1H), 8.38 (d, 1H), 7.94 (s, 1H), 7.87-7.86 (m, 2H), 7.82-7.75 (m, 5H), 7.21 (d, 2H), 3.70 (t,4H), 3.49 (s, 2H), 2.46 (s, 4H), 2.32 (s, 3H), 2.30 (s, 3H).
MS: (ESI+) MH+=595.34.

Cmpd 69
4-[5-Methylsulfanyl-4-(6-trifluoromethyl-pyridin-3-yl)-pyrimidin-2-ylamino]-N-(3-morpholin-4-ylmethyl-phenyl)benzamide
¹NMR (500 MHz, CDCl₃): 9.21 (s, 1H), 8.64 (s, 1H), 8.40 (dd, 1H), 7.88 (d, 2H), 7.83 (d, 2H), 7.78 (d, 2H), 7.60 (d, 2H), 7.58 (s, 1H), 7.33 (dd, 1H), 7.11 (d, 1H), 3.71 (t, 4H), 3.49 (s, 2H), 2.46 (s, 4H), 2.32 (s, 3H).
MS: (ESI+) MH+=581.47.

Cmpd 70
N-(2-Fluoro-5-morpholin-4-ylmethyl-phenyl)-4-[5-methylsulfanyl-4-(4-trifluoromethoxy-phenyl)-pyrimidin-2-ylamino]-benzamide
¹NMR (500 MHz, CDCl₃): 8.56 (s, 1H), 8.44 (d, 1H), 8.02 (s, 1H), 7.90 (dd, 4H), 7.80 (d, 2H), 7.43 (s, 1H), 7.36 (d, 2H), 7.08 (d, 2H), 3.71 (t, 4H), 3.49 (s, 2H), 2.46 (s, 4H), 2.32 (s, 3H).
MS: (ESI+) MH+=614.37.

Cmpd 71
N-(2-Fluoro-5-morpholin-4-ylmethyl-phenyl)-4-[4-(4-fluoro-phenyl)-5-methylsulfanyl-pyrimidin-2-ylamino]benzamide
¹NMR (500 MHz, CDCl₃): 8.55 (s, 1H), 8.44 (d, 1H), 8.01 (s, 1H), 7.88 (dd, 4H), 7.80 (d, 2H), 7.41 (s, 1H), 7.20 (d, 2H), 7.08 (d, 2H), 3.71 (t, 4H), 3.49 (s, 2H), 2.46 (s, 4H), 2.29 (s, 3H).
MS: (ESI+) MH+=548.36.

Cmpd 72
3-fluoro-N-(2-fluoro-5-((4-methylpiperazin-1-yl)methyl)phenyl)-4-((5-methoxy-4-(4-(trifluoromethoxy)phenyl)pyrimidin-2-yl)amino)benzamide
¹NMR (500 MHz, CDCl₃): 8.28 (s, 1H), 8.23 (d, 2H), 7.94 (s, 1H), 7.87 (d, 2H), 7.71 (d, 2H), 7.65 (s, 1H), 7.32 (t, 3H), 7.18 (d, 1H), 7.09 (d, 1H), 4.10 (m, 2H), 3.72 (s, 4H), 3.53 (s, 2H), 2.49 (s, 4H), 2.33 (s, 3H), 1.44 (t, 3H)
MS: (ESI+) MH+=608.63.

Cmpd 73
4-((5-ethoxy-4-(4-(trifluoromethoxy)phenyl)pyrimidin-2-yl)amino)-N-(2-methyl-5-((4-methylpiperazin-1-yl)methyl)phenyl)benzamide
¹NMR (500 MHz, CDCl₃): 8.27 (s, 1H), 8.23 (d, 2H), 7.8 (d, 3H), 7.76 (d, 2H), 7.66 (s, 1H), 7.41 (s, 1H), 7.32 (s, 2H), 7.16 (d, 1H), 7.06 (d, 1H), 4.09 (m, 2H), 3.50 (s, 2H), 2.48 (m, 6H), 2.32 (s, 4H), 2.28 (s, 3H), 1.43 (t, 3H)
MS: (ESI+) MH+=621.68.

Cmpd 74
N-(5-((diethylamino)methyl)-2-methylphenyl)-4-((5-ethoxy-4-(4-(trifluoromethoxy)phenyl)pyrimidin-2-yl)amino)benzamide
¹NMR (500 MHz, CD₃OD): 8.40 (s, 1H), 8.26 (d, 2H), 7.94 (d, 2H), 7.89 (d, 2H), 7.50 (s, 1H), 7.36 (d, 3H), 7.29 (t, 1H), 4.14 (s, 2H), 3.93 (s, 3H), 3.59 (s, 2H), 3.04 (s, 4H), 1.22 (m, 6H)
MS: (ESI+) MH+=594.65.

Cmpd 75
4-((5-ethoxy-4-(4-fluorophenyl)pyrimidin-2-yl)amino)-N-(2-methyl-5-(morpholinomethyl)phenyl)benzamide
¹NMR (500 MHz, CDCl₃): 8.25 (s, 1H), 8.19 (m, 2H), 7.93 (s, 1H), 7.88 (d, 2H), 7.66 (s, 1H), 7.38 (s, 1H), 7.16 (t, 3H), 6.97 (d, 1H), 3.71 (t, 4H), 3.51 (s, 2H), 2.47 (s, 4H), 2.32 (s, 3H)
MS: (ESI+) MH+=542.63.

Cmpd 76
4-((5-ethoxy-4-(4-fluorophenyl)pyrimidin-2-yl)amino)-N-(2-methyl-5-((4-methylpiperazin-1-yl)methyl)phenyl)benzamide
¹NMR (500 MHz, CD₃OD): 8.65 (t, 1H), 8.40 (s, 1H), 8.20 (m, 2H), 7.75 (m, 2H), 7.30 (s, 1H), 7.16 (m, 4H), 4.44 (s, 2H), 3.92 (d, 3H), 3.52 (s, 2H), 3.30 (m, 4H), 2.52 (s, 3H), 2.28 (m, 6H)
MS: (ESI+) MH+=555.67.

Cmpd 77
N-(5-((diethylamino)methyl)-2-methylphenyl)-4-((5-ethoxy-4-(4-fluorophenyl)pyrimidin-2-yl)amino)benzamide
¹NMR (500 MHz, CD₃OD): 8.61 (t, 2H), 8.39 (s, 1H), 8.19 (m, 2H), 7.75 (m, 2H), 7.30 (s, 1H), 7.24 (d, 1H), 7.11 (m, 3H), 4.11 (s, 2H), 3.93 (s, 3H), 3.61 (s, 2H), 2.55 (m, 4H), 2.28 (s, 3H), 1.07 (m, 6H)
MS: (ESI+) MH+=528.64.

Cmpd 78
3-Fluoro-4-[4-(4-fluoro-phenyl)-5-methylsulfanyl-pyrimidin-2-ylamino]-N-(2-methyl-5-piperazin-1-ylmethyl-phenyl)-benzamide
¹NMR (500 MHz, CDCl₃): 8.71 (t, 1H), 8.69 (s, 1H), 7.86 (dd, 2H), 7.82 (s, 1H), 7.71-7.63 (m, 4H), 7.21-7.16 (m, 3H), 7.09 (d, 1H), 3.47 (s, 2H), 3.06 (b, 1H), 2.89 (t, 4H), 2.43 (s, 4H), 2.30 (s, 6H).
MS: (ESI+) MH+=561.55.

Cmpd 79
4-((4-(4-fluorophenyl)-5-methoxypyrimidin-2-yl)amino)-N-(2-methyl-5-(piperazin-1-ylmethyl)phenyl)benzamide
¹NMR (500 MHz, CD₃OD): 8.65 (t, 1H), 8.40 (s, 1H), 8.20 (t, 2H), 7.75 (m, 2H), 7.30 (s, 1H), 7.16 (m, 4H), 3.92 (s, 3H), 3.52 (s, 2H), 3.30 (s, 4H), 2.28 (t, 4H), 1.89 (s, 3H)
MS: (ESI+) MH+=527.62.

Cmpd 80
4-((5-methoxy-4-(4-(trifluoromethoxy)phenyl)pyrimidin-2-yl)amino)-N-(2-methyl-5-(piperazin-1-ylmethyl)phenyl)benzamide
¹NMR (500 MHz, CD₃OD): 8.41 (s, 1H), 8.27 (d, 2H), 7.69 (m, 2H), 7.65 (m, 2H), 7.37 (d, 1H), 7.32 (s, 1H), 7.24 (m, 2H), 3.94 (S, 3H), 3.56 (S, 2H), 3.34 (s, 4H), 3.30 (t, 4H), 2.29 (s, 3H)
MS: (ESI+) MH+=611.61.

Cmpd 81
N-(2-Methyl-5-morpholin-4-ylmethyl-phenyl)-4-[5-methylsulfanyl-4-(4-trifluoromethoxy-phenyl)-pyridin-2-ylamino]-benzamide
¹NMR (500 MHz, CDCl₃): 8.32 (s, 1H), 7.91 (s, 1H), 7.85 (d, 2H), 7.62 (s, 1H), 7.48 (d, 2H), 7.31 (d, 2H), 7.18 (d, 1H), 7.08 (s, 1H), 6.97 (d, 1H), 6.87 (s, 1H), 6.79 (d, 1H), 6.64 (d, 1H), 3.70 (s, 4H), 3.58 (s, 2H), 2.4 (s, 4H), 2.31 (s, 3H), 2.14 (s, 3H).
MS: (ESI+) MH+=609.39.
Cmpd 82
N-[2-Methyl-5-(4-methyl-piperazin-1-ylmethyl)-phenyl]-4-[5-methylsulfanyl-4-(4-trifluoromethoxy -phenyl)-pyridin-2-ylamino]-benzamide
¹NMR (500 MHz, CDCl₃): 8.32 (d, 1H), 7.90-7.84 (m, 3H), 7.63 (d, 1H), 7.53 (d, 2H), 7.49 (d, 2H), 7.30 (d, 2H), 7.17 (s, 1H), 7.15 (d, 1H), 7.05 (d, 1H), 6.90 (s, 1H), 3.52 (s, 2H), 2.57 (b, 8H), 2.32 (s, 3H), 2.25 (s, 3H).
MS: (ESI+) MH+=622.36.
Cmpd 83
N-(5-Dimethylaminomethyl-2-methyl-phenyl)-4-[5-methylsulfanyl-4-(4-trifluoromethoxy-phenyl) -pyridin-2-ylamino]-benzamide
¹NMR (500 MHz, CDCl₃): 8.32 (d, 1H), 7.93 (s, 1H), 7.84-7.79 (m, 3H), 7.61 (d, 2H), 7.56 (d, 2H), 7.50 (d, 2H), 7.30 (d, 2H), 7.17 (s, 1H), 6.82 (s, 1H), 3.70 (s, 2H), 2.50 (s, 6H), 2.32 (s, 3H), 2.15 (s, 3H).
MS: (ESI+) MH+=567.54.
Cmpd 84
4-[4-(4-Fluoro-phenyl)-5-methylsulfanyl-pyridin-2-ylamino]-N-(2-methyl-5-morpholin-4-ylmethyl-phenyl)-benzamide
¹NMR (500 MHz, CDCl₃): 8.31 (s, 1H), 7.92 (s, 1H), 7.85 (d, 2H), 7.61 (s, 1H), 7.53 (d, 2H), 7.44 (d, 2H), 7.18-7.13 (m, 3H), 7.08 (d, 1H), 6.80 (d, 2H), 3.70 (s, 4H), 3.50 (s, 2H), 2.46 (s, 4H), 2.31 (s, 3H), 2.25 (s, 3H).
MS: (ESI+) MH+=543.68.

Example 85

Preparation of 4-[5-Methanesulfinyl-4-(4-trifluoromethoxy-phenyl)-pyrimidin-2-ylamino]-N-(2-methyl-5-morpholin-4-ylmethyl-phenyl)-benzamide (Compound 85)

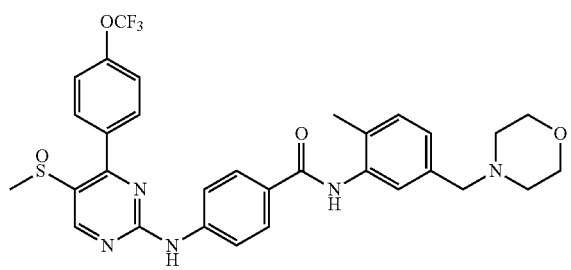

Procedure

To a solution of N-(2-Methyl-5-morpholin-4-ylmethyl-phenyl)-4-[5-methylsulfanyl -4-(4-trifluoromethoxy-phenyl)-pyrimidin-2-ylamino]-benzamide (245.5 mg, 0.4 mmol) in dichloromethane (3.0 mL) at 0° C. was added 70% mCPBA (129 mg, 0.5 mmol). The mixture was stirred at room temperature for 4 h and diluted with dichloromethane. The organic layer was washed with saturated sodium carbonate, dried over magnesium sulfate, filtered, and concentrated on a rotary evaporator. The resulting material was purified by flash column chromatography to afford 4-[5-methanesulfinyl-4-(4-trifluoromethoxy-phenyl)-pyrimidin-2-ylamino]-N-(2-methyl-5-morpholin-4-ylmethyl-phenyl)-benzamide as a white solid (8.2 mg, yield=3.3%).
¹NMR (500 MHz, CDCl₃): 8.57 (s, 1H), 8.16 (s, 1H), 7.90 (m, 4H), 7.81 (m, 2H), 7.47 (s, 1H), 7.44 (m, 3H), 4.43 (m, 4H), 3.75 (d, 2H), 3.39 (t, 2H), 3.06 (d, 2H), 2.37 (s, 3H), 2.31 (s, 3H).

Example 86

Preparation of N-(2-methyl-5-(morpholinomethyl)phenyl)-4-((5-(methylthio)-6-(4-(trifluoromethoxy)phenyl)pyridin-2-yl)amino)benzamide (Compound 86)

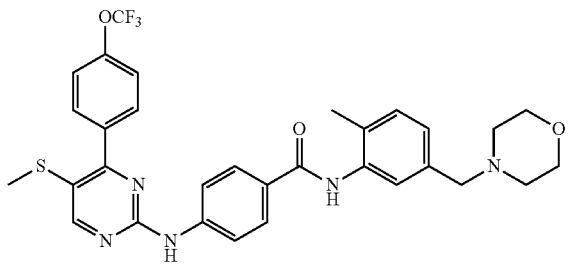 [SMILES: CSc1cnc(Nc2ccc(C(=O)Nc3cc(CN4CCOCC4)ccc3C)cc2)nc1-c1ccc(OC(F)(F)F)cc1]

Compound 86 was prepared according to Scheme 2.
The data of the compounds of Examples 86 are given below:
Compound 86
N-(2-methyl-5-(morpholinomethyl)phenyl)-4-((5-(methylthio)-6-(4-(trifluoromethoxy)phenyl)pyridin-2-yl)amino)benzamide
1NMR (500 MHz, CDCl3): 8.30 (s, 1H), 7.85 (d, 1H), 7.77 (d, 2H), 7.54 (s, 1H), 7.52 (d, 2H), 7.47 (d, 2H), 7.05-7.33 (m, 4H), 7.03 (d, 2H), 6.80 (s, 1H), 3.68 (s, 2H), 3.48 (s, 4H), 2.69 (s, 4H), 2.25 (s, 3H), 2.27 (s, 3H).
MS: (ESI+) MH+=608.68.

Example 87

Preparation of N-(5-((diethylamino)methyl-2-methylphenyl)-4-((5-(methylthio)-4-(4-(trifluoromethoxy)phenyl) pyridin-2-yl)amino)benzamide (Compound 87)

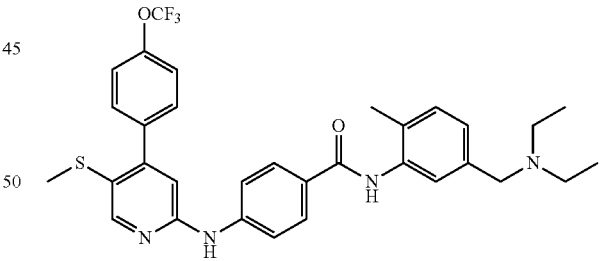

Compound 87 was prepared according to Scheme 2
The data of the compounds of Examples 87 are given below:
Compound 87
N-(5-((diethylamino)methyl)-2-methylphenyl)-4-((5-(methylthio)-4-(4-(trifluoromethoxy)phenyl)pyridin-2-yl)amino) benzamide
1NMR (500 MHz, CDCl3): 7.84 (d, 1H), 7.74-7.59 (m, 2H), 7.65 (d, 1H), 7.54 (d, 2H), 7.53 (d, 2H), 7.42 (d, 2H), 7.21-7.24 (m, 6H), 6.92 (d, 1H), 6.82 (s, 1H), 6.75 (s, 1H), 6.59 (d, 1H), 4.03 (s, 4H), 3.99 (s, 3H), 2.16 (s, 3H), 2.08 (s, 3H), 1.19-1.29 (m, 6H).
MS: (ESI+) MH+=594.70.

Example 88

Preparation of 4-((5-amino-4-(4-(trifluoromethoxy)phenyl)pyrimidin-2-yl)amino)-N-(2-methyl-5-(morpholinomethyl)phenyl)benzamide (Compound 88)

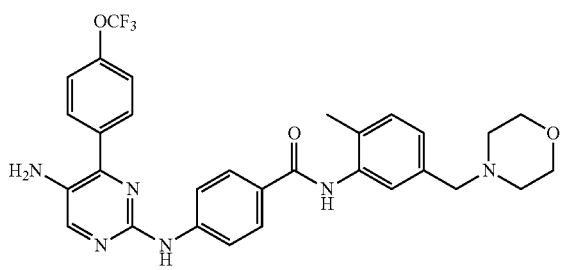 [SMILES: Cc1ccc(CN2CCOCC2)cc1NC(=O)c1ccc(Nc2ncc(N)c(-c3ccc(OC(F)(F)F)cc3)n2)cc1]

Compound 88 was prepared according to Scheme 1

The data of the compounds of Examples 88 are given below:
4-((5-amino-4-(4-(trifluoromethoxy)phenyl)pyrimidin-2-yl)amino)-N-(2-methyl-5-(morpholinomethyl)phenyl)benzamide
1NMR (500 MHz, CDCl3): 8.01-7.80 (m, 5H), 7.74 (d, 2H), 7.62 (s, 1H), 7.39 (d, 2H), 7.18 (d, 2H), 7.08 (d, 1H), 3.72-3.71 (m, 4H), 3.57 (s, 1H), 3.50-3.49 (m, 2H), 2.47-2.46 (m, 4H), 2.32 (s, 3H).
MS: (ESI+) MH+=579.13.

Example 89

Preparation of 4-((4-(4-fluorophenyl)-5-(methylthio)pyridin-2-yl)amino)-N-(2-methyl-5-((4-methylpiperazin-1-yl)methyl)phenyl)benzamide (Compound 89)

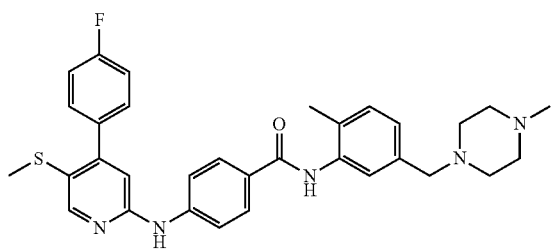

Compound 89 was prepared according to Scheme 2

The data of the compounds of Examples 89 are given below:
4-((4-(4-fluorophenyl)-5-(methylthio)pyridin-2-yl)amino)-N-(2-methyl-5-((4-methylpiperazin-1-yl)methyl)phenyl)benzamide
1NMR (500 MHz, CDCl3): 8.29 (s, 1H), 7.91 (d, 2H), 7.88 (d, 2H), 7.65 (m, 3H), 7.56 (d, 2H), 7.34 (m, 3H), 7.14-7.29 (m, 4H), 7.12 (d, 1H), 3.60 (s, 2H), 3.11 (s, 4H), 2.73 (s, 4H), 2.64 (s, 3H), 2.28 (s, 3H), 2.19 (s, 3H).
MS: (ESI+) MH+=556.72.

Example 90

Preparation of N-(2-methyl-5-((4-methylpiperazin-1-yl)methyl)phenyl)-4-((5-(methylthio)-4-(4-(trifluoromethyl)phenyl)pyridin-2-yl)amino)benzamide (Compound 90)

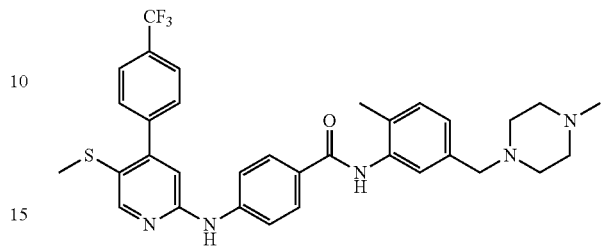

Compound 90 was prepared according to Scheme 2
The data of the compounds of Examples 90 are given below:
N-(2-methyl-5-((4-methylpiperazin-1-yl)methyl)phenyl)-4-((5-(methylthio)-4-(4-(trifluoromethyl)phenyl)pyridin-2-yl)amino)benzamide
1NMR (500 MHz, CDCl3): 8.31 (s, 1H), 7.80-7.86 (m, 4H), 7.59-7.62 (m, 2H), 7.47 (d0, 2H), 7.26-7.30 (m, 4H), 7.13 (d, 1H), 6.96 (d, 2H), 6.83 (s, 1H), 6.61 (m, 2H), 3.50 (s, 2H), 2.75 (s, 4H), 2.51 (s, 4H), 2.36 (s, 3H), 2.24 (s, 3H), 2.12 (s, 3H).
MS: (ESI+) MH+=606.32.

Example 91

Preparation of N-(2-methyl-5-(morpholinomethyl)phenyl)-4-((5-(methylamino)-4-(4-(trifluoromethoxy)phenyl)pyrimidin-2-yl)amino)benzamide (Compound 91)

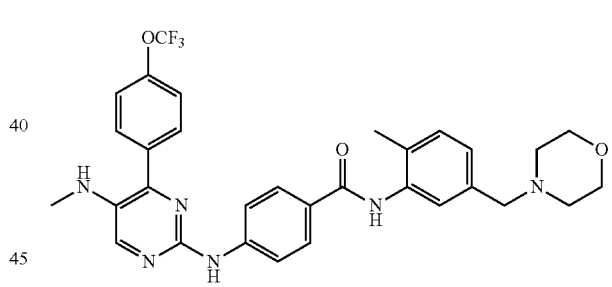

Compound 91 was prepared according to Scheme 3
The data of the compounds of Example 91 are given below:
N-(2-methyl-5-(morpholinomethyl)phenyl)-4-((5-(methylamino)-4-(4-(trifluoromethoxy)phenyl)pyrimidin-2-yl)amino)benzamide
1NMR (500 MHz, CDCl3): 8.06 (s, 1H), 7.93 (br, 1H), 7.83 (dd, 4H), 7.73 (d, 2H), 7.63 (s, 1H), 7.37 (d, 2H), 7.26 (s, 1H), 7.23 (br, 1H), 3.71 (m, 4H), 3.47 (s, 2H), 2.87 (d, 2H), 2.46-2.41 (m, 4H), 2.31 (s, 3H).
MS: (ESI+) MH+=593.3.

Biological Examples

Example 92

Transient Transfection of C3H10T1/2 and Reporter Assay

A cell-based screen for inhibitors of the hedgehog pathway was performed using a transient transfection system in $C_3H_{10}T_{1/2}$ cells with pGL3-7xGli-Luciferase reporter plasmids $C_3H_{10}T_{1/2}$ cells (ATCC, cat.#CCL-226) were seeded into 6-well plates at $8\times10^4$ cells/well in a BME medium containing 10% heat-inactivated FBS. Cells were transfected the next morning with 500 ng/well pGL3-7xGli-Luciferase reporter plasmids and 100 ng/well pRL-TK Renilla luciferase reporter plasmids (Promega)using Gene-Juice transfection reagent (Novagene). After 24 h, transfected cells were collected by trypsin treatment and re-plated in 96-well plates in an RPMI medium containing 0.5% FBS with a density of $1.5\times10^4$ cells/well. Compounds were dissolved in DMSO with serial dilutions and were then added to the assay plate. SAG (Hh-Ag 1.3) (Santa Cruz) was added to the assay plated for a final concentration 20 nM. The assay plates were incubated at 37° C. for 48 hr.

A transient transfection system with a Smo wild type or a Smo D473H mutant was also used for compound screening. For the SMO inhibition experiments, cells were transfected with an additional 500 ng/well of wild-type or D473H-mutant type SMO construct (pLPCX-SMO or pLPCX-SMO-D473H). After 24 h, transfected cells were collected by trypsin treatment and re-plated in 96-well plates in an RPMI medium containing 0.5% FBS with a density of $1.5\times10^4$ cells/well. Compounds were dissolved in DMSO with serial dilutions and were then added to the assay plate. The assay plates were incubated at 37° C. for 48 hr.

Firefly luciferase and Renilla luciferase activity was determined using the Dual-Glo Luciferase reporter assay system (Promega) with a Victor3 plate reader (PerkinElmer Life Sciences). Firefly luciferase readings were normalized to Renilla luciferase to correct for transfection efficiency. Luminance reading for the $C_3H_{10}T_{1/2}$-Gli-Luc assay was normalized based on DMSO control with SAG stimulation (100% pathway activity) and without SAG stimulation (0% pathway activity). $IC_{50}$ values, defined as the inflection point of the logistic curve, were determined by nonlinear regression using the Prism 5 software (GraphPad).

The reporter assay of $C_3H_{10}T_{1/2}$-Gli-Luc cells transfected with a wild-type, D473H mutant Smo mutant was carried out with the same protocol but without SAG stimulation. Luminance reading for the SMO inhibition experiments assay was normalized based on DMSO control (100% of the pathway activity) and a known Smo antagonist (ALLO-2 at 10 μM, 0% of the pathway activity).

Compounds of the invention were tested in those assays and demonstrated the ability to modulate the Hedgehog pathway activity. The compounds described in Table 2 were all tested in those assays and have an activity of less than about 2 μM. The following embodiments are directed to the compounds themselves as well as their use in a method of treatment. For example, in one embodiment of the invention, the Hedgehog pathway modulators in Table 2 have a cellular activity of about 2000 nM or less in a $C_3H_{10}T_{1/2}$ cell assay. In another embodiment, the Hedgehog pathway modulators in Table 2 have a cellular activity of about 250 nM or less in a $C_3H_{10}T_{1/2}$ cell assay. The results of assays are shown in Table 2 (+ means >1000 nM; ++ means 100 nM to 1000 nM; and +++ means <100 nM).

TABLE 2

Biological Data

| Compd No. | Inhibition of Gli-Luc expression [IC50, nM] | Inhibition of C3H10T1/2-Gli-Luc-Smo-WT [IC50, nM] | Inhibition of C3H10T1/2-Gli-Luc-Smo-D473H [IC50, nM] | Compd No. | Inhibition of Gli-Luc expression [IC50, nM] | Inhibition of C3H10T1/2-Gli-Luc-Smo-WT [IC50, nM] | Inhibition of C3H10T1/2-Gli-Luc-Smo-D473H [IC50, nM] |
|---|---|---|---|---|---|---|---|
| 1 | ++ | ++ | + | 2 | ++ | ++ | ++ |
| 3 | ++ | ++ | ++ | 4 | ++ | ++ | ++ |
| 5 | ++ | ++ | ++ | 6 | +++ | +++ | +++ |
| 7 | ++ | ++ | ++ | 8 | ++ | ++ | ++ |
| 9 | +++ | +++ | ++ | 10 | ++ | ++ | ++ |
| 11 | ++ | ++ | ++ | 12 | ++ | ++ | ++ |
| 13 | ++ | ++ | ++ | 14 | +++ | ++ | ++ |
| 15 | +++ | +++ | ++ | 16 | ++ | ++ | ++ |
| 17 | ++ | ++ | ++ | 18 | ++ | ++ | ++ |
| 19 | ++ | ++ | ++ | 20 | +++ | +++ | ++ |
| 21 | +++ | +++ | ++ | 22 | +++ | +++ | ++ |
| 23 | ++ | +++ | ++ | 24 | +++ | +++ | +++ |
| 25 | ++ | ++ | ++ | 26 | +++ | +++ | ++ |
| 27 | +++ | +++ | ++ | 28 | +++ | ++ | ++ |
| 29 | ++ | ++ | ++ | 30 | +++ | +++ | ++ |
| 31 | +++ | +++ | ++ | 32 | ++ | ++ | ++ |
| 33 | +++ | +++ | ++ | 34 | +++ | ++ | ++ |
| 35 | +++ | +++ | ++ | 36 | +++ | +++ | ++ |
| 37 | +++ | +++ | ++ | 38 | +++ | +++ | +++ |
| 39 | ++ | ++ | ++ | 40 | +++ | +++ | +++ |
| 41 | +++ | +++ | ++ | 42 | +++ | +++ | ++ |
| 43 | +++ | +++ | ++ | 44 | +++ | +++ | +++ |
| 45 | +++ | +++ | +++ | 46 | +++ | +++ | ++ |
| 47 | +++ | +++ | ++ | 48 | +++ | +++ | ++ |
| 49 | ++ | ++ | + | 50 | +++ | +++ | ++ |
| 51 | +++ | +++ | ++ | 52 | +++ | +++ | + |
| 53 | +++ | +++ | +++ | 54 | +++ | ++ | ++ |
| 55 | +++ | +++ | +++ | 56 | +++ | +++ | ++ |
| 57 | +++ | +++ | ++ | 58 | +++ | +++ | ++ |
| 59 | ++ | ++ | ++ | 60 | +++ | +++ | +++ |
| 61 | +++ | +++ | ++ | 62 | +++ | +++ | ++ |
| 63 | +++ | +++ | +++ | 64 | +++ | +++ | +++ |
| 65 | +++ | +++ | ++ | 66 | +++ | +++ | ++ |
| 67 | +++ | +++ | ++ | 68 | ++ | +++ | ++ |

TABLE 2-continued

Biological Data

| Compd No. | Inhibition of Gli-Luc expression [IC50, nM] | Inhibition of C3H10T1/2-Gli-Luc-Smo-WT [IC50, nM] | Inhibition of C3H10T1/2-Gli-Luc-Smo-D473H [IC50, nM] | Compd No. | Inhibition of Gli-Luc expression [IC50, nM] | Inhibition of C3H10T1/2-Gli-Luc-Smo-WT [IC50, nM] | Inhibition of C3H10T1/2-Gli-Luc-Smo-D473H [IC50, nM] |
|---|---|---|---|---|---|---|---|
| 69 | +++ | +++ | ++ | 70 | +++ | +++ | +++ |
| 71 | +++ | +++ | +++ | 72 | +++ | +++ | +++ |
| 73 | +++ | +++ | ++ | 74 | +++ | +++ | ++ |
| 75 | +++ | +++ | ++ | 76 | +++ | +++ | +++ |
| 77 | +++ | +++ | ++ | 78 | ++ | ++ | ++ |
| 79 | +++ | ++ | ++ | 80 | +++ | ++ | ++ |
| 81 | +++ | +++ | +++ | 82 | +++ | +++ | +++ |
| 83 | +++ | +++ | +++ | 84 | +++ | +++ | ++ |
| 85 | +++ | +++ | +++ | 86 | +++ | +++ | +++ |
| 87 | +++ | +++ | +++ | 88 | +++ | +++ | +++ |
| 89 | +++ | +++ | ++ | 90 | +++ | +++ | ++ |
| 91 | +++ | +++ | +++ | | | | |

What is claimed is:

1. A compound of formula (I):

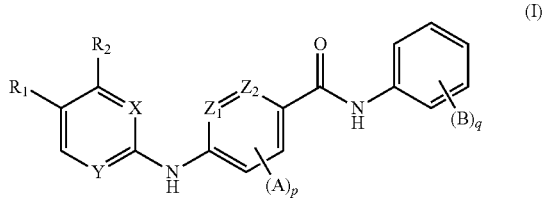

(I)

wherein:
X and Y are each independently N or CH, and at least one of X and Y is N;
$Z_1$ and $Z_2$ are each independently N or CH, and at least one of $Z_1$ and $Z_2$ is CH;
$R_1$ is $NH_2$; $OR_3$, $NHR_3$, $SR_3$ or $SOR_3$;
$R_2$ is alkyl, cycloalkyl, aryl, heteroaryl, or heterocycloalkyl wherein the alkyl, cycloalkyl, aryl, heteroaryl, and heterocycloalkyl are optionally substituted with 1, 2, or 3 $R_4$;
$R_3$ is optionally substituted alkyl or cycloalkyl;
$R_4$ is halo, hydroxy, mercapto, cyano, nitro, amino, alkyl, alkoxy, alkylamino, dialkylamino, cycloalkyl, haloalkyl, haloalkoxy, aryl, heteroaryl, or heterocycloalkyl;
A and B are each independently hydrogen, halo, cyano, amino, alkyl, haloalkyl, alkoxy, haloalkoxy, cycloalkyl, halocycloalkyl, alkylaminoalkyl, alkylaminodialkyl, or alkyl-heterocycloalkyl, wherein the alkyl, alkoxy, cycloalkyl and heterocycloalkyl are optionally substituted;
p is 0, 1, 2, 3, or 4; and
q is 0, 1, 2, 3, or 4;
or a pharmaceutically acceptable salt, geometric isomer, enantiomer, diastereomer, prodrug, or solvate thereof.

2. The compound according to claim 1, wherein at least one of X and Y is N; both $Z_1$ and $Z_2$ are CH, or one of $Z_1$ and $Z_2$ is N and the other is CH; $R_1$ is $NH_2$, $OR_3$, $NHR_3$, $SR_3$ or $SOR_3$; $R_3$ is optionally substituted alkyl; $R_2$ is aryl, heteroaryl, or heterocycloalkyl, which are optionally substituted with 1, 2, or 3 $R_4$; $R_4$ is halo, hydroxy, mercapto, cyano, nitro, amino, alkyl, alkoxy, alkylamino, dialkylamino, cycloalkyl, haloalkyl, or haloalkoxy; A is hydrogen, halo, cyano, amino, alkyl, haloalkyl, alkoxy, or haloalkoxy, wherein the alkyl and alkoxy are optionally substituted; B is hydrogen, halo, cyano, amino, alkyl, haloalkyl, alkoxy, haloalkoxy, alkylaminoalkyl, alkylaminodialkyl, or alkyl-heterocycloalkyl, wherein the alkyl and alkoxy are optionally substituted; p is 0, 1, or 2; and q is 0, 1, 2, or 3.

3. The compound according to claim 2, wherein both X and Y are N, or, X is CH and Y is N; both $Z_1$ and $Z_2$ are CH, or $Z_1$ is N and $Z_2$ is CH; $R_1$ is $NH_2$, $OR_3$, $NHR_3$, $SR_3$ or $SOR_3$; $R_3$ is optionally substituted alkyl; $R_2$ is aryl or heteroaryl, which is optionally substituted with 1, 2, or 3 $R_4$; $R_4$ is halo, cyano, alkyl, or haloalkoxy; A is hydrogen or halogen; B is cyano, halo, alkyl, haloalkyl, alkoxy, alkyl-heterocycloalkyl, or alkylaminodialkyl; p is 0 or 1; and q is 0, 1, or 2.

4. A compound, which is selected from:
N-(2,6-Dimethyl-phenyl)-4-[5-methylsulfanyl-4-(4-trifluoromethoxy-phenyl)-pyrimidin-2-ylamino]-benzamide;
4-[4-(4-Cyano-phenyl)-5-methylsulfanyl-pyrimidin-2-ylamino]-N-(2,6-dimethyl-phenyl)-benzamide;
4-[4-(4-Cyano-phenyl)-5-methylsulfanyl-pyrimidin-2-ylamino]-N-phenyl-benzamide;
N-(3-Chloro-4-trifluoromethyl-phenyl)-4-[4-(4-cyano-phenyl)-5-methylsulfanyl-pyrimidin-2-ylamino]-benzamide;
4-[4-(2-Fluoro-pyridin-3-yl)-5-methylsulfanyl-pyrimidin-2-ylamino]-N-phenyl-benzamide;
N-(2,6-Dimethyl-phenyl)-4-[4-(2-fluoro-pyridin-3-yl)-5-methylsulfanyl-pyrimidin-2-ylamino]-benzamide;
N-(4-Chloro-3-trifluoromethyl-phenyl)-4-[4-(6-ethoxy-pyridin-3-yl)-5-methylsulfanyl-pyrimidin -2-ylamino]-benzamide;
N-(2,6-Difluoro-phenyl)-4-[4-(2-fluoro-pyridin-3-yl)-5-methylsulfanyl-pyrimidin-2-ylamino]-benzamide;
N-(2,6-Dimethoxy-phenyl)-4-[4-(2-fluoro-pyridin-3-yl)-5-methylsulfanyl-pyrimidin-2-ylamino]-benzamide;
N-(2,6-Difluoro-phenyl)-4-(5-methylsulfanyl-4-pyridin-3-yl-pyrimidin-2-ylamino)-benzamide;
4-[4-(2-Fluoro-pyridin-3-yl)-5-methylsulfanyl-pyrimidin-2-ylamino]-N-o-tolyl-benzamide;
N-(2,6-Dimethyl-phenyl)-3-fluoro-4-[4-(2-fluoro-pyridin-3-yl)-5-methylsulfanyl-pyrimidin-2-ylamino]-benzamide;

N-(2,6-Dimethoxy-phenyl)-3-fluoro-4-[4-(2-fluoro-pyridin-3-yl)-5-methylsulfanyl-pyrimidin-2-ylamino]-benzamide;

4-[4-(2-Fluoro-pyridin-3-yl)-5-methylsulfanyl-pyrimidin-2-ylamino]-N-(2-methoxy-6-methyl-phenyl)-benzamide;

3-Fluoro-4-[4-(2-fluoro-pyridin-3-yl)-5-methylsulfanyl-pyrimidin-2-ylamino]-N-(2-methoxy-6-methyl-phenyl)-benzamide;

3-Fluoro-4-[4-(2-fluoro-pyridin-3-yl)-5-methylsulfanyl-pyrimidin-2-ylamino]-N-o-tolyl-benzamide;

3-Fluoro-4-[4-(6-fluoro-pyridin-3-yl)-5-methylsulfanyl-pyrimidin-2-ylamino]-N-(2-methoxy-6-methyl-phenyl)-benzamide;

N-(4-Cyano-phenyl)-4-[4-(2-fluoro-pyridin-3-yl)-5-methylsulfanyl-pyrimidin-2-ylamino]-benzamide;

4-(5-Methylsulfanyl-4-phenyl-pyrimidin-2-ylamino)-N-o-tolyl-benzamide;

N-(2-Methyl-5-morpholin-4-ylmethyl-phenyl)-4-(5-methylsulfanyl-4-phenyl-pyrimidin-2-ylamino)-benzamide;

N-(2,6-Dimethoxy-phenyl)-4-(5-methylsulfanyl-4-phenyl-pyrimidin-2-ylamino)-benzamide;

N-(2,6-Dimethoxy-phenyl)-4-[5-methylsulfanyl-4-(4-trifluoromethoxy-phenyl)-pyrimidin-2-ylamino]-benzamide;

4-[5-Methylsulfanyl-4-(4-trifluoromethoxy-phenyl)-pyrimidin-2-ylamino]-N-o-tolyl-benzamide;

N-(2-Methyl-5-morpholin-4-ylmethyl-phenyl)-4-[5-methylsulfanyl-4-(4-trifluoromethoxy-phenyl)-pyrimidin-2-ylamino]-benzamide;

N-(2-Methoxy-6-methyl-phenyl)-4-[5-methylsulfanyl-4-(4-trifluoromethoxy-phenyl)-pyrimidin-2-ylamino]-benzamide;

N-(2-Methyl-5-morpholin-4-ylmethyl-phenyl)-4-(5-methylsulfanyl-4-pyridin-4-yl-pyrimidin-2-ylamino)-benzamide;

N-(2-Methyl-5-morpholin-4-ylmethyl-phenyl)-4-[5-methylsulfanyl-4-(4-trifluoromethyl-phenyl)-pyrimidin-2-ylamino]-benzamide;

N-(2-Methyl-5-piperidin-1-ylmethyl-phenyl)-4-[5-methylsulfanyl-4-(4-trifluoromethyl-phenyl)-pyrimidin-2-ylamino]-benzamide;

N-(2,6-Dimethyl-phenyl)-4-[4-(4-fluoro-phenyl)-5-methylsulfanyl-pyrimidin-2-ylamino]-benzamide;

4-[4-(4-Fluoro-phenyl)-5-methylsulfanyl-pyrimidin-2-ylamino]-N-(2-methyl-5-morpholin-4-ylmethyl-phenyl)-benzamide;

N-(5-Dimethylaminomethyl-2-methyl-phenyl)-4-[4-(4-fluoro-phenyl)-5-methylsulfanyl-pyrimidin-2-ylamino]-benzamide;

N-(5-Dimethylaminomethyl-2-methyl-phenyl)-4-[5-methylsulfanyl-4-(4-trifluoromethyl-phenyl)-pyrimidin-2-ylamino]-benzamide;

4-[4-(4-Cyano-phenyl)-5-methylsulfanyl-pyrimidin-2-ylamino]-N-(2-methyl-5-morpholin-4-ylmethyl-phenyl)-benzamide;

4-[4-(4-Cyano-phenyl)-5-methylsulfanyl-pyrimidin-2-ylamino]-N-(5-dimethylaminomethyl-2-methyl-phenyl)-benzamide;

4-[4-(4-Cyano-phenyl)-5-methylsulfanyl-pyrimidin-2-ylamino]-N-[2-methyl-5-(4-methyl-piperazin-1-ylmethyl)-phenyl]-benzamide;

4-[4-(4-Fluoro-phenyl)-5-methylsulfanyl-pyrimidin-2-ylamino]-N-[2-methyl-5-(4-methyl-piperazin-1-ylmethyl)-phenyl]-benzamide;

N-[2-Methyl-5-(4-methyl-piperazin-1-ylmethyl)-phenyl]-4-[5-methylsulfanyl-4-(4-trifluoromethoxy-phenyl)-pyrimidin-2-ylamino]-benzamide;

4-[5-Methoxy-4-(4-trifluoromethoxy-phenyl)-pyrimidin-2-ylamino]-N-(2-methyl-5-morpholin-4-ylmethyl-phenyl)-benzamide;

N-(2-Methyl-5-morpholin-4-ylmethyl-phenyl)-4-[4-(1-methyl-1H-pyrazol-4-yl)-5-methylsulfanyl-pyrimidin-2-ylamino]-benzamide;

3-Fluoro-N-(2-methyl-5-morpholin-4-ylmethyl-phenyl)-4-[5-methylsulfanyl-4-(4-trifluoromethoxy-phenyl)-pyrimidin-2-ylamino]-benzamide;

3-Fluoro-4-[4-(4-fluoro-phenyl)-5-methylsulfanyl-pyrimidin-2-ylamino]-N-(2-methyl-5-morpholin-4-ylmethyl-phenyl)-benzamide;

3-Fluoro-4-[4-(4-fluoro-phenyl)-5-methylsulfanyl-pyrimidin-2-ylamino]-N-(2-methyl-5-piperidin-1-ylmethyl-phenyl)-benzamide;

4-[4-(4-Fluoro-phenyl)-5-methylsulfanyl-pyrimidin-2-ylamino]-N-(3-morpholin-4-ylmethyl-phenyl)-benzamide;

3-Fluoro-4-[5-methylsulfanyl-4-(4-trifluoromethoxy-phenyl)-pyrimidin-2-ylamino]-N-(3-morpholin-4-ylmethyl-phenyl)-benzamide;

3-Fluoro-N-(2-methyl-5-morpholin-4-ylmethyl-phenyl)-4-[4-(1-methyl-1H-pyrazol-4-yl)-5-methylsulfanyl-pyrimidin-2-ylamino]-benzamide;

3-Fluoro-N-[2-methyl-5-(4-methyl-piperazin-1-ylmethyl)-phenyl]-4-[4-(1-methyl-1H-pyrazol-4-yl)-5-methylsulfanyl-pyrimidin-2-ylamino]-benzamide;

N-(5-Diethylaminomethyl-2-methyl-phenyl)-4-[4-(4-fluoro-phenyl)-5-methylsulfanyl-pyrimidin-2-ylamino]-benzamide;

4-[4-(4-Fluoro-phenyl)-5-methylsulfanyl-pyrimidin-2-ylamino]-N-(2-methyl-5-piperidin-1-ylmethyl-phenyl)-benzamide;

4-[4-(4-Cyano-phenyl)-5-methoxy-pyrimidin-2-ylamino]-N-(2-methyl-5-morpholin-4-ylmethyl-phenyl)-benzamide;

4-[4-(4-Cyano-phenyl)-5-methoxy-pyrimidin-2-ylamino]-N-(5-diethylaminomethyl-2-methyl-phenyl)-benzamide;

4-[4-(4-Cyano-phenyl)-5-methoxy-pyrimidin-2-ylamino]-N-[2-methyl-5-(4-methyl-piperazin-1-ylmethyl)-phenyl]-benzamide;

4-[5-Methoxy-4-(4-trifluoromethoxy-phenyl)-pyrimidin-2-ylamino]-N-[2-methyl-5-(4-methyl-piperazin-1-ylmethyl)-phenyl]-benzamide;

N-(5-Diethylaminomethyl-2-methyl-phenyl)-3-fluoro-4-[4-(4-fluoro-phenyl)-5-methylsulfanyl-pyrimidin-2-ylamine]-benzamide;

N-(5-Dimethylaminomethyl-2-methyl-phenyl)-4-[5-methylsulfanyl-4-(4-trifluoromethoxy-phenyl)-pyrimidin-2-ylamino]-benzamide;

3-Fluoro-N-(2-fluoro-5-morpholin-4-ylmethyl-phenyl)-4-[5-methylsulfanyl-4-(4-trifluoromethoxy-phenyl)-pyrimidin-2-ylamino]-benzamide;

N-(3-Diethylaminomethyl-phenyl)-3-fluoro-4-[5-methylsulfanyl-4-(4-trifluoromethoxy-phenyl)-pyrimidin-2-ylamino]-benzamide;

3-Fluoro-N-(2-fluoro-5-morpholin-4-ylmethyl-phenyl)-4-[4-(4-fluoro-phenyl)-5-methylsulfanyl-pyrimidin-2-ylamino]-benzamide;

3-Fluoro-N-(2-methoxy-5-morpholin-4-ylmethyl-phenyl)-4-[5-methylsulfanyl-4-(4-trifluoromethoxy-phenyl)-pyrimidin-2-ylamino]-benzamide;

4-[4-(4-Fluoro-phenyl)-5-methylsulfanyl-pyrimidin-2-ylamino]-N-(2-methoxy-5-morpholin-4-ylmethyl-phenyl)-benzamide;

3-Fluoro-4-[4-(4-fluoro-phenyl)-5-methoxy-pyrimidin-2-ylamino]-N-(2-methyl-5-morpholin -4-ylmethyl-phenyl)-benzamide;

N-(5-Diethylaminomethyl-2-methyl-phenyl)-3-fluoro-4-[5-methoxy-4-(4-trifluoromethoxy-phenyl) -pyrimidin-2-ylamino]-benzamide;

3-Fluoro-4-[5-methoxy-4-(4-trifluoromethoxy-phenyl)-pyrimidin-2-ylamino]-N-[2-methyl-5-(4-methyl-piperazin-1-ylmethyl)-phenyl]-benzamide;

N-(2-Methyl-5-morpholin-4-ylmethyl-phenyl)-6-[5-methylsulfanyl-4-(4-trifluoromethoxy-phenyl) -pyrimidin-2-ylamino]-nicotinamide;

6-[5-Methylsulfanyl-4-(4-trifluoromethoxy-phenyl)-pyrimidin-2-ylamino]-N-(3-morpholin-4-ylmethyl-phenyl)-nicotinamide;

4-[5-Methylsulfanyl-4-(4-trifluoromethoxy-phenyl)-pyrimidin-2-ylamino]-N-(3-morpholin-4-ylmethyl-phenyl)-benzamide;

N-(5-Diethylaminomethyl-2-methyl-phenyl)-6-[5-methylsulfanyl-4-(4-trifluoromethoxy-phenyl) -pyrimidin-2-ylamino]-nicotinamide;

4-[4-(6-Fluoro-pyridin-3-yl)-5-methylsulfanyl-pyrimidin-2-ylamino]-N-(2-methyl-5-morpholin -4-ylmethyl-phenyl)-benzamide;

N-(2-Methyl-5-morpholin-4-ylmethyl-phenyl)-4-[5-methylsulfanyl-4-(6-trifluoromethyl-pyridin -3-yl)-pyrimidin-2-ylamino]-benzamide;

4-[5-Methylsulfanyl-4-(6-trifluoromethyl-pyridin-3-yl)-pyrimidin-2-ylamino]-N-(3-morpholin -4-ylmethyl-phenyl)-benzamide;

N-(2-Fluoro-5-morpholin-4-ylmethyl-phenyl)-4-[5-methylsulfanyl-4-(4-trifluoromethoxy-phenyl) -pyrimidin-2-ylamino]-benzamide;

N-(2-Fluoro-5-morpholin-4-ylmethyl-phenyl)-4-[4-(4-fluoro-phenyl)-5-methylsulfanyl-pyrimidin -2-ylamino]-benzamide;

4-[5-Ethoxy-4-(4-trifluoromethoxy-phenyl)-pyrimidin-2-ylamino]-N-(2-methyl-5-morpholin -4-ylmethyl-phenyl)-benzamide;

4-[5-Ethoxy-4-(4-trifluoromethoxy-phenyl)-pyrimidin-2-ylamino]-N-[2-methyl-5-(4-methyl-piperazin -1-ylmethyl)-phenyl]-benzamide;

N-(5-Diethylaminomethyl-2-methyl-phenyl)-4-[5-ethoxy-4-(4-trifluoromethoxy-phenyl)-pyrimidin -2-ylamino]-benzamide;

4-[5-Ethoxy-4-(4-fluoro-phenyl)-pyrimidin-2-ylamino]-N-(2-methyl-5-morpholin-4-ylmethyl -phenyl)-benzamide;

4-[5-Ethoxy-4-(4-fluoro-phenyl)-pyrimidin-2-ylamino]-N-[2-methyl-5-(4-methyl-piperazin-1-ylmethyl)-phenyl]-benzamide;

N-(5-Diethylaminomethyl-2-methyl-phenyl)-4-[5-ethoxy-4-(4-fluoro-phenyl)-pyrimidin-2-ylamino]-benzamide;

3-Fluoro-4-[4-(4-fluoro-phenyl)-5-methylsulfanyl-pyrimidin-2-ylamino]-N-(2-methyl-5-piperazin -1-ylmethyl-phenyl)-benzamide;

4-[4-(4-Fluoro-phenyl)-5-methoxy-pyrimidin-2-ylamino]-N-(2-methyl-5-piperazin-1-ylmethyl -phenyl)-benzamide;

3-Fluoro-4-[4-(4-fluoro-phenyl)-5-methoxy-pyrimidin-2-ylamino]-N-(2-methyl-5-piperazin-1-ylmethyl-phenyl)-benzamide;

N-(2-Methyl-5-morpholin-4-ylmethyl-phenyl)-4-[5-methylsulfanyl-4-(4-trifluoromethoxy-phenyl) -pyridin-2-ylamino]-benzamide;

N-[2-Methyl-5-(4-methyl-piperazin-1-ylmethyl)-phenyl]-4-[5-methylsulfanyl-4-(4-trifluoromethoxy -phenyl)-pyridin-2-ylamino]-benzamide;

N-(5-Dimethylaminomethyl-2-methyl-phenyl)-4-[5-methylsulfanyl-4-(4-trifluoromethoxy-phenyl) -pyridin-2-ylamino]-benzamide;

4-((4-(4-fluorophenyl)-5-(methylthio)pyridin-2-yl)amino)-N-(2-methyl-5-(morpholinomethyl) phenyl)benzamide;

N-(2-methyl-5-(morpholinomethyl)phenyl)-4-((5-(methylsulfinyl)-4-(4-(trifluoromethoxy)phenyl) pyrimidin-2-yl)amino)benzamide;

N-(2-methyl-5-(morpholinomethyl)phenyl)-4-((5-(methylthio)-6-(4-(trifluoromethoxy)phenyl) pyridin-2-yl)amino)benzamide;

N-(5-((diethylamino)methyl)-2-methylphenyl)-4-((5-(methylthio)-4-(4-(trifluoromethoxy)phenyl) pyridin-2-yl)amino)benzamide;

4-((5-amino-4-(4-(trifluoromethoxy)phenyl)pyrimidin-2-yl)amino)-N-(2-methyl-5-(morpholinomethyl) phenyl)benzamide;

4-((4-(4-fluorophenyl)-5-(methylthio)pyridin-2-yl)amino)-N-(2-methyl-5-((4-methylpiperazin -1-yl)methyl)phenyl)benzamide;

N-(2-methyl-5-((4-methylpiperazin-1-yl)methyl)phenyl)-4-((5-(methylthio)-4-(4-(trifluoromethyl)phenyl)pyridin -2-yl)amino)benzamide; and N-(2-methyl-5-(morpholinomethyl)phenyl)-4-((5-(methylamino)-4-(4-(trifluoromethoxy)phenyl)pyrimidin -2-yl)amino)benzamide;

or a pharmaceutically acceptable salt, geometric isomer, enantiomer, distereomer, racemate, prodrug, solvate, or hydrate thereof.

5. A pharmaceutical composition comprising a therapeutically effective amount of a compound of claim 1 or a pharmaceutically acceptable salt, geometric isomer, enantiomer, diastereomer, prodrug, or solvate thereof, and a pharmaceutically acceptable carrier or excipient.

6. A pharmaceutical composition comprising a therapeutically effective amount of a compound of claim 4 or a pharmaceutically acceptable salt, geometric isomer, enantiomer, diastereomer, prodrug, or solvate thereof, and a pharmaceutically acceptable carrier or excipient.

7. A method for preparing a compound of formula (I):

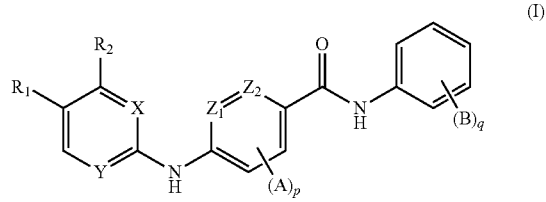

wherein:
X and Y are each independently N or CH, and at least one of X and Y is N;
$Z_1$ and $Z_2$ are each independently N or CH, and at least one of $Z_1$ and $Z_2$ is CH;
$R_1$ is $OR_3$, $NHR_3$, $SR_3$ or $SOR_3$;
$R_2$ is alkyl, cycloalkyl, aryl, heteroaryl, or heterocycloalkyl wherein the alkyl, cycloalkyl, aryl, heteroaryl, and heterocycloalkyl are optionally substituted with 1, 2, or 3 $R_4$;

$R_3$ is optionally substituted alkyl or cycloalkyl;
$R_4$ is halo, hydroxy, mercapto, cyano, nitro, amino, alkyl, alkoxy, alkylamino, dialkylamino, cycloalkyl, haloalkyl, haloalkoxy, aryl, heteroaryl; or heterocycloalkyl;
A and B are each independently hydrogen, halo, cyano, amino, alkyl, haloalkyl, alkoxy, haloalkoxy, cycloalkyl, halocycloalkyl, alkylaminoalkyl, alkylaminodialkyl, or alkyl-heterocycloalkyl, wherein the alkyl, alkoxy, cycloalkyl and heterocycloalkyl are optionally substituted;
p is 0, 1, 2, 3, or 4; and
q is 0, 1, 2, 3, or 4;
or a pharmaceutically acceptable salt, geometric isomer, enantiomer, diastereomer, prodrug, or solvate thereof,
the method comprises:
a. reacting a compound of formula (1)

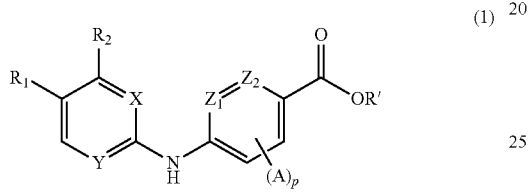

(1)

wherein $R_1$, $R_2$, X, Y, $Z_1$, $Z_2$, A, and p are as defined above, and R' is alkyl;

with a base to obtain a compound of formula (2)

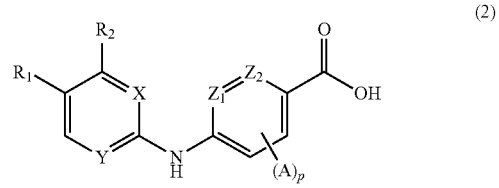

(2)

wherein $R_1$, $R_2$, X, Y, $Z_1$, $Z_2$, A, and p are as defined above; and b. reacting a compound of formula (2) with a compound of formula (3)

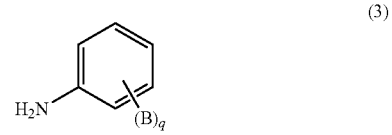

(3)

wherein B and q are as defined above; in the presence of a coupling agent and a solvent to obtain the compound of formula (I).

* * * * *